United States Patent
Sagi et al.

(10) Patent No.: US 12,178,921 B2
(45) Date of Patent: *Dec. 31, 2024

(54) METHOD OF LYOPHILIZING LIPID NANOPARTICLES

(71) Applicant: Arcturus Therapeutics, Inc., San Diego, CA (US)

(72) Inventors: Amit Sagi, San Diego, CA (US); Yanjie Bao, San Diego, CA (US); Priya Prakash Karmali, San Diego, CA (US)

(73) Assignee: Arcturus Therapeutics, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/402,077

(22) Filed: Aug. 13, 2021

(65) Prior Publication Data

US 2022/0047519 A1    Feb. 17, 2022

Related U.S. Application Data

(60) Provisional application No. 63/158,761, filed on Mar. 9, 2021, provisional application No. 63/066,051, filed on Aug. 14, 2020.

(51) Int. Cl.
*A61K 9/51* (2006.01)
*A61K 9/19* (2006.01)
*A61K 48/00* (2006.01)

(52) U.S. Cl.
CPC .............. *A61K 9/5123* (2013.01); *A61K 9/19* (2013.01); *A61K 9/5115* (2013.01); *A61K 48/0033* (2013.01)

(58) Field of Classification Search
CPC ...... A61K 9/5123; A61K 9/19; A61K 9/5115; A61K 48/0033
See application file for complete search history.

(56) References Cited

U.S. PATENT DOCUMENTS

| | | | |
|---|---|---|---|
| 7,332,322 B2 | 2/2008 | Frolov et al. | |
| 7,425,337 B2 | 9/2008 | Smith et al. | |
| 7,442,381 B2 | 10/2008 | Smith et al. | |
| 8,093,367 B2 | 1/2012 | Kore et al. | |
| 8,158,601 B2 | 4/2012 | Chen et al. | |
| 8,304,529 B2 | 11/2012 | Kore et al. | |
| 8,961,995 B2 | 2/2015 | Frolov et al. | |
| 9,254,265 B2 | 2/2016 | Geall et al. | |
| 9,295,646 B2 | 3/2016 | Brito et al. | |
| 9,730,997 B2 | 8/2017 | Perri et al. | |
| 9,770,463 B2 | 9/2017 | Geall et al. | |
| 10,238,733 B2 | 3/2019 | Brito et al. | |
| 10,487,105 B2 | 11/2019 | Chivukula et al. | |
| 11,135,283 B2 | 10/2021 | Berglund et al. | |
| 2009/0155301 A1 | 6/2009 | Mason et al. | |
| 2011/0171255 A1 | 7/2011 | Kiiver et al. | |
| 2011/0207223 A1 | 8/2011 | Tang et al. | |
| 2011/0256175 A1 | 10/2011 | Hope et al. | |
| 2012/0027803 A1 | 2/2012 | Manoharan et al. | |
| 2012/0128760 A1 | 5/2012 | Manoharan et al. | |
| 2012/0156251 A1 | 6/2012 | Brito et al. | |
| 2013/0171241 A1 | 7/2013 | Geall | |
| 2013/0195968 A1 | 8/2013 | Geall et al. | |
| 2013/0315937 A1 | 11/2013 | Lee et al. | |
| 2014/0227346 A1 | 8/2014 | Geall et al. | |
| 2014/0242152 A1 | 8/2014 | Geall et al. | |
| 2015/0024002 A1 | 1/2015 | Perri et al. | |
| 2016/0074500 A1 | 3/2016 | Pushko et al. | |
| 2016/0348132 A1 | 12/2016 | Rayner et al. | |
| 2017/0020819 A1* | 1/2017 | Adami | A61K 9/145 |
| 2017/0152516 A1 | 6/2017 | Knopov et al. | |
| 2018/0036398 A1 | 2/2018 | Hagen et al. | |
| 2018/0104359 A1 | 4/2018 | Kamrud | |
| 2018/0169268 A1 | 6/2018 | Payne et al. | |
| 2018/0171340 A1 | 6/2018 | Kamrud et al. | |
| 2018/0243219 A1* | 8/2018 | Ketterer | A61P 31/00 |
| 2018/0273576 A1 | 9/2018 | Hogrefe et al. | |
| 2018/0327471 A1 | 11/2018 | Limphong et al. | |
| 2019/0091329 A1 | 3/2019 | Brito et al. | |
| 2019/0224299 A1 | 7/2019 | Kamrud et al. | |
| 2019/0231695 A1 | 8/2019 | Adami et al. | |

(Continued)

FOREIGN PATENT DOCUMENTS

| | | | |
|---|---|---|---|
| EP | 2671591 A1 | 12/2013 | |
| EP | 2591114 B1 | 6/2016 | |

(Continued)

OTHER PUBLICATIONS

Ball et al. "Achieving Long-term Stability of Lipid Nanoparticles: Examining the Effect of PH, Temperature, and Lyophilization" Int. J. Nanomedicine 2017, 12, 305-315.

Bou-Mitri, C.; Kaermasha, S. "Lyoprotection and Stabilization of Laccase Extract from Coriolus Hirsutus, Using Selected Additives" AMB Expr. 2018, 8, 152-162.

Guimaraes et al. "Protective Effect of Saccharides on Freeze-Dried Liposomes Encapsulating Drugs" Front. Bioeng. Biotechnol. 2019, 7, 424-431. doi: 10.3389/fbioe.2019.00424.

Ben Halima, N. "Poly (Vinyl Alcohol): Review of its Promising Applications and Insights into Biodegradation" RSC Adv. 2016, 6, 39823-39832.

(Continued)

*Primary Examiner* — Robert A Wax
*Assistant Examiner* — Olga V. Tcherkasskaya
(74) *Attorney, Agent, or Firm* — Mintz Levin Cohn Ferris Glovsky and Popeo, P.C.

(57) ABSTRACT

Methods of preparing lyophilized lipid nanoparticle-nucleic acid compositions are provided. The methods comprise preparing a suspension of lipid nanoparticles with a monosaccharide and one or more excipients selected from thiosulfate, potassium sorbate, sodium benzoate, and iodixanol. Lyophilized lipid nanoparticle-nucleic acid compositions and methods of reconstituting and administering the same are further provided.

16 Claims, 4 Drawing Sheets

(56) References Cited

U.S. PATENT DOCUMENTS

| | | | |
|---|---|---|---|
| 2019/0321458 | A1 | 10/2019 | Sahin et al. |
| 2019/0374650 | A1 | 12/2019 | Moon et al. |
| 2020/0010849 | A1 | 1/2020 | Blair et al. |
| 2020/0069599 | A1 | 3/2020 | Smith et al. |
| 2020/0113830 | A1 | 4/2020 | Geall et al. |
| 2020/0113831 | A1 | 4/2020 | Geall et al. |
| 2020/0222332 | A1 | 7/2020 | Irvine et al. |
| 2020/0230058 | A1 | 7/2020 | Geall et al. |
| 2020/0297634 | A1 | 9/2020 | Karmali et al. |
| 2020/0330585 | A1 | 10/2020 | Mogler et al. |
| 2021/0030859 | A1 | 2/2021 | Bucala et al. |
| 2021/0284974 | A1 | 9/2021 | Chivukula et al. |
| 2021/0290752 | A1 | 9/2021 | Sullivan et al. |
| 2022/0347298 | A1 | 11/2022 | Sullivan et al. |
| 2022/0395570 | A1 | 12/2022 | Rauch et al. |

FOREIGN PATENT DOCUMENTS

| | | | |
|---|---|---|---|
| EP | 3471778 | A2 | 4/2019 |
| EP | 3433369 | B1 | 3/2020 |
| EP | 2729126 | B1 | 12/2020 |
| WO | 2009086558 | A1 | 7/2009 |
| WO | 2009127060 | A1 | 10/2009 |
| WO | 2010048536 | A2 | 4/2010 |
| WO | 2010054406 | A1 | 5/2010 |
| WO | 2010088537 | A2 | 8/2010 |
| WO | 2010129709 | A1 | 11/2010 |
| WO | 2011153493 | A2 | 12/2011 |
| WO | 2013/090634 | A1 | 6/2013 |
| WO | 2014170493 | A2 | 10/2014 |
| WO | 2015051169 | A2 | 4/2015 |
| WO | 2015061491 | A1 | 4/2015 |
| WO | 2017223085 | A2 | 12/2017 |
| WO | 2018078053 | A1 | 5/2018 |
| WO | 2018208856 | A1 | 11/2018 |
| WO | 2018222890 | A1 | 12/2018 |
| WO | 2018222926 | A1 | 12/2018 |
| WO | 2019023566 | A1 | 1/2019 |
| WO | 2020014654 | A1 | 1/2020 |
| WO | 2020035609 | A2 | 2/2020 |
| WO | 2020254535 | A1 | 12/2020 |
| WO | 2020254804 | A1 | 12/2020 |
| WO | 2020255055 | A1 | 12/2020 |
| WO | 2021067181 | A1 | 4/2021 |
| WO | 2021183563 | A1 | 9/2021 |
| WO | 2021183564 | A1 | 9/2021 |
| WO | 2023010128 | A2 | 2/2023 |

OTHER PUBLICATIONS

Khan et al. "Key Interactions of Surfactants in Therapeutic Protein Formulations: A Review" Eur. J. Pharm. Biopharm. 2015, 97, 60-67.
Layre et al. "Freeze-Drying of Composite Core-Shell Nanoparticles" Drug Dev. Ind. Pharm. 2006, 32, 839-846.
Nireesha et al. "Lyophilization/Freeze Drying—An Review" IJNTPS 2013, 3, 87-98.
Pikal, J.M. "Freeze-Drying of Proteins Part I: Process Design" BioPharm 1990, 18-27.
Freeze-Drying / Lyophilization of Pharmaceutical and Biological Products, $2^{nd}$ ed.; Rey, L .; May, J.C., Eds.; Marcel Dekker, 2004.
Suksiriworapong et al. "Development and Characterization of Lyophilized Diazepam-Loaded Polymeric Micelles" AAPS PharmSciTech 2014, 15(1), 52-64.
Tsukamoto et al. "Bovine Serum Albumin as a Lyoprotectant for Preparation of DNA Dry Powder Formulations Using the Spray-Freeze Drying Method" Biol. Pharm. Bull. 2012, 35(7), 1178-1181.
Keyer, V.V.; Shevtsov, A.B .; Shustov, A.V. Cloning Vector pCMV-VEE-GFP, Complete Sequence. GenBank ID: MH891622.1, 2019, 7 pages.
Extended European Search Report received for EP Application No. 21856761.8, mailed on May 14, 2024, 8 pages.
International Search Report and Written Opinion received for Application No. PCT/US2021/021572, mailed on Jul. 20, 2021, 11 pages.
International Search Report and Written Opinion received for Application No. PCT/US2021/021573, mailed on Jul. 1, 2021, 12 pages.
International Search Report and Written Opinion received for Application No. PCT/US2022/074337, mailed on Dec. 30, 2022, 16 pages.
International Search Report and Written Opinion received for Application No. PCT/US2021/045866, mailed on Dec. 6, 2021, 9 pages.
Wu, F.; Zhao, S.; Yu, B.; Chen, Y.M.; Wang, W.; Song, Z.G.; Hu, Y.; Tao, Z.W.; Tian, J.H.; Pei, Y.Y.; Yuan, M.L.; Zhang, Y.L.; Dai, F.H.; Liu, Y.; Wang, Q.M.; Zheng, J.J.; Xu, L.; Holmes, E.C.; Zhang, Y.Z. Surface Glycoprotein [Severe Acute Respiratory Syndrome Coronavirus 2].NCBI Reference Sequence: : YP_009724390.1, 2020, 3 pages.
Altschul, S.F.; Gish, W.; Miller, W.; Myers, E.W.; Lipman, D.J. Basic Local Alignment Search Tool. *J. Mol. Biol. 1990, 215* (3), 403-410.
Altschul, S.F.; Madden, T.L.; Schaffer, A.A.; Zhang, J.; Zhang, Z.; Miller, W.; Lipman, D.J. Gapped BLAST and PSI-BLAST: a New Generation of Protein Database Search Programs. *Nucleic Acids Res. 1997, 25* (17), 3389-3402.
Baden, L.R.; El Sahly, H.M.; Essink, B.; Kotloff, K.; Frey, S.; Novak, R.; Diemert, D.; Spector, S.A.; Rouphael, N.; Creech, C.B.; McGettigan, J.; Khetan, S.; Segall, N.; Solis, J.; Brosz, A.; Fierro, C.; Schwartz, H.; Neuzil, K.; Corey, L.; Gilbert, P.; Janes, H.; Follmann, D.; Marovich, M.; Mascola, J.; Polakowski, L.; Ledgerwood, J.; Graham, B.S.; Bennett, H.; Pajon, R.; Knightly, C.; Leav, B.; Deng, W.; Zhou, H.; Han, S.; Ivarsson, M.; Miller, J.; Zaks, T.; COVE Study Group. Efficacy and Safety of the mRNA-1273 SARS-COV-2 Vaccine. *N. Engl. J. Med. 2021, 384* (5), 403-416.
Boles, K.S.; Kannan, K.; Gill, J.; Felderman, M.; Gouvis, H.; Hubby, B.; Kamrud, K.I.; Venter, J.C.; Gibson, D.G. Synthetic Construct H7N9 HA Gene, Complete CDS. *National Library of Medicine*. GenBank: KY199425.1, 2017, 4 pages.
Both, G.W.; Banerjee, A.K.; Shatkin, A.J. Methylation-Dependent Translation of Viral Messenger RNAs In Vitro. *Proc. Natl. Acad. Sci. U.S.A. 1975, 72* (3), 1189-1193.
Bouloy, M.; Plotch, S.J.; Krug, R.M. Both the 7-Methyl and the 2'-O-Methyl Groups in the Cap of mRNA Strongly Influence its Ability to Act as Primer for Influenza Virus RNA Transcription. *Proc. Natl. Acad. Sci. U.S.A. 1980, 77* (7), 3952-3956.
Chan, K.R.; Wang, X.; Saron, W.A.A.; Gan, E.S.; Tan, H.C.; Mok, D.Z.L.; Zhang, S.L.; Lee, Y.H.; Liang, C.; Wijaya, L.; Ghosh, S.; Cheung, Y.B.; Tannenbaum, S.R.; Abraham, S.N.; St John, A.L.; Low, J.G.H.; Ooi, E.E. Cross-reactive Antibodies Enhance Live Attenuated Virus Infection for Increased Immunogenicity. *Nat. Microbiol.* 2016, 1 (12), 16164 (10 pages).
Chan, C.Y.Y.; Chan, K.R.; Chua, C.J.; Nur Hazirah, S.; Ghosh, S.; Ooi, E.E.; Low, J.G. Early Molecular Correlates of Adverse Events Following Yellow Fever Vaccination. *JCI Insight. 2017, 2* (19), e96031 (12 pages).
Chan, K.R.; Gan, E.S.; Chan, C.Y.Y.; Liang, C.; Low, J.Z.H.; Zhang, S.L.; Ong, E.Z.; Bhatta, A.; Wijaya, L.; Lee, Y.H.; Low, J.G.; Ooi, E.E. Metabolic Perturbations and Cellular Stress Underpin Susceptibility to Symptomatic Live-attenuated Yellow Fever Infection. *Nat. Med. 2019, 25* (8), 1218-1224 (21 pages).
Chu, L.Y.; Lockard, R.E.; RajBhandary, U.L.; Rhoads, R.E. Paradoxical Observations on the 5' Terminus of Ovalbumin Messenger Ribonucleic Acid. *J. Biol. Chem. 1978, 253* (15), 5228-5231.
Cirelli, K.M.; Carnathan, D.G.; Nogal, B.; Martin, J.T.; Rodriguez, O.L.; Upadhyay, A.A.; Enemuo, C.A.; Gebru, E.H.; Choe, Y.; Viviano, F.; Nakao, C.; Pauthner, M.G.; Reiss, S.; Cottrell, C.A.; Smith, M.L.; Bastidas, R.; Gibson, W.; Wolabaugh, A.N.; Melo, M.B.; Cossette, B.; Kumar, V.; Patel, N.B.; Tokatlian, T.; Menis, S.; Kulp, D.W.; Burton, D.R.; Murrell, B.; Schief, W.R.; Bosinger, S.E.; Ward, A.B.; Watson, C.T.; Silvestri, G.; Irvine, D.J.; Crotty, S. Slow Delivery Immunization Enhances HIV Neutralizing Antibody and Germinal Center Responses via Modulation of Immunodominance. *Cell 2019, 177* (5), 1153-1171.e28 (57 pages).
Conticello, S.G.; Ganesh, K.; Xue, K.; Lu, M.; Rada, C. Interaction Between Antibody-diversification Enzyme Aid and Spliceosome-associated Factor CTNNBL1. *Mol. Cell. 2008, 31*(4):474-484.

(56) References Cited

OTHER PUBLICATIONS

Corbett, K.S.; Edwards, D.K.; Leist, S.R.; Abiona, O.M.; Boyoglu-Barnum, S.; Gillespie, R.A.; Himansu, S.; Schäfer, A.; Ziwawo, C.T.; DiPiazza, A.T.; Dinnon, K.H.; Elbashir, S.M.; Shaw, C.A.; Woods, A.; Fritch, E.J.; Martinez, D.R.; Bock, K.W.; Minai, M.; Nagata, B.M.; Hutchinson, G.B.; Wu, K.; Henry, C.; Bahl, K.; Garcia-Dominguez, D.; Ma, L.; Renzi, I.; Kong, W.P.; Schmidt, S.D.; Wang, L.; Zhang, Y.; Phung, E.; Chang, L.A.; Loomis, R.J.; Altaras, N.E.; Narayanan, E.; Metkar, M.; Presnyak, V.; Liu, C.; Louder, M.K.; Shi, W.; Leung, K.; Yang, E.S.; West, A.; Gully, K.L.; Stevens, L.J.; Wang, N.; Wrapp, D.; Doria-Rose, N.A.; Stewart-Jones, G.; Bennett, H.; Alvarado, G.S.; Nason, M.C.; Ruckwardt, T.J.; McLellan, J.S.; Denison, M.R.; Chappell, J.D.; Moore, I.N.; Morabito, K.M.; Mascola, J.R.; Baric, R.S.; Carfi, A.; Graham, B.S. SARS-CoV-2 mRNA Vaccine Design Enabled by Prototype Pathogen Preparedness. *Nature 2020, 586*, 567-571.

Corbett, K.S.; Edwards, D.; Leist, S.R.; Abiona, O.M.; Boyoglu-Barnum, S.; Gillespie, R.A.; Himansu, S.; Schäfer, A.; Ziwawo, C.T.; DiPiazza, A.T.; Dinnon, K.H.; Elbashir, S.M.; Shaw, C.A.; Woods, A.; Fritch, E.J.; Martinez, D.R.; Bock, K.W.; Minai, M.; Nagata, B.M.; Hutchinson, G.B.; Bahl, K.; Garcia-Dominguez, D.; Ma, L.; Renzi, I.; Kong, W.P.; Schmidt, S.D.; Wang, L.; Zhang, Y.; Stevens, L.J.; Phung, E.; Chang, L.A.; Loomis, R.J.; Altaras, N.E.; Narayanan, E.; Metkar, M.; Presnyak, V.; Liu, C.; Louder, M.K.; Shi, W.; Leung, K.; Yang, E.S.; West, A.; Gully, K.L.; Wang, N.; Wrapp, D.; Doria-Rose, N.A.; Stewart-Jones, G.; Bennett, H.; Nason, M.C.; Ruckwardt, T.J.; McLellan, J.S.; Denison, M.R.; Chappell, J.D.; Moore, I.N.; Morabito, K.M.; Mascola, J.R.; Baric, R.S.; Carfi, A.; Graham, B.S. Sars-CoV-2 mRNA Vaccine Development Enabled by Prototype Pathogen Preparedness. bioRxiv 2020, 39 pages.

Dua, J.S.; Rana, Prof. A.C.; Bhandari, Dr. A.K. Liposome: Methods of Preparation and Applications.*Int. J. Pharm. Sci. Res. 2012, 3* (3), 14-20.

Dupuis, M.; Denis-Mize, K.; Woo, C.; Goldbeck, C.; Selby, M.J.; Chen, M.; Otten, G.R.; Ulmer, J.B.; Donnelly, J.J.; Ott, G.; McDonald, D.M. Distribution of DNA Vaccines Determines Their Immunogenicity After Intramuscular Injection in Mice. *J. Immunol. 2000, 165* (5), 2850-2858.

Ehrchen, J.M.; Sunderkötter, C.; Foell, D.; Vogl, T.; Roth, J. The Endogenous Toll-like Receptor 4 Agonist S100A8/S100A9 (Calprotectin) as Innate Amplifier of Infection, Autoimmunity, and Cancer. *J. Leukoc. Biol. 2009, 86* (3), 557-566.

Geall, A.J.; Verma, A.; Otten, G.R.; Shaw, C.A.; Hekele, A.; Banerjee, K.; Cu, Y.; Beard, C. W.; Brito, L.A.; Krucker, T.; O'Hagan, D.T.; Singh, M.; Mason, P.W.; Valiante, N.M.; Dormitzer, P.R.; Barnett, S.W.; Rappuoli, R.; Ulmer, J.B.; Mandl, C.W. Nonviral Delivery of Self-amplifying RNA Vaccines. *Proc. Natl. Acad. Sci. U.S.A. 2012, 109* (36), 14604-14609.

Groom, J.R.; Luster, A.D. CXCR3 in T Cell Function. *Exp. Cell Res. 2011, 317* (5), 620-631 (21 pages).

Gustafsson, C.; Govindarajan, S.; Minshull, J. Codon Bias and Heterologous Protein Expression. *Trends Biotechnol. 2004, 22* (7), 346-353.

Hashem, A.M.; Algaissi, A.; Agrawal, A.S.; Al-Amri, S.S.; Alhabbab, R.Y.; Sohrab, S.S.; Almasoud, S.A.; Alharbi, N.K.; Peng, B.H.; Russell, M.; Li, X.; Tseng, C.K. A Highly Immunogenic, Protective, and Safe Adenovirus-Based Vaccine Expressing Middle East Respiratory Syndrome Coronavirus S1-CD40L Fusion Protein in a Transgenic Human Dipeptidyl Peptidase 4 Mouse Model. *J. Infect. Dis. 2019, 220* (10), 1558-1567.

Hassett, K.J.; Benenato, K.E.; Jacquinet, E.; Lee, A.; Woods, A.; Yuzhakov, O.; Himansu, S.; Deterling, J.; Geilich, B.M.; Ketova, T.; Mihai, C.; Lynn, A.; McFadyen, I.; Moore, M.J.; Senn, J.J.; Stanton, M.G.; Almarsson, Ö.; Ciaramella, G.; Brito, L.A. Optimization of Lipid Nanoparticles for Intramuscular Administration of mRNA Vaccines. Mol. Ther. Nucleic Acids. 2019, 15, 1-11.

Higgins, B.W.; McHeyzer-Williams, L.J.; McHeyzer-Williams, M.G. Programming Isotype-specific Plasma Cell Function. *Trends Immunol. 2019, 40* (4), 345-357.

Honda-Okubo, Y.; Barnard, D.; Ong, C.H.; Peng, B.H.; Tseng, C.K.; Petrovsky, N. Severe Acute Respiratory Syndrome-associated Coronavirus Vaccines Formulated with Delta Inulin Adjuvants Provide Enhanced Protection While Ameliorating Lung Eosinophilic Immunopathology. *J. Virol. 2015, 89* (6), 2995-3007.

Hsieh, C.L.; Goldsmith, J.A.; Schaub, J.M.; DiVenere, A.M.; Kuo, H.C.; Javanmardi, K.; Le, K.C.; Wrapp, D.; Lee, A.G.; Liu, Y.; Chou, C.W.; Byrne, P.O.; Hjorth, C.K.; Johnson, N.V.; Ludes-Meyers, J.; Nguyen, A.W.; Park, J.; Wang, N.; Amengor, D.; Lavinder, J.J.; Ippolito, G.C.; Maynard, J.A.; Finkelstein, I.J.; McLellan, U.S. Structure-based Design of Prefusion-stabilized SARS-COV-2 spikes. *Science 2020, 369* (6510), 1501-1505 (10 pages).

Hyde, J.L.; Chen, R.; Trobaugh, D.W.; Diamond, M.S.; Weaver, S.C.; Klimstra, W.B.; Wilusz, J. The 5' and 3' Ends of Alphavirus RNAs—Non-coding is not Non-functional. *Virus Res*. 2015, 206, 99-107 (8 pages).

Ishikawa, M.; Murai, R.; Hagiwara, H.; Hoshino, T.; Suyama, K. Preparation of Eukaryotic mRNA having Differently Methylated Adenosine at the 5'-Terminus and the Effect of the Methyl Group in Translation. *Nucleic Acids Symp. Ser. (Oxf). 2009, 53* (1), 129-130.

Jackson, N.A.C.; Kester, K.E.; Casimiro, D.; Gurunathan, S.; DeRosa, F. The Promise of mRNA Vaccines: a Biotech and Industrial Perspective. *NPJ Vaccines 2020, 5*(11), 1-6. (6 pages).

Jin, B.; Sun, T.; Yu, X.H.; Liu, C.Q.; Yang, Y.X.; Lu, P.; Fu, S.F.; Qiu, H.B.; Yeo, A.E. Immunomodulatory Effects of dsRNA and Its Potential as Vaccine Adjuvant. *J. Biomed. Biotechnol. 2010, 2010*, Article ID 690438, 1-17.

Kalnin, K.V.; Plitnik, T.; Kishko, M.; Zhang, J.; Zhang, D.; Beauvais, A.; Anosova, N.G.; Tibbitts, T.; DiNapoli, J.; Ulinski, G.; Piepenhagen, P.; Cummings, S.M.; Bangari, D.S.; Ryan, S.; Huang, P.D.; Huleatt, J.; Vincent, D.; Fries, K.; Karve, S.; Goldman, R.; Gopani, H.; Dias, A.; Tran, K.; Zacharia, M.; Gu, X.; Boeglin, L.; Abysalh, J.; Vargas, J.; Beaulieu, A.; Shah, M.; Jeannotte, T.; Gillis, K.; Chivukula, S.; Swearingen, R.; Landolfi, V.; Fu, T.M.; DeRosa, F.; Casimiro, D. Immunogenicity and Efficacy of mRNA COVID-19 Vaccine MRT5500 in Preclinical Animal Models. *NPJ Vaccines 2021, 6* (61), 1-12.

Karlin, S.; Altschul, S.F. Applications and Statistics for Multiple High-Scoring Segments in Molecular Sequences. *Proc. Natl. Acad. Sci. U.S.A. 1993, 90* (12), 5873-5877.

Karlin, S.; Altschul, S.F. Methods for Assessing the Statistical Significance of Molecular Sequence Features by Using General Scoring Schemes. *Proc. Natl. Acad. Sci. U.S.A. 1990, 87* (6), 2264-2268.

Kasturi, S.P.; Skountzou, I.; Albrecht, R.A.; Koutsonanos, D.; Hua, T.; Nakaya, H.; Ravindran, R.; Stewart, S.; Alam, M.; Kwissa, M.; Villinger, F.; Murthy, N.; Steel, J.; Jacob, J.; Hogan, R.J.; Garcia-Sastre, A.; Compans, R.; Pulendran, B. Programming the Magnitude and Persistence of Antibody Responses with Innate Immunity. *Nature 2011, 470* (7335), 543-547 (20 pages).

Keech, C.; Albert, G.; Cho, I.; Robertson, A.; Reed, P.; Neal, S.; Plested, J.S.; Zhu, M.; Cloney-Clark, S.; Zhou, H.; Smith, G.; Patel, N.; Frieman, M.B.; Haupt, R.E.; Logue, J.; McGrath, M.; Weston, S.; Piedra, P.A.; Desai, C.; Callahan, K.; Lewis, M.; Price-Abbott, P.; Formica, N.; Shinde, V.; Fries, L.; Lickliter, J.D.; Griffin, P.; Wilkinson, B.; Glenn, G.M. Phase 1-2 Trial of a SARS-CoV-2 Recombinant Spike Protein Nanoparticle Vaccine. *N. Engl. J. Med. 2020, 383*, 2320-2332.

Kirchdoerfer, R.N.; Wang, N.; Pallesen, J.; Wrapp, D.; Turner, H.L.; Cottrell, C.A.; Corbett, K.S.; Graham, B.S.; McLellan, J.S.; Ward, A.B. Stabilized Coronavirus Spikes Are Resistant to Conformational Changes Induced by Receptor Recognition or Proteolysis. *Sci. Rep. 2018, 8* (1), 15701 (11 pages).

Kowalski, P.S.; Rudra, A.; Miao, L.; Anderson, D.G. Delivering the Messenger: Advances in Technologies for Therapeutic mRNA Delivery. *Mol. Ther. 2019, 27* (4), 710-728.

Kozak, M. Downstream Secondary Structure Facilitates Recognition of Initiator Codons by Eukaryotic Ribosomes. *Proc. Natl. Acad. Sci. U.S.A. 1990, 87* (21), 8301-8305.

Kozak, M. Leader Length and Secondary Structure Modulate mRNA Function under Conditions of Stress. *Mol. Cell. Biol. 1988, 8* (7), 2737-2744.

(56) References Cited

OTHER PUBLICATIONS

Kozak, M. Structural Features in Eukaryotic mRNAs that Modulate the Initiation of Translation. *J. Biol. Chem.* 1991, 266 (30), 19867-19870.

Kozak, M. The Scanning Model for Translation: An Update. *J. Cell. Biol.* 1989, 108 (2), 229-241.

Kreiter, S.; Selmi, A.; Diken, M.; Sebastian, M.; Osterloh, P.; Schild, H.; Huber, C.; Türeci, O .; Sahin, U. Increased Antigen Presentation Efficiency by Coupling Antigens to MHC Class I Trafficking Signals. *J. Immunol.* 2008, 180 (1), 309-318.

Kulasegaran-Shylini, R.; Thiviyanathan, V.; Gorenstein, D.G.; Frolov, I. The 5'UTR-Specific Mutation in Veev TC-83 Genome has a Strong Effect on RNA Replication and Subgenomic RNA Synthesis, but not on Translation of the Encoded Proteins. *Virology* 2009, 387 (1), 211-221.

Kulkarni, J.A.; Cullis, P.R.; Van der Meel, R. Lipid Nanoparticles Enabling Gene Therapies: From Concepts to Clinical Utility. *Nucleic Acid Ther.* 2018, 28 (3), 146-157.

Li, X.; Xu, H.; Chen, Z.; Chen, G. Biosynthesis of Nanoparticles by Microorganisms and Their Applications. *J. Nanomater.* 2011, 2011, Article ID 270974, 1-16.

Magini, D.; Giovani, C.; Mangiavacchi, S.; Maccari, S.; Cecchi, R.; Ulmer, J.B.; De Gregorio, E.; Geall, A.J.; Brazzoli, M.; Bertholet, S. Self-Amplifying mRNA Vaccines Expressing Multiple Conserved Influenza Antigens Confer Protection Against Homologous and Heterosubtypic Viral Challenge. *PLoS One* 2016, 11 (8), e0161193, 1-25.

Maruggi, G.; Shaw, C.A.; Otten, G.R.; Mason, P.W.; Beard, C.W. Engineered Alphavirus Replicon Vaccines Based on Known Attenuated Viral Mutants Show Limited Effects on Immunogenicity. *Virol.* 2013, 447 (1-2), 254-264.

Maruggi, G.; Zhang, C.; Li, J.; Ulmer, J.B.; Yu, D. mRNA as a Transformative Technology for Vaccine Development to Control Infectious Diseases, *Mol. Ther.* 2019, 27 (4), 757-772.

Muthukrishnan, S.; Both G.W.; Furuichi, Y.; Shatkin, A.J. 5'-Terminal 7-Methylguanosine in Eukaryotic mRNA is Required for Translation. *Nature* 1975, 255 (5503), 33-37.

Olmedillas, E.; Mann, C.J.; Peng, W.; Wang, Y.; Avalos, R.D.; Bedinger, D.; Valentine, K.; Shafee, N.; Schendel, S.L.; Yuan, M.; Lang, G.; Rouet, R.; Christ, D.; Jian, W.; Wilson, I.A.; Germann, T.; Shresta, S.; Snijder, J.; Saphire, E.O. Structure-Based Design of a Highly Stable, Covalently-Linked SARS-CoV-2 Spike Trimer with Improved Structural Properties and Immunogenicity. *bioRxiv 2021*, 51 pages.

Patil, Y.P.; Jadhav, S. Novel Methods for Liposome Preparation. *Chem. Phys. Lipids* 2014, 177, 8-18.

Pearson, W.R.; Lipman, D.J. Improved Tools for Biological Sequence Comparison. *Proc. Natl. Acad. Sci. U.S.A.* 1988, 85 (8), 2444-2448.

Pepini, T.; Pulichino, A.M.; Carsillo, T.; Carlson, A.L.; Sari-Sarraf, F.; Ramsauer, K.; Debasitis, J.C.; Maruggi, G.; Otten, G.R.; Geall, A.J.; Yu, D.; Ulmer, J.B.; Iavarone, C. Induction of an IFN-mediated Antiviral Response by a Self-amplifying RNA Vaccine: Implications for Vaccine Design. *J. Immunol.* 2017, 198 (10), 4012-4024.

Petkov, S.; Starodubova, E.; Latanova, A.; Kilpelainen, A.; Latyshev, O.; Svirskis, S.; Wahren, B.; Chiodi, F.; Gordeychuk, I.; Isaguliants, M. DNA Immunization Site Determines the Level of Gene Expression and the Magnitude, but not the Type of the Induced Immune Response, *PLoS One* 2018, 13 (6), e0197902, 1-22.

Polack, F.P.; Thomas, S.J.; Kitchin, N.; Absalon, J.; Gurtman, A.; Lockhart, S.; Perez, J.L.; Perez Marc, G.; Moreira, E.D.; Zerbini, C.; Bailey, R.; Swanson, K.A.; Roychoudhury, S.; Koury, K.; Li, P.; Kalina, W.V.; Cooper, D.; Frenck, Jr. R.W.; Hammitt, L.L.; Türeci, Ö.; Nell, H.; Schaefer, A.; Ünal, S.; Tresnan, D.V.M.; Mather, S.; Dormitzer, P.R.; Şahin, U.; Jansen, K.U.; Gruber, W.C.; C4591001 Clinical Trial Group. Safety and Efficacy of the BNT162b2 mRNA Covid-19 Vaccine. *N. Engl. J. Med.* 2020, 383, 2603-2615.

Querec, T.D.; Akondy, R.S.; Lee, E.K.; Cao, W.; Nakaya, H.I.; Teuwen, D.; Pirani, A.; Gernert, K.; Deng, J.; Marzolf, B.; Kennedy, K.; Wu, H.; Bennouna, S.; Oluoch, H.; Miller, J.; Vencio, R.Z.; Mulligan, M.; Aderem, A.; Ahmed, R.; Pulendran, B. Systems Biology Approach Predicts Immunogenicity of the Yellow Fever Vaccine in Humans. *Nat. Immunol.* 2009, 10 (1), 116-125.

Querec T.D.; Pulendran B. Understanding the Role of Innate Immunity in the Mechanism of Action of the Live Attenuated Yellow Fever Vaccine 17D. *Adv. Exp. Med. Biol.* 2007, 590, 43-53.

Ramanathan, A.; Robb, G.B.; Chan, S. mRNA Capping: Biological Functions and Applications. *Nucleic Acids Res.* 2016, 44 (16), 7511-7526.

Rodríguez-Gascón, A.; Del Pozo-Rodríguez, A.; Solinis, M.Á. Development of Nucleic Acid Vaccines: Use of Self-Amplifying RNA in Lipid Nanoparticles. *Int. J. Nanomedicine* 2014, 9, 1833-1843.

Sahin, U.; Muik, A.; Vogler, I.; Derhovanessian, E.; Kranz, L.M.; Vormehr, M.; Quandt, J.; Bidmon, N.; Ulges, A.; Baum, A.; Pascal, K.; Maurus, D.; Brachtendorf, S.; Lörks, V.; Sikorski, J.; Koch, P.; Hilker, R.; Becker, D.; Eller, A.; Grützner, J.; Tonigold, M.; Boesler, C.; Rosenbaum, C.; Heesen, L.; Kühnle, M.; Poran, A.; Dong, J.Z.; Luxemburger, U.; Kemmer-Bruck, A.; Langer, D.; Bexon, M.; Bolte, S.; Palanche, T.; Schultz, A.; Baumann, S.; Mahiny, A.J.; Boros, G.; Reinholz, J.; Szabó, G.T.; Karikó,K.; Shi, P.; Fontes-Garfias, C.; Perez, J.L.; Cutler, M.; Cooper, D.; Kyratsous, C.A.; Dormitzer, P.R.; Jansen, K.U.; Türeci, Ö. BNT162b2 Induces SARS-CoV-2-Neutralising Antibodies and T cells in Humans. *medRxiv 2020*, 49 pages.

Sahin, U.; Muik, A.; Vogler, I.; Derhovanessian, E.; Kranz, L.M.; Vormehr, M.; Quandt, J.; Bidmon, N.; Ulges, A.; Baum, A.; Pascal, K.E.; Maurus, D.; Brachtendorf, S.; Lörks, V.; Sikorski, J.; Koch, P.; Hilker, R.; Becker, D.; Eller, A.; Grützner, J.; Tonigold, M.; Boesler, C.; Rosenbaum, C.; Heesen, L.; Kühnle, M.; Poran, A.; Dong, J.Z.; Luxemburger, U.; Kemmer-Bruck, A.; Langer, D.; Bexon, M.; Bolte, S.; Palanche, T.; Schultz, A.; Baumann, S.; Mahiny, A.J.; Boros, G.; Reinholz, J.; Szabó, G.T.; Karikó,K.; Shi, P.; Fontes-Garfias, C.; Perez, J.L.; Cutler, M.; Cooper, D.; Kyratsous, C.A.; Dormitzer, P.R.; Jansen, K.U.; Türeci, Ö. BNT162b2 Vaccine Induces Neutralizing Antibodies and Poly-Specific T Cells in Humans. *Nature* 2021, 595, 572-577.

Salti, S.M.; Hammelev, E.M.; Grewal, J.L.; Reddy, S.T.; Zemple, S.; Grossman, W.J.; Grayson, M.H.; Verbsky, J.W. Granzyme B Regulates Antiviral CD8+ T Cell Responses. *J. Immunol.* 2011, 187 (12), 6301-6309.

Slansky, J.E.; Rattis, F.M.; Boyd, L.F.; Fahmy, T.; Jaffee, E.M.; Schneck, J.P.; Margulies, D.H.; Pardoll, D.M. Enhanced Antigen-Specific Antitumor Immunity with Altered Peptide Ligands that Stabilize the MHC-Peptide-TCR Complex. *Immunity* 2000, 13, 529-538.

Tam, H.H.; Melo, M.B.; Kang, M.; Pelet, J.M.; Ruda, V.M.; Foley, M.H.; Hu, J.K.; Kumari, S.; Crampton, J.; Baldeon, A.D.; Sanders, R.W.; Moore, J.P.; Crotty, S.; Langer, R.; Anderson, D.G.; Chakraborty, A.K.; Irvine, D.J. Sustained Antigen Availability During Germinal Center Initiation Enhances Antibody Responses to Vaccination. *Proc. Natl. Acad. Sci. U.S.A.* 2016, 113, E6639-E6648.

Taverniti, V.; Seraphin, B. Elimination of Cap Structures Generated by mRNA Decay Involves the New Scavenger mRNA Decapping Enzyme Aph1/FHIT Together with DcpS. *Nucleic Acids Res.* 2015, 43 (1), 482-492.

Thompson, J.M.; Whitmore, A.C.; Konopka, J.L.; Collier, M.L.; Richmond, E.M.B.; Davis, N.L.; Staats, H.F.; Johnston, R.E. Mucosal and Systemic Adjuvant Activity of Alphavirus Replicon Particles. *Proc. Natl. Acad. Sci. U.S.A.* 2006, 103 (10), 3722-3727.

Villalobos, A.; Ness, J.E.; Gustafsson, C.; Minshull, J.; Govindarajan, S. Gene Designer: A Synthetic Biology Tool for Constructing Artificial DNA Segments. *BMC Bioinformatics* 2006, 7, Article No. 285, 8 pages.

Von Herrath, M.G.; Bot, A. Immune Responsiveness, Tolerance and dsRNA: Implications for Traditional Paradigms. *Trends Immunol.*, 2003, 24 (6), 289-293.

Wootton, J.C.; Federhen, S. Statistics of Local Complexity in Amino Acid Sequences and Sequence Databases. *Computers Chem.* 1993, 17 (2), 149-163.

Wrapp, D.; Wang, N.; Corbett, K.S.; Goldsmith, J.A.; Hsieh, C.; Abiona, O.; Graham, B.S.; Mclellan, U.S. Cryo-EM Structure of the 2019-nCoV Spike in the Prefusion Conformation. *Science* 2020, 367, 1260-1263.

(56) References Cited

OTHER PUBLICATIONS

Wu, F.; Zhao, S.; Yu, B.; Chen, Y.; Wang, W.; Song, Z.; Hu, Y.; Tao, Z.; Tian, J.; Pei, Y.; Yuan, M.; Zhang, Y.; Dai, F.; Liu, Y.; Wang, Q.; Zheng, J.; Xu, L.; Holmes, E.C.; Zhang, Y. A New Coronavirus Associated with Human Respiratory Disease in China. *Nature* 2020, *579*, 265-269.

Yu, G.; Boone, T.; Delaney J.; Hawkins, N.; Kelley, M.; Ramakrishnan, M.; McCabe, S.; Qiu, W.; Kornuc, M.; Xia, Z.; Guo J.; Stolina, M.; Boyle, J.W.; Sarosi, I.; Hsu, H.; Senaldi, G.; Theill, E.L. April and TALL-I and Receptors BCMA and TACI: System for Regulating Humoral Immunity. *Nat. Immunol.* 2000, *1* (3), 252-256.

Sercombe, L.; Veerati, T.; Moheimani, F.; Wu, S.Y.; Sood, A.K.; Hua, S. Advances and Challenges of Liposome Assisted Drug Delivery. *Front. Pharmacol.* 2015, *6* (286), 13 pages.

Love, K.T.; Mahon, K.P.; Levins, C.G.; Whitehead, K.A.; Querbes, W.; Dorkin, J.R.; Qin, J.; Cantley, W.; Qin, L.L.; Racie, T.; Frank-Kamenetsky, M.; Yip, K.N.; Alvarez, R.; Sah, D.W.Y.; De Fougerolles, A.; Fitzgerald, K.; Koteliansky, V.; Akinc, A.; Langer, R.; Anderson, D.G. Lipid-Like Materials for Low-Dose, in Vivo Gene Silencing. *Proc. Natl. Acad. Sci.* 2010, *107* (5), 1864-1869.

Lin, Q.; Chen, J.; Zhang, Z.; Zheng, G. Lipid-Based Nanoparticles in the Systemic Delivery of siRNA. *Nanomedicine* 2014, *9* (1), 105-120.

Lasic, D.D. Novel Applications of Liposomes. *Trends Biotechnol.* 1998, *16* (7), 307-321.

Li, S.; Huang, L. Stealth Nanoparticles: High Density but Sheddable PEG is a Key for Tumor Targeting. *J. Control Release* 2010, *145*, 178-181.

Kawabata, K.; Takakura, Y.; Hashida, M. The Fate of Plasmid DNA after Intravenous Injection in Mice: Involvement of Scavenger Receptors in its Hepatic Uptake. *Pharm. Res.* 1995, *12* (6), 825-830.

Jokerst, J.V.; Lobovkina, T.; Zare, R.N.; Gambhir, S.S. Nanoparticle PEGylation for Imaging and Therapy. *Nanomedicine* 2011, *6* (4), 715-728.

Huang, L.; Liu, Y. In Vivo Delivery of RNAi with Lipid-Based Nanoparticles. *Annu. Rev. Biomed. Eng.* 2011, *13*, 507-530.

Dabkowska, A.P.; Barlow, D.J.; Hughes, A.V.; Campbell, R.A.; Quinn, P.J.; Lawrence, M.J. The Effect of Neutral Helper Lipids on the Structure of Cationic Lipid Monolayers. *J. R. Soc. Interface* 2012, *9* (68), 548-561.

Bochicchio, S.; Dalmoro, A.; Barba, A.A.; Grassi, G.; Lamberti, G. Liposomes as siRNA Delivery Vectors, *Curr. Drug. Metab.* 2014, *15* (9), 882-892.

\* cited by examiner

METHOD OF LYOPHILIZING LIPID NANOPARTICLES

CROSS-REFERENCE TO RELATED APPLICATIONS

This application claims the benefit of priority to U.S. Provisional Application No. 63/066,051 filed on Aug. 14, 2020 and U.S. Provisional Application No. 63/158,761, filed on Mar. 9, 2021, the contents of which are incorporated by reference herein.

BACKGROUND

Field

The present disclosure relates to the field of pharmaceutical manufacturing and products. More specifically, the disclosure relates to lipid nanoparticle encapsulated nucleic acid compositions and methods for preparing lyophilized lipid nanoparticle nucleic acid product.

Background

Therapies based on the intracellular delivery of nucleic acids to target cells face both extracellular and intracellular barriers. Indeed, it is difficult to systemically administer naked nucleic acid materials due to their toxicity, low stability in serum, rapid renal clearance, reduced uptake by target cells, phagocyte uptake and their propensity to elicit an immune response, all features that preclude their clinical development. When exogenous nucleic acid material enters the human biological system, it is recognized by the reticuloendothelial system (RES) as foreign pathogens and cleared from blood circulation before having the chance to encounter target cells within or outside the vascular system. It has been reported that the half-life of naked nucleic acid in the blood stream is around several minutes (Kawabata K, Takakura Y, Hashida MPharm Res. 1995 June; 12(6):825-30). Chemical modification and a proper delivery method can reduce uptake by the RES and protect nucleic acids from degradation by ubiquitous nucleases, which increase stability and efficacy of nucleic acid-based therapies. In addition, ribonucleic acids (RNAs) or deoxyribonucleic acid (DNAs) are anionic hydrophilic polymers that are not favorable for uptake by cells, which are also anionic at the surface. The success of nucleic acid-based therapies thus depends largely on the development of vehicles or vectors that can efficiently and effectively deliver genetic material to target cells and obtain sufficient levels of expression in vivo with minimal toxicity.

While several gene therapies have been able to successfully utilize a viral delivery vector (e.g., adeno-associated virus (AAV)), lipid-based formulations have been increasingly recognized as one of the most promising delivery systems for RNA and other nucleic acid compounds due to their biocompatibility and their ease of large-scale production. One of the most significant advances in lipid-based nucleic acid therapies happened in August 2018 when Patisiran (ALN-TTR02) was the first small-interfering RNA (siRNA) therapeutic approved by the Food and Drug Administration (FDA) and by the European Commission (EC). ALN-TTR02 is an siRNA formulation based upon the so-called Stable Nucleic Acid Lipid Particle (SNALP) transfecting technology. Despite the success of Patisiran, the delivery of nucleic acid therapeutics via lipid nanoparticles is still undergoing development.

Some art-recognized lipid-formulated delivery vehicles for nucleic acid therapeutics include polymer based carriers, such as polyethyleneimine (PEI), lipid nanoparticles and liposomes, nanoliposomes, ceramide-containing nanoliposomes, multivesicular liposomes, proteoliposomes, both natural and synthetically-derived exosomes, natural, synthetic and semi-synthetic lamellar bodies, nanoparticulates, micelles, and emulsions. Among these, lipid nanoparticles have shown great promise as a potential delivery vehicle for RNA therapeutics, however the use of lipid nanoparticles delivery technology faces problems with its stability, and in several instances requires that suspensions of the lipid nanoparticles be stored at impractically cold temperatures of about −70° C. and only be thawed shortly before intended administration. Such requirements can limit the development of medicines that can be used by patients in their own homes as well as in the transportation and storage of lipid nanoparticle therapeutics in remote and underdeveloped regions of the world, all of which lack the proper equipment for storage of lipid nanoparticles suspensions.

One solution for improving the storage capabilities of lipid nanoparticles formulations is to manufacture the lipid nanoparticle formulations as a lyophilized product that can be subsequently reconstituted prior to administration. Lyophilized lipid nanoparticle compositions can be stored at more practical temperatures, allowing more convenient modes of distribution and administration.

Although lyophilization technologies have existed for several decades, the application of these technologies does not translate well to lipid nano particles formulations, which lose several of their desired properties including low polydispersity, small particle size, high percentage of encapsulation, and in vivo efficacy upon reconstitution after conventional lyophilization techniques. Thus, new solutions are needed for providing lyophilized lipid nanoparticle compositions that show a maintained integrity and efficacy upon reconstitution.

SUMMARY

The present disclosure provides lyophilization methods that result in a preservation of lipid nanoparticle integrity, integrity of the encapsulated nucleic acid, the particle size of the lipid nanoparticles within an acceptable degree of prelyophilized particle size, and good polydispersity of the nanoparticles. The methods stem from the discovery that specialized excipients can be added to a pretreated suspension of the nanoparticles prior to subjecting the suspension to a lyophilization process. In addition, lyophilization parameters are employed in combination with these excipients to achieve high quality lyophilized lipid nanoparticle product. The lyophilized product is easily reconstituted and readily administered as a pharmaceutical preparation.

In some embodiments, a method of lyophilizing a composition comprising lipid nanoparticles encapsulating an RNA is provided comprising the steps of providing a suspension of the lipid nanoparticles in a liquid medium, adjusting the liquid medium thereby forming a pretreated suspension comprising at least one excipient selected from potassium sorbate, thiosulfate, sodium benzoate, and iodixanol; and subjecting the pretreated suspension to a lyophilization process.

In another embodiment, a lyophilized composition is provided comprising lipid nanoparticles encapsulating a nucleic acid and one or more excipients selected from potassium sorbate, thiosulfate, sodium benzoate, and iodixanol.

In another embodiments, a method of preserving a lyophilized composition of the disclosure is provided comprising storing the lyophilized product at a temperature of about −20° C. to about 8° C. In some embodiments, a method of preserving a lyophilized composition of the disclosure is provided comprising storing the lyophilized product at a temperature of about −20° C. to about 25° C. In some embodiments, the lyophilized product is stored at about −20° C. In some embodiments, the lyophilized product is stored from about 2° C. to about 8° C. In some embodiments, the lyophilized product is stored from about 20° C. to about 25° C.

In another embodiments, a method of reconstituting a lyophilized composition of the disclosure is provided comprising adding a liquid medium to the lyophilized composition.

In another embodiments, a method of treating a disease or disorder in a subject is provided comprising administering to the subject a lyophilized composition of the disclosure reconstituted in a liquid medium.

Additional features and advantages of the subject technology will be set forth in the description below, and in part will be apparent from the description, or may be learned by practice of the subject technology. The advantages of the subject technology will be realized and attained by the written description and embodiments hereof.

It is to be understood that both the foregoing general description and the following detailed description are exemplary and explanatory and are intended to provide further explanation of the subject technology.

DETAILED DESCRIPTION

Figure 1:
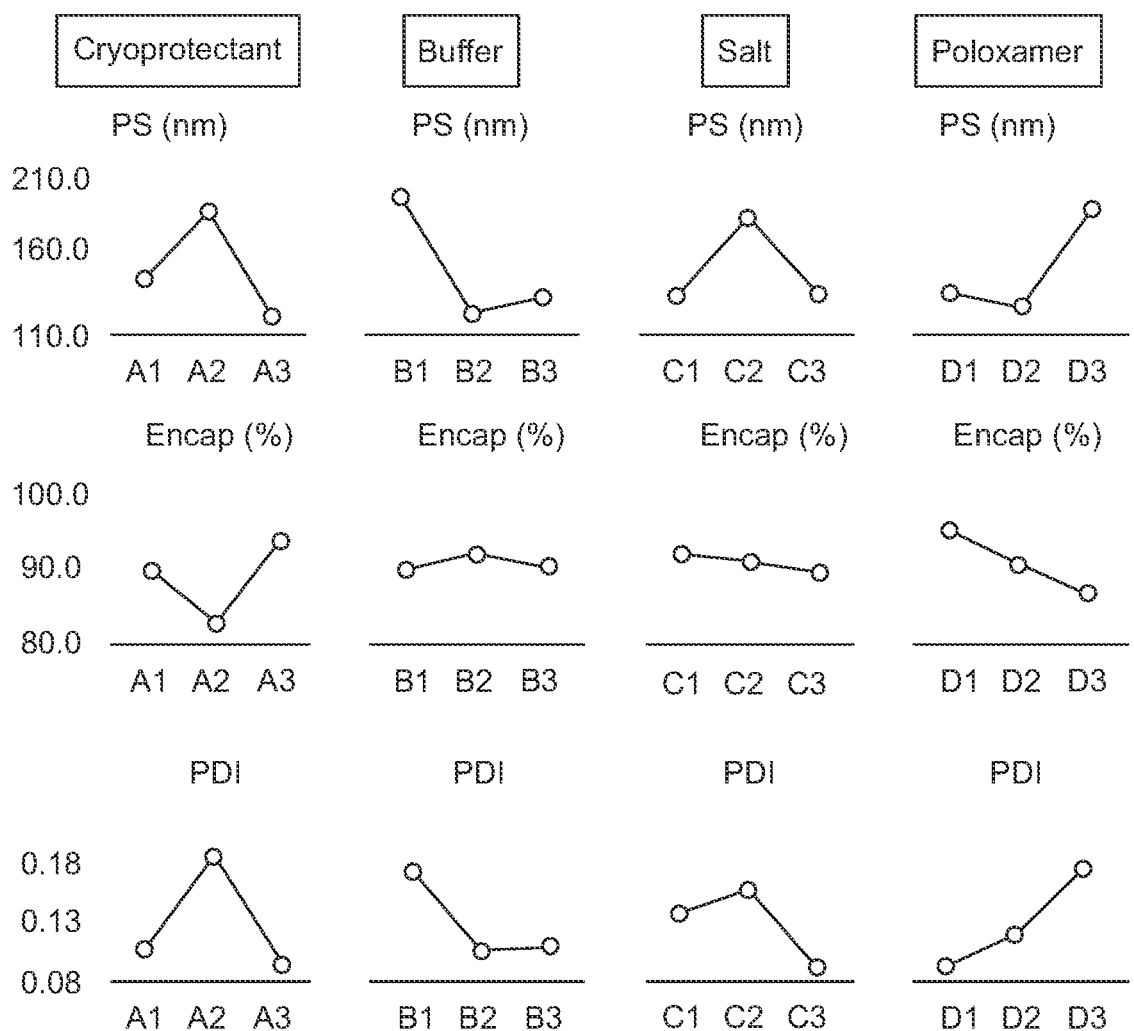
FIG. 1 shows the characterization (particle size, (PS) polydispersity (PDI), and percent encapsulation (Encap (%)) of reconstituted lipid nanoparticles prepared according to the experiments described in Example 3 for formulations prepared at a concentration of 1 mg RNA/mL.

It is understood that various configurations of the subject technology will become readily apparent to those skilled in the art from the disclosure, wherein various configurations of the subject technology are shown and described by way of illustration. As will be realized, the subject technology is capable of other and different configurations and its several details are capable of modification in various other respects, all without departing from the scope of the subject technology. Accordingly, the summary, figures and detailed description are to be regarded as illustrative in nature and not as restrictive.

The detailed description set forth below is intended as a description of various configurations of the subject technology and is not intended to represent the only configurations in which the subject technology may be practiced. The detailed description includes specific details for the purpose of providing a thorough understanding of the subject technology. However, it will be apparent to those skilled in the art that the subject technology may be practiced without these specific details In some embodiments, a method of lyophilizing a composition is provided comprising lipid nanoparticles encapsulating an RNA, the method comprising the steps of: a.) providing a suspension of the lipid nanoparticles in a liquid medium, wherein the liquid medium comprises about 4% w/v to about 22% w/v of a saccharide; and b.) adjusting the liquid medium thereby forming a pretreated suspension comprising at least one excipient selected from potassium sorbate, thiosulfate, sodium benzoate, and iodixanol.

In some embodiments, the method further comprises a step (c): subjecting the pretreated suspension to a lyophilization process comprising: i.) an initial freezing step conducted at a temperature of −48±8° C. and at atmospheric pressure; ii.) a primary drying step conducted at a temperature in the range of −20±2° C. to −48±2° C. and at a pressure in the range of about 25 mTorr to about 100 mTorr; and iii.) a secondary drying step conducted at a temperature in the range of 5±2° C. to 30±2° C. and at a pressure in the range of about 30 mTorr to about 300 mTorr.

In some embodiments, the method further comprises a step (c): subjecting the pretreated suspension to a lyophilization process comprising: i.) an initial freezing step conducted at a temperature of −48±8° C. and at atmospheric pressure; ii.) a primary drying step conducted at a pressure of about 0.03 to about 0.08 mbar and starting at a temperature −48±8° C. and ramping to a temperature of 0±2° C. over a period in the range of about 40 to about 75 hours; and iii.) a secondary drying step conducted at a pressure of about 0.03 to about 0.08 mbar and starting at a temperature 0±2° C. and ramping to a temperature of about 25±3° C. over a period in the range of about 30 to about 50 hours.

In some embodiments, the liquid medium is an aqueous medium.

In some embodiments, the RNA in the suspension has a concentration in the range of about 0.05 mg/mL to about 2.0 mg/mL. In some embodiments, the RNA in the suspension has a concentration in the range of about 0.075 mg/mL to about 0.3 mg/mL. In some embodiments, the RNA in the suspension has a concentration in the range of about 0.1 mg/mL to about 1.5 mg/mL. In some embodiments, the RNA in the suspension has a concentration in the range of about 0.1 mg/mL to about 1.0 mg/mL. In some embodiments, the RNA in the suspension has a concentration in the range of about 0.1 mg/mL to about 0.5 mg/mL.

In some embodiments, a total lipid to RNA weight ratio in the suspension is about 50:1 to about 10:1. In some embodiments, the total lipid to RNA weight ratio in the suspension is about 40:1 to about 20:1. In some embodiments, the total lipid to RNA weight ratio in the suspension is about 35:1 to about 25:1.

In some embodiments, the pretreated suspension comprises thiosulfate. In some embodiments, the thiosulfate is sodium thiosulfate or potassium thiosulfate. In some embodiments, the thiosulfate has a concentration of about 0.025% w/v to about 1.0% w/v. In some embodiments, the thiosulfate has a concentration of about 0.025% w/v to about 0.75% w/v. In some embodiments, the thiosulfate has a concentration of about 0.025% w/v to about 0.5% w/v. In some embodiments, the thiosulfate has a concentration of about 0.05% w/v to about 0.3% w/v. In some embodiments, the thiosulfate has a concentration of about 0.05% w/v to about 0.25% w/v.

In some embodiments, the pretreated suspension comprises potassium sorbate. In some embodiments, the potassium sorbate has a concentration of about 0.01 M to about 0.5 M. In some embodiments, the potassium sorbate has a concentration of about 0.02 M to about 0.4 M. In some embodiments, the potassium sorbate has a concentration of about 0.025 M to about 0.3 M. In some embodiments, the potassium sorbate has a concentration of about 0.03 M to about 0.2 M. In some embodiments, the potassium sorbate has a concentration of about 0.035 M to about 0.1 M. In some embodiments, the potassium sorbate has a concentration of about 0.04 M to about 0.08 M. In some embodiments, the potassium sorbate has a concentration of about 0.01 M to about 0.05 M. In some embodiments, the potassium sorbate has a concentration of about 0.02 M to about 0.04 M.

In some embodiments, the pretreated suspension comprises iodixanol. In some embodiments, the iodixanol has a concentration of about 5% w/v to about 15% w/v. In some embodiments, the iodixanol has a concentration of about 6% w/v to about 13% w/v. In some embodiments, the iodixanol has a concentration of about 7% w/v to about 11% w/v. In some embodiments, the iodixanol has a concentration of about 8% w/v to about 10% w/v.

In some embodiments, the pretreated suspension comprises sodium benzoate. In some embodiments, the sodium benzoate has a concentration of about 0.01 M to about 0.6 M. In some embodiments, the sodium benzoate has a concentration of about 0.02 M to about 0.5 M. In some embodiments, the sodium benzoate has a concentration of about 0.03 M to about 0.4 M. In some embodiments, the sodium benzoate has a concentration of about 0.04 M to about 0.3 M. In some embodiments, the sodium benzoate has a concentration of about 0.05 M to about 0.2 M.

In some aspects of any of the above embodiments, the pretreated suspension further comprises a polyvinyl alcohol (PVA). In some embodiments, the PVA has a concentration of about 0.01% w/v to about 0.75% w/v.

In some aspects of any of the above embodiments, the pretreated suspension further comprises NaCl. In some embodiments, the NaCl has a concentration of about 0.005 M to about 0.5 M. In some embodiments, the NaCl has a concentration of about 0.01 M to about 0.4 M. In some embodiments, the NaCl has a concentration of about 0.015 M to about 0.3 M. In some embodiments, the NaCl has a concentration of about 0.015 M to about 0.2 M. In some embodiments, the NaCl has a concentration of about 0.015 M to about 0.1 M. In some embodiments, the NaCl has a concentration of about 0.02 M to about 0.05 M. In some embodiments, the NaCl has a concentration of about 0.03 M to about 0.07 M.

In some aspects of any of the above embodiments, the saccharide is sucrose. In some embodiments, the saccharide has a concentration of about 8% w/v to about 20% w/v. In some embodiments, the saccharide has a concentration of about 7% w/v to about 11% w/v. In some embodiments, the saccharide has a concentration of about 8% w/v to about 10% w/v. In some embodiments, the saccharide has a concentration of about 16% w/v to about 20% w/v.

In some aspects of any of the above embodiments, the liquid medium or pretreated suspension comprises a buffer.

In some embodiments, the buffer is selected from 3-morpholinopropane-1-sulfonic acid (MOPS), 2-[4-(2-hydroxyethyl)piperazin-1-yl]ethanesulfonic acid (HEPES), 2-Amino-2-(hydroxymethyl)propane-1,3-diol (TRIS), 2-(N-morpholino)ethanesulfonic acid (MES), citrate, and phosphate buffered saline (PBS). In some embodiments, the buffer is TRIS. In some embodiments, the buffer is in a concentration of about 10 mM to about 100 mM. In some embodiments, the buffer is in a concentration of about 15 mM to about 75 mM. In some embodiments, the buffer is in a concentration of about 10 mM to about 40 mM.

In some aspects of any of the above embodiments, the liquid medium or the pretreated suspension has a pH of about 7.0 to about 8.5.

In some aspects of any of the above embodiments, the method further comprises after step (b), aliquoting a predetermined lyophilization volume of the pretreated suspension into individual containers. In some embodiments, the predetermined lyophilization volume is in the range of about 0.5 mL to about 10.0 mL. In some embodiments, the predetermined lyophilization volume is in the range of about 1.0 mL to about 3.0 mL.

In some aspects of any of the above embodiments, the pretreated suspension further comprises a poloxamer. In some embodiments, the poloxamer is Poloxamer 188. In some embodiments, Poloxamer 188 is poly(ethylene glycol)-block-poly(propylene glycol)-block-poly(ethylene glycol). In some embodiments, Poloxamer 188 is sold under the tradename KOLLIPHOR® P 188 (manufactured by BASF Corporation, batch number GNE08321BT). In some embodiments, Poloxamer 188 has a CAS No. of 9003-11-6. In some embodiments, Poloxamer P188 has the following chemical structure:

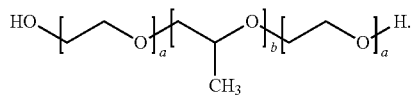

In some embodiments, Poloxamer 188 has less than 620 ppm of ethylene glycol as an impurity. In some embodiments, Poloxamer 188 has an average molecular weight/mass (g/mol) as 8436. In some embodiments, the sum of ethylene glycol and diethylene glycol is less than 0.25 wt. %. In some embodiments, the poloxamer is in a concentration of about 0.01% w/v to about 0.10% w/v. In some embodiments, the poloxamer is in a concentration of about 0.02% w/v to about 0.8% w/v. In some embodiments, the poloxamer is in a concentration of about 0.03% w/v to about 0.7% w/v. In some embodiments, the poloxamer is in a concentration of about 0.04% w/v to about 0.06% w/v.

In some embodiments, a product prepared by the processes described herein is provided.

In some embodiments, a lyophilized composition is provided comprising lipid nanoparticles encapsulating a nucleic acid, a monosaccharide, and one or more excipients selected from potassium sorbate, thiosulfate, sodium benzoate, and iodixanol.

In some embodiments, the nucleic acid is an RNA. In some embodiments, the RNA is a self-replicating RNA. In some embodiments, the RNA is mRNA. In some embodiments, the nucleic acid is from about 20 nucleotides to about 13000 nucleotides in length.

In some embodiments, a total lipid to nucleic acid weight ratio in the lyophilized composition is about 50:1 to about 10:1. In some embodiments, the total lipid to RNA weight ratio in the lyophilized composition is about 40:1 to about 20:1. In some embodiments, the total lipid to RNA weight ratio in the lyophilized composition is about 35:1 to about 25:1.

In some aspects of any of the above embodiments of the lyophilized composition, the lyophilized composition comprises potassium sorbate in a weight ratio of potassium sorbate to RNA of about 30:1 to about 250:1. In some embodiments, the lyophilized composition comprises potassium sorbate in a weight ratio of potassium sorbate to RNA of about 40:1 to about 200:1. In some embodiments, the lyophilized composition comprises potassium sorbate in a weight ratio of potassium sorbate to RNA of about 50:1 to about 175:1.

In some aspects of any of the above embodiments of the lyophilized composition, the lyophilized composition comprises sodium thiosulfate in a weight ratio of sodium thiosulfate to RNA of about 0.25:1 to about 40:1. In some embodiments, the lyophilized composition comprises sodium thiosulfate in a weight ratio of sodium thiosulfate to RNA of about 2:1 to about 10:1. In some embodiments, the lyophilized composition comprises sodium thiosulfate in a weight ratio of sodium thiosulfate to RNA of about 3:1 to about 8:1.

In some aspects of any of the above embodiments of the lyophilized composition, the lyophilized composition comprises sodium benzoate in a weight ratio of sodium benzoate to RNA of about 1:1 to about 12:1. In some embodiments, the lyophilized composition comprises sodium benzoate in a weight ratio of sodium benzoate to RNA of about 2:1 to about 10:1. In some embodiments, the lyophilized composition comprises sodium benzoate in a weight ratio of sodium benzoate to RNA of about 3:1 to about 9:1.

In some aspects of any of the above embodiments of the lyophilized composition, the lyophilized composition comprises iodixanol in a weight ratio of iodixanol to RNA of about 100:1 to about 800:1. In some embodiments, the lyophilized composition comprises iodixanol in a weight ratio of iodixanol to RNA of about 150:1 to about 750:1. In some embodiments, the lyophilized composition comprises iodixanol in a weight ratio of iodixanol to RNA of about 200:1 to about 700:1. In some embodiments, the lyophilized composition comprises iodixanol in a weight ratio of iodixanol to RNA of about 250:1 to about 650:1.

In some aspects of any of the above embodiments of the lyophilized composition, the lyophilized composition further comprises polyvinyl alcohol (PVA) in a weight ratio of PVA to RNA of about 1:1 to about 12:1.

In some aspects of any of the above embodiments of the lyophilized composition, the saccharide is sucrose in a weight ratio of sucrose to RNA of about 100:1 to about 800:1.

In some aspects of any of the above embodiments of the lyophilized composition, the lyophilized composition further comprises a buffer selected from 2-[4-(2-hydroxyethyl)piperazin-1-yl]ethanesulfonic acid (HEPES), 3-morpholinopropane-1-sulfonic acid (MOPS), 2-Amino-2-(hydroxymethyl)propane-1,3-diol (TRIS), 2-(N-morpholino)ethanesulfonic acid (MES), citrate, and phosphate in a weight ratio of buffer to RNA of about 3:1 to about 150:1.

In another embodiment, a lyophilized composition is provided comprising lipid nanoparticles encapsulating an RNA, poloxamer, potassium sorbate, and a sugar. In some embodiments, the poloxamer is poloxamer 188. In some embodiments, the lyophilized composition comprises about 0.001 to about 1.0% w/w of the RNA. In some embodiments, the RNA is mRNA. In some embodiments, the RNA is self-replicating RNA. In some embodiments, the lyophilized composition comprises about 0.005 to about 0.8% w/w of the RNA. In some embodiments, the lyophilized composition comprises about 0.01 to about 0.5% w/w of the RNA. In some embodiments, the lyophilized composition comprises about 0.02 to about 0.4% w/w of the RNA. In some embodiments, the lyophilized composition comprises about 0.03 to about 0.3% w/w of the RNA. In some embodiments, the lyophilized composition comprises about 0.04 to about 0.2% w/w of the RNA. In some embodiments, the lyophilized composition comprises about 0.5 to about 5.0% w/w lipids. In some embodiments, the lyophilized composition comprises about 1.0 to about 4.0% w/w lipids. In some embodiments, the lyophilized composition comprises about 1.25 to about 3.0% w/w lipids. In some embodiments, the lyophilized composition comprises about 0.5 to about 2.5% w/w of TRIS buffer. In some embodiments, the lyophilized composition comprises about 0.75 to about 2.25% w/w of TRIS buffer. In some embodiments, the lyophilized composition comprises about 1.0 to about 2.0% w/w of TRIS buffer. In some embodiments, the lyophilized composition comprises about 0.75 to about 2.75% w/w of NaCl. In some embodiments, the lyophilized composition comprises about 1.0 to about 2.5% w/w of NaCl. In some embodiments, the lyophilized composition comprises about 1.25 to about 1.80% w/w of NaCl. In some embodiments, the lyophilized composition comprises about 85 to about 96% w/w of the sugar. In some embodiments, the lyophilized composition comprises about 88 to about 95% w/w of the sugar. In some embodiments, the lyophilized composition comprises about 90 to about 95% w/w of the sugar. In some embodiments, the sugar is sucrose. In some embodiments, the lyophilized composition comprises about 0.01 to about 1.0% w/w of the poloxamer. In some embodiments, the lyophilized composition comprises about 0.02 to about 0.8% w/w of the poloxamer. In some embodiments, the lyophilized composition comprises about 0.03 to about 0.7% w/w of the poloxamer. In some embodiments, the lyophilized composition comprises about 0.04 to about 0.6% w/w of the poloxamer. In some embodiments, the lyophilized composition comprises about 0.05 to about 0.5% w/w of the poloxamer. In some embodiments, the lyophilized composition comprises about 0.06 to about 0.4% w/w of the poloxamer. In some embodiments, the lyophilized composition comprises about 0.07 to about 0.3% w/w of the poloxamer. In some embodiments, the lyophilized composition comprises about 0.09 to about 0.2% w/w of the poloxamer. In some embodiments, the poloxamer is poloxamer 188. In some embodiments, the lyophilized composition comprises about 0.5 to about 5.0% w/w of potassium sorbate. In some embodiments, the lyophilized composition comprises about 0.75 to about 4.0% w/w of potassium sorbate. In some embodiments, the lyophilized composition comprises about 1.0 to about 3.0% w/w of potassium sorbate. In some embodiments, the lyophilized composition comprises about 1.25 to about 2.75% w/w of potassium sorbate.

In some embodiments, a method of preserving a lyophilized composition is provided comprising storing a lyophilized product described herein at a temperature of about 2° C. to about 8° C. In some embodiments, the method comprises storing the lyophilized product at a temperature of about −20° C.

In some embodiments, a method of reconstituting a lyophilized composition is provided comprising adding a liquid medium to a lyophilized composition described herein. In some embodiments, the liquid medium is an aqueous medium. In some embodiments, the liquid medium comprises a poloxamer. In some embodiments, the poloxamer is P-188. In some embodiments, the liquid medium further comprises a buffer having a pH of about 7.0 to about 8.5.

In some embodiments, a method of treating a disease or disorder in a subject is provided comprising administering to the subject a lyophilized composition described herein reconstituted in a liquid medium. In some embodiments, the reconstituted lyophilized composition is administered intravenously. In some embodiments, the reconstituted lyophilized composition is administered intramuscularly. In some embodiments, the reconstituted lyophilized composition is administered via inhalation. In some embodiments, the reconstituted lyophilized composition is administered mucosally. In some embodiments, the reconstituted lyophilized composition is administered subcutaneously.

Lyophilization

The technique of lyophilization, also referred to as freeze-drying or cryodesiccation, is based on the physical principle of sublimation, the process by which a solid material transitions directly into a gaseous state. Lyophilization and the sublimation principle by which it operates thus stand in direct contrast to the more common drying technique of direct evaporation in which a liquid material transitions to a gas. The basic steps and techniques employed in lyophilization are well understood in the art. (See Rey, Louis, ed. Freeze-drying/lyophilization of pharmaceutical and biological products. CRC Press, 2016; and Nireesha, G. R., et al. Int. j. novel trends in pharm. sci. 3.4 (2013): 87-98). A brief overview is provided below.

Lyophilization is a multistage operation in which each step is critical. The main parameters that affect the outcome of this process can be highly specific to the types of materials being lyophilized and can thus require strict control to obtain quality product. Some of the parameters that must be considered include: the material, for example, the substance being lyophilized that must maintain its desirable properties and activity; the surround medium and its components such as bulking agents, stabilizers, emulsifiers, antioxidants, cryoprotectants, lyoprotectants, and moisture-buffering agents; the equipment being used, the process which has to be adapted according to the specific requirements and low-temperature behavior of the different products under treatment; and the freeze-drying cycle.

The Freeze-Drying Cycle

Regarding the freeze-drying cycle, it is well established that a freeze-drying operation includes: i) The Preparation of the Material; ii) The Freezing Step; iii) The Sublimation Phase or Primary Drying Step; and iv) The Desorption Phase or Secondary Drying Step. After these steps the lyophilized product typically undergoes further processing to ready it for storage.

Preparation of the Material/Pretreatment

The preparation of the material (solid, liquid, paste, emulsion) to be processed includes adjusting the matrix in which it found for example a solution or suspension and the liquid medium in which it is found, pH, tonicity, the addition of other excipients as needed all while ensuring not to impede the material's fundamental properties. The pretreated material is then aliquoted into a predetermined volume for optimized lyophilization. The aliquots can be dispensed into individual containers such as vials.

In some embodiments of the lyophilization method provided herein, the method further comprises prior to step (c), aliquoting a predetermined lyophilization volume of the pretreated suspension into individual containers. In some embodiments, the individual containers are vials. In some embodiments, the predetermined lyophilization volume is in the range of about 0.5 mL to about 5.0 mL. In some embodiments, the predetermined lyophilization volume is in the range of about 1.0 mL to about 4.0 mL.

The Freezing Step

In the freezing step the material is hardened by subjecting it to low temperatures. During this very critical period, all fluids present become solid bodies, either crystalline, amorphous, or glass. In the case of water, this typically gives rise to a complex ice network but it might also be imbedded in glassy structures or remain more or less firmly bound within the interstitial structures. Other liquids and solvents will have specific freezing properties. Solutes may concentrate and even crystallize out. At the same time, the volumetric expansion of the system as water freezes might induce powerful mechanical stresses that combine with the osmotic shock given by the increasing concentration of interstitial fluids.

The Sublimations Phase/Primary Drying

The sublimation phase or primary drying will follow when the frozen material, placed under vacuum, is progressively heated to deliver enough energy for the ice to sublimate. During this critical period a correct balance has to be adjusted between heat input (heat transfer) and water sublimation (mass transfer) so that drying can proceed without inducing adverse reactions in the frozen material such as back melting, puffing, or collapse. A continuous and precise adjustment of the operating pressure is then necessary to link the heat input to the evaporative possibilities of the frozen material.

The Desorption Phase/Secondary Drying

The desorption phase or secondary drying starts when ice is distilled away and a higher vacuum allows the progressive extraction of bound water at above zero temperatures. This, must be done with care since overdrying might be as bad as underdrying, and result in an undesirable dry structure, denaturation, or a product that is not amenable to reconstitution. For each product, an appropriate residual moisture has to be reached under given temperatures and pressures.

Lyophilization of Lipid Nanoparticle Formulations

In some embodiments, a method of lyophilizing a composition comprising lipid nanoparticles encapsulating an RNA is provided, the method comprising the steps of a.) providing a suspension of the lipid nanoparticles in a liquid medium; and b.) adjusting the liquid medium thereby forming a pretreated suspension comprising at least one excipient selected from potassium sorbate, thiosulfate, sodium benzoate, and iodixanol. In some embodiments, the method further comprises a step c.) subjecting the pretreated suspension to a lyophilization process comprising i.) an initial freezing step conducted at a temperature of −52±6° C. and at atmospheric pressure; ii.) a primary drying step conducted at a temperature in the range of −25±2° C. to −48±2° C. and at a pressure in the range of about 25 mTorr to about 75 mTorr; and iii.) a secondary drying step conducted at a temperature in the range of 5±2° C. to 10±2° C. and at a pressure in the range of about 85 mTorr to about 200 mTorr.

In some embodiments, the method further comprises a step c.) subjecting the pretreated suspension to a lyophilization process comprises: i.) an initial freezing step conducted at a temperature of −48±8° C. and at atmospheric pressure; ii.) a primary drying step conducted at a pressure of about 0.03 to about 0.08 mbar and starting at a temperature −48±8° C. and ramping to a temperature of 0±2° C. over a period in the range of about 40 to about 75 hours; and iii.) a secondary drying step conducted at a pressure of about 0.03 to about 0.08 mbar and starting at a temperature 0±2° C. and ramping to a temperature of about 25±3° C. over a period in the range of about 30 to about 50 hours.

In some embodiments, a lyophilization cycle as shown below is followed:

| Step | shelf temperature (° C., ±2° C.) | step duration (h:min) | chamber vacuum (mbar) |
|---|---|---|---|
| Freezing | −50 | 4:00 | atmosphere |
| Evacuate | −50 | 00:30-01:45 | from atmosph. pressure to 0.05 |
| Primary drying | −50 → −25 | 1:00 | 0.05 |
|  | −25 | 22:00 | 0.05 |
|  | −25 → −15 | 1:00 | 0.05 |
|  | −15 | 22:00 | 0.05 |
|  | −15 → 0 | 1:00 | 0.05 |
|  | 0 | 16:00 | 0.05 |
| Secondary drying | 0 → +10 | 1:00 | 0.05 |
|  | 10 | 18:00 | 0.05 |
|  | +10 → +15 | 1:00 | 0.05 |
|  | +15 → +20 | 1:00 | 0.05 |
|  | +20 | 12:00 | 0.05 |
|  | +20 → +25 | 0:30 | 0.05 |
|  | +25 | 6:00 | 0.05 |
| Backfill with $N_2$ and stoppering | 25 | 00:10-00:20 | 700 ± 50 |
| Aeration with air | 5 | 00:10-00:20 | atmosphere |

Lipid Nanoparticles

Several lipid-formulated delivery vehicles are used in the art of delivering nucleic acid medicines including liposomes, cationic liposomes, and lipid nanoparticles. Conventional liposomes are vesicles that consist of at least one bilayer and an internal aqueous compartment. Bilayer membranes of liposomes are typically formed by amphiphilic molecules, such as lipids of synthetic or natural origin that comprise spatially separated hydrophilic and hydrophobic domains (Lasic, Trends Biotechnol., 16: 307-321, 1998). Bilayer membranes of the liposomes can also be formed by amphiphilic polymers and surfactants (e.g., polymerosomes, niosomes, etc.). They generally present as spherical vesicles and can range in size from 20 nm to a few microns.

Liposomes can be composed of cationic, anionic, and/or neutral lipids. As an important subclass of liposomes, cationic liposomes are liposomes that are made in whole or part from positively charged lipids, or more specifically a lipid that comprises both a cationic group and a lipophilic portion. In addition to the general characteristics profiled above for liposomes, the positively charged moieties of cationic lipids used in cationic liposomes provide several advantages and some unique structural features. For example, the lipophilic portion of the cationic lipid is hydrophobic and thus will direct itself away from the aqueous interior of the liposome and associate with other nonpolar and hydrophobic species. Conversely, the cationic moiety will associate with aqueous media and more importantly with polar molecules and species with which it can complex in the aqueous interior of the cationic liposome. For these reasons, cationic liposomes are increasingly being researched for use in gene therapy due to their favorability towards negatively charged nucleic acids via electrostatic interactions, resulting in complexes that offer biocompatibility, low toxicity, and the possibility of the large-scale production required for in vivo clinical applications. Cationic lipids suitable for use in cationic liposomes are listed hereinbelow.

In contrast to liposomes and cationic liposomes, lipid nanoparticles (LNP) have a structure that includes a single monolayer or bilayer of lipids that encapsulates a compound in a solid phase. Thus, unlike liposomes, lipid nanoparticles do not have an aqueous phase or other liquid phase in its interior, but rather the lipids from the bilayer or monolayer shell are directly complexed to the internal compound thereby encapsulating it in a solid core. Lipid nanoparticles are typically spherical vesicles having a relatively uniform dispersion of shape and size. While sources vary on what size qualifies a lipid particle as being a nanoparticle, there is some overlap in agreement that a lipid nanoparticle can have a diameter in the range of from 10 nm to 1000 nm. However, more commonly they are considered to be smaller than 120 nm or even 100 nm.

For lipid nanoparticle nucleic acid delivery systems, the lipid shell can be formulated to include an ionizable cationic lipid which can complex to and associate with the negatively charged backbone of the nucleic acid core. Ionizable cationic lipids with apparent pKa values below about 7 have the benefit of providing a cationic lipid for complexing with the nucleic acid's negatively charged backbone and loading into the lipid nanoparticle at pH values below the pKa of the ionizable lipid where it is positively charged. Then, at physiological pH values, the lipid nanoparticle can adopt a relatively neutral exterior allowing for a significant increase in the circulation half-lives of the particles following i.v. administration. In the context of nucleic acid delivery, lipid nanoparticles offer many advantages over other lipid-based nucleic acid delivery systems including high nucleic acid encapsulation efficiency, potent transfection, improved penetration into tissues to deliver therapeutics, and low levels of cytotoxicity and immunogenicity.

Suitable lipid components and methods of manufacturing lipid nanoparticles are well known in the art and are described for example in PCT/US2020/023442, U.S. Pat. Nos. 8,058,069, 8,822,668, 9,738,593, 9,139,554, PCT/US2014/066242, PCT/US2015/030218, PCT/2017/015886, and PCT/US2017/067756, the contents of which are incorporated by reference.

Cationic Lipids

The lipid nanoparticle preferably includes a cationic lipid suitable for forming a cationic liposome or lipid nanoparticle. Cationic lipids are widely studied for nucleic acid delivery because they can bind to negatively charged membranes and induce uptake. Generally, cationic lipids are amphiphiles containing a positive hydrophilic head group, two (or more) lipophilic tails, or a steroid portion and a connector between these two domains. Preferably, the cationic lipid carries a net positive charge at about physiological pH. Cationic liposomes have been traditionally the most commonly used non-viral delivery systems for oligonucleotides, including plasmid DNA, antisense oligos, and siRNA/small hairpin RNA-shRNA). Cationic lipids, such as DOTAP, (1,2-dioleoyl-3-trimethylammonium-propane) and DOTMA (N-[1-(2,3-dioleoyloxy)propyl]-N,N,N-trimethylammonium methyl sulfate) can form complexes or lipoplexes with negatively charged nucleic acids by electrostatic interaction, providing high in vitro transfection efficiency. In some embodiments, the lipid nanoparticle comprises a combination of two or more cationic lipids. The lipid nanoparticles can further comprise a lipidoid and/or a polymeric component.

In the presently disclosed lipid nanoparticles, the cationic lipid may be, for example, N,N-dioleyl-N,N-dimethylammonium chloride (DODAC), N,N-distearyl-N,N-dimethylammonium bromide (DDAB), 1,2-dioleoyltrimethylammoniumpropane chloride (DOTAP) (also known as N-(2,3-dioleoyloxy)propyl)-N,N,N-trimethylammonium chloride and 1,2-Dioleyloxy-3-trimethylaminopropane chloride salt), N-(1-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethyl-aminopropane (DLinDMA), 1,2-Dilinolenyloxy-N,N-dimethylaminopropane (DLenDMA), 1,2-di-γ-linolenyloxy-N,N-dimethylaminopropane (γ-DLenDMA), 1,2-Dilinoleylcarbamoyloxy-3-dimethylaminopropane (DLin-C-DAP), 1,2-Dilinoleyoxy-3-(dimethylamino)acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA·Cl), 1,2-Dilinoleoyl-3-trimethylaminopropane chloride salt (DLin-TAP·Cl), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanediol (DOAP), 1,2-Dilinoleyloxo-3-(2-N,N-dimethylamino)ethoxypropane (DLin-EG-DMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine, (6Z,9Z,28Z,31Z)-heptatriaconta-6,9,28,31-tetraen-19-yl4-(dimethylamino) butanoate (MC3), 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (C12-200), 2,2-dilinoleyl-4-(2-dimethylaminoethyl)-[1,3]-dioxolane (DLin-K-C2-DMA), 2,2-dilinoleyl-4-dimethylaminomethyl-[1,3]-dioxolane (DLin-K-DMA), (6Z,9Z,28Z,31Z)-heptatriaconta-6,9,28 31-tetraen-19-yl 4-(dimethylamino) butanoate (DLin-M-C3-DMA), 3-((6Z,9Z,28Z,31Z)-heptatriaconta-6,9,28,3 1-tetraen-19-yloxy)-N,N-dimethylpropan-1-amine (MC3 Ether), 4-((6Z,9Z,28Z,31 Z)-heptatriaconta-6,9,28,31-tetraen-19-yloxy)-N,N-dimethylbutan-1-amine (MC4 Ether), or any combination thereof. Other cationic lipids include, but are not limited to, N,N-distearyl-N,N-dimethylammonium bromide (DDAB), 3β—(N—(N', N'-dimethylaminoethane)-carbamoyl)cholesterol (DC-Choi), N-(1-(2,3-dioleyloxy)propyl)-N-2-(sperminecarboxamido)ethyl)-N,N-dimethylammonium trifluoracetate (DOSPA), dioctadecylamidoglycyl carboxyspermine (DOGS), 1,2-dileoyl-sn-3-phosphoethanolamine (DOPE), 1,2-dioleoyl-3-dimethylammonium propane (DODAP), N-(1,2-dimyristyloxyprop-3-yl)-N,N-dimethyl-N-hydroxyethyl ammonium bromide (DMRIE), and 2,2-Dilinoleyl-4-dimethylaminoethyl-[1,3]-dioxolane (XTC). Additionally, commercial preparations of cationic lipids can be used, such as, e.g., a 1:1 (w/w) liposome formulation of the cationic lipid N-[1-(2,3-dioleyloxy)propyl]-n,n,n-trim-ethylammonium chloride (DOTMA) and dioleoyl phophotidylethanolamine (DOPE) sold under the trademark LIPOFECTIN™ (available from GIBCO/BRL), and a 3:1 mixture of DOSPA (2,3-dioleoyloxy-N-[2(sperminecarboxamido) ethyl]-N,N-dimethyl-1-propaniminium trifluoroacetate) and DOPE sold under the trademark Lipofectamine™ (available from GIBCO/BRL).

Other example cationic lipids are disclosed in International Publication Nos. WO 09/086558, WO 09/127060, WO 10/048536, WO 10/054406, WO 10/088537, WO 10/129709, and WO 2011/153493; U.S. Patent Publication Nos. 2011/0256175, 2012/0128760, and 2012/0027803; U.S. Pat. No. 8,158,601; and Love et al., PNAS, 107(5), 1864-69, 2010.

Other suitable cationic lipids include those having alternative fatty acid groups and other dialkylamino groups, including those, in which the alkyl substituents are different (e.g., N-ethyl-N-methylamino-, and N-propyl-N-ethyl-amino-). These lipids are part of a subcategory of cationic lipids referred to as amino lipids. In some embodiments of the lipid nanoparticles described herein, the cationic lipid is an amino lipid. In general, amino lipids having less saturated acyl chains are more easily sized, particularly when the complexes must be sized below about 0.3 microns, for purposes of filter sterilization. Amino lipids containing unsaturated fatty acids with carbon chain lengths in the range of C14 to C22 may be used. Other scaffolds can also be used to separate the amino group and the fatty acid or fatty alkyl portion of the amino lipid.

In some embodiments, the lipid nanoparticle comprises the cationic lipid with Formula I according to the patent application PCT/EP2017/064066. In this context, the disclosure of PCT/EP2017/064066 is also incorporated herein by reference.

In some embodiments, amino or cationic lipids of the present disclosure are ionizable and have at least one protonatable or deprotonatable group, such that the lipid is positively charged at a pH at or below physiological pH (e.g., pH 7.4), and neutral at a second pH, preferably at or above physiological pH. Of course, it will be understood that the addition or removal of protons as a function of pH is an equilibrium process, and that the reference to a charged or a neutral lipid refers to the nature of the predominant species and does not require that all of the lipid be present in the charged or neutral form. Lipids that have more than one protonatable or deprotonatable group, or which are zwitterionic, are not excluded from use in the disclosure. In certain embodiments, the protonatable lipids have a pKa of the protonatable group in the range of about 4 to about 11. In some embodiments, the ionizable cationic lipid has a pKa of about 5 to about 7. In some embodiments, the pKa of an ionizable cationic lipid is about 6 to about 7.

In some embodiments, the lipid nanoparticle comprises an ionizable cationic lipid of Formula I.

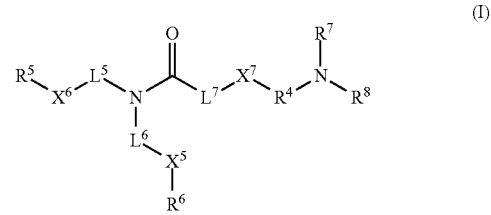

(I)

or a pharmaceutically acceptable salt or solvate thereof, wherein $R^5$ and $R^6$ are each independently selected from the group consisting of a linear or branched $C_1$-$C_{31}$ alkyl, $C_2$-$C_{31}$ alkenyl or $C_2$-$C_{31}$ alkynyl and cholesteryl; $L^5$ and $L^6$ are each independently selected from the group consisting of a linear $C_1$-$C_{20}$ alkyl and $C_2$-$C_{20}$ alkenyl; $X^5$ is —C(O)O—, whereby —C(O)O—$R^6$ is formed or —OC(O)— whereby —OC(O)—$R^6$ is formed; $X^6$ is —C(O)O— whereby —C(O)O—$R^5$ is formed or —OC(O)— whereby —OC(O)—$R^5$ is formed; $X^7$ is S or O; $L^7$ is absent or lower alkyl; $R^4$ is a linear or branched $C_1$-$C_6$ alkyl; and $R^7$ and $R^8$ are each independently selected from the group consisting of a hydrogen and a linear or branched $C_1$-$C_6$ alkyl.

In some embodiments, $X^7$ is S.

In some embodiments, $X^5$ is —C(O)O—, whereby —C(O)O—$R^6$ is formed and $X^6$ is —C(O)O— whereby —C(O)O—$R^5$ is formed.

In some embodiments, $R^7$ and $R^8$ are each independently selected from the group consisting of methyl, ethyl and isopropyl.

In some embodiments, $L^5$ and $L^6$ are each independently a $C_1$-$C_{10}$ alkyl. In some embodiments, $L^5$ is $C_1$-$C_3$ alkyl, and $L^6$ is $C_1$-$C_5$ alkyl. In some embodiments, $L^6$ is $C_1$-$C_2$ alkyl. In some embodiments, $L^5$ and $L^6$ are each a linear $C_7$ alkyl. In some embodiments, $L^5$ and $L^6$ are each a linear $C_9$ alkyl.

In some embodiments, $R^5$ and $R^6$ are each independently an alkenyl. In some embodiments, $R^6$ is alkenyl. In some embodiments, $R^6$ is $C_2$-$C_9$ alkenyl. In some embodiments, the alkenyl comprises a single double bond. In some embodiments, $R^5$ and $R^6$ are each alkyl. In some embodiments, $R^5$ is a branched alkyl. In some embodiments, $R^5$ and $R^6$ are each independently selected from the group consisting of a $C_9$ alkyl, $C_9$ alkenyl and $C_9$ alkynyl. In some embodiments, $R^5$ and $R^6$ are each independently selected from the group consisting of a $C_{11}$ alkyl, $C_{11}$ alkenyl and $C_{11}$ alkynyl. In some embodiments, $R^5$ and $R^6$ are each independently selected from the group consisting of a $C_7$ alkyl, $C_7$ alkenyl and $C_7$ alkynyl. In some embodiments, $R^5$ is —CH(($CH_2)_p$$CH_3)_2$ or —CH(($CH_2)_p$$CH_3$)(($CH_2)_{p-1}$$CH_3$), wherein p is 4-8. In some embodiments, p is 5 and $L^5$ is a $C_1$-$C_3$ alkyl. In some embodiments, p is 6 and $L^5$ is a $C_3$ alkyl. In some embodiments, p is 7. In some embodiments, p is 8 and $L^5$ is a $C_1$-$C_3$ alkyl. In some embodiments, $R^5$ consists of —CH(($CH_2)_p$$CH_3$)(($CH_2)_{p-1}$$CH_3$), wherein p is 7 or 8.

In some embodiments, $R^4$ is ethylene or propylene. In some embodiments, $R^4$ is n-propylene or isobutylene.

In some embodiments, $L^7$ is absent, $R^4$ is ethylene, $X^7$ is S and $R^7$ and $R^8$ are each methyl. In some embodiments, $L^7$ is absent, $R^4$ is n-propylene, $X^7$ is S and $R^7$ and $R^8$ are each methyl. In some embodiments, $L^7$ is absent, $R^4$ is ethylene, $X^7$ is S and $R^7$ and $R^8$ are each ethyl.

In some embodiments, $X^7$ is S, $X^5$ is —C(O)O—, whereby —C(O)O—$R^6$ is formed, $X^6$ is —C(O)O— whereby —C(O)O—$R^5$ is formed, $L^5$ and $L^6$ are each independently a linear $C_3$-$C_7$ alkyl, $L^7$ is absent, $R^5$ is —CH(($CH_2)_p$$CH_3)_2$, and $R^6$ is $C_7$-$C_{12}$ alkenyl. In some further embodiments, p is 6 and $R^6$ is $C_9$ alkenyl.

Helper Lipids and Sterols

The RNA-lipid nanoparticles of the present disclosure can comprise a helper lipid, which can be referred to as a neutral helper lipid, non-cationic lipid, non-cationic helper lipid, anionic lipid, anionic helper lipid, or a neutral lipid. It has been found that lipid formulations, particularly cationic liposomes and lipid nanoparticles have increased cellular uptake if helper lipids are present in the formulation. (Curr. Drug Metab. 2014; 15(9):882-92). For example, some studies have indicated that neutral and zwitterionic lipids such as 1,2-dioleoylsn-glycero-3-phosphatidylcholine (DOPC), Di-Oleoyl-Phosphatidyl-Ethanoalamine (DOPE) and 1,2-DiStearoyl-sn-glycero-3-PhosphoCholine (DSPC), being more fusogenic (i.e., facilitating fusion) than cationic lipids, can affect the polymorphic features of lipid-nucleic acid complexes, promoting the transition from a lamellar to a hexagonal phase, and thus inducing fusion and a disruption of the cellular membrane. (Nanomedicine (Lond). 2014 January; 9(1):105-20). In addition, the use of helper lipids can help to reduce any potential detrimental effects from using many prevalent cationic lipids such as toxicity and immunogenicity.

Non-limiting examples of non-cationic lipids suitable for lipid nanoparticles of the present disclosure include phospholipids such as lecithin, phosphatidylethanolamine, lysolecithin, lysophosphatidylethanolamine, phosphatidylserine, phosphatidylinositol, sphingomyelin, egg sphingomyelin (ESM), cephalin, cardiolipin, phosphatidic acid, cerebrosides, dicetylphosphate, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoylphosphatidylethanolamine (DOPE), palmitoyloleoyl-phosphatidylcholine (POPC), palmitoyloleoyl-phosphatidylethanolamine (POPE), palmitoyloleyol-phosphatidylglycerol (POPG), dioleoylphosphatidylethanolamine 4-(N-maleimidomethyl)-cyclohexane-1-carboxylate (DOPE-mal), dipalmitoyl-phosphatidylethanolamine (DPPE), dimyristoyl-phosphatidylethanolamine (DMPE), distearoyl-phosphatidylethanolamine (DSPE), monomethyl-phosphatidylethanolamine, dimethyl-phosphatidylethanolamine, dielaidoyl-phosphatidylethanolamine (DEPE), stearoyloleoyl-phosphatidylethanolamine (SOPE), lysophosphatidylcholine, dilinoleoylphosphatidylcholine, and mixtures thereof. Other diacylphosphatidylcholine and diacylphosphatidylethanolamine phospholipids can also be used. The acyl groups in these lipids are preferably acyl groups derived from fatty acids having C10-C24 carbon chains, e.g., lauroyl, myristoyl, palmitoyl, stearoyl, or oleoyl.

Additional examples of non-cationic lipids include sterols such as cholesterol and derivatives thereof. One study concluded that as a helper lipid, cholesterol increases the spacing of the charges of the lipid layer interfacing with the nucleic acid making the charge distribution match that of the nucleic acid more closely. (J. R. Soc. Interface. 2012 Mar. 7; 9(68): 548-561). Non-limiting examples of cholesterol derivatives include polar analogues such as 5α-cholestanol, 5α-coprostanol, cholesteryl-(2'-hydroxy)-ethyl ether, cholesteryl-(4'-hydroxy)-butyl ether, and 6-ketocholestanol; non-polar analogues such as 5α-cholestane, cholestenone, 5α-cholestanone, 5α-cholestanone, and cholesteryl decanoate; and mixtures thereof. In preferred embodiments, the cholesterol derivative is a polar analogue such as cholesteryl-(4'-hydroxy)-butyl ether.

In some embodiments, the helper lipid present in the lipid nanoparticle comprises or consists of a mixture of one or more phospholipids and cholesterol or a derivative thereof. In other embodiments, the neutral lipid present in the lipid nanoparticle comprises or consists of one or more phospholipids, e.g., a cholesterol-free lipid nanoparticle. In yet other embodiments, the neutral lipid present in the lipid nanoparticle comprises or consists of cholesterol or a derivative thereof, e.g., a phospholipid-free lipid nanoparticle.

Other examples of helper lipids include nonphosphorous containing lipids such as, e.g., stearylamine, dodecylamine, hexadecylamine, acetyl palmitate, glycerol ricinoleate, hexadecyl stearate, isopropyl myristate, amphoteric acrylic polymers, triethanolamine-lauryl sulfate, alkyl-aryl sulfate polyethyloxylated fatty acid amides, dioctadecyldimethyl ammonium bromide, ceramide, and sphingomyelin.

In some embodiments, the helper lipid comprises from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid nanoparticle.

The cholesterol or cholesterol derivative in the lipid nanoparticle may comprise up to about 40 mol %, about 45 mol %, about 50 mol %, about 55 mol %, or about 60 mol % of the total lipid present in the lipid nanoparticle. In some embodiments, the cholesterol or cholesterol derivative comprises about 15 mol % to about 45 mol %, about 20 mol % to about 40 mol %, about 25 mol % to about 35 mol %, or about 28 mol % to about 35 mol %; or about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, or about 37 mol % of the total lipid present in the lipid nanoparticle.

In some embodiments, the phospholipid component in the mixture may comprise from about 2 mol % to about 20 mol %, from about 3 mol % to about 18 mol %, from about 4 mol % to about 16 mol %, about 5 mol % to about 14 mol %, from about 6 mol % to about 12 mol %, from about 5 mol % to about 10 mol %, from about 5 mol % to about 9 mol %, or about 2 mol %, about 3 mol %, about 4 mol %, about 5 mol %, about 6 mol %, about 7 mol %, about 8 mol %, about 9 mol %, about 10 mol %, about 11 mol %, or about 12 mol % (or any fraction thereof or the range therein) of the total lipid present in the lipid nanoparticle.

The percentage of helper lipid present in the lipid nanoparticle is a target amount, and the actual amount of helper lipid present in the formulation may vary, for example, by ±5 mol %.

A lipid nanoparticle containing a cationic lipid compound or ionizable cationic lipid compound (or a combination of 2 cationic lipids) may be on a molar basis about 30-70% cationic lipid compound(s), about 25-40% cholesterol, about 2-15% helper lipid, and about 0.5-5% of a polyethylene glycol (PEG) lipid, wherein the percent is of the total lipid present in the formulation. In some embodiments, the composition is about 40-65% cationic lipid compound, about 25-35% cholesterol, about 3-9% helper lipid, and about 0.5-3% of a PEG-lipid, wherein the percent is of the total lipid present in the formulation.

The formulation may be a lipid particle formulation, for example containing 8-30% nucleic acid compound, 5-30% helper lipid, and 0-20% cholesterol; 4-25% cationic lipid, 4-25% helper lipid, 2-25% cholesterol, 10-35% cholesterol-PEG, and 5% cholesterol-amine; or 2-30% cationic lipid, 2-30% helper lipid, 1-15% cholesterol, 2-35% cholesterol-PEG, and 1-20% cholesterol-amine; or up to 90% cationic lipid and 2-10% helper lipids, or even 100% cationic lipid.

Lipid Conjugates

The lipid nanoparticles described herein may further comprise a lipid conjugate. The conjugated lipid is useful in that it prevents the aggregation of particles. Suitable conjugated lipids include, but are not limited to, PEG-lipid conjugates, cationic-polymer-lipid conjugates, and mixtures thereof. Furthermore, lipid delivery vehicles can be used for specific targeting by attaching ligands (e.g., antibodies, peptides, and carbohydrates) to its surface or to the terminal end of the attached PEG chains (Front Pharmacol. 2015 Dec. 1; 6:286).

In a preferred embodiment, the lipid conjugate is a PEG-lipid. The inclusion of polyethylene glycol (PEG) in a lipid nanoparticle as a coating or surface ligand, a technique referred to as PEGylation, helps to protects nanoparticles from the immune system and their escape from RES uptake (Nanomedicine (Lond). 2011 June; 6(4):715-28). PEGylation has been widely used to stabilize lipid nanoparticles and their payloads through physical, chemical, and biological mechanisms. Detergent-like PEG lipids (e.g., PEG-DSPE) can enter the lipid nanoparticle to form a hydrated layer and steric barrier on the surface. Based on the degree of PEGylation, the surface layer can be generally divided into two types, brush-like and mushroom-like layers. For PEG-DSPE-stabilized formulations, PEG will take on the mushroom conformation at a low degree of PEGylation (usually less than 5 mol %) and will shift to brush conformation as the content of PEG-DSPE is increased past a certain level (Journal of Nanomaterials. 2011; 2011:12). It has been shown that increased PEGylation leads to a significant increase in the circulation half-life of lipid nanoparticles (Annu. Rev. Biomed. Eng. 2011 Aug. 15; 13( ):507-30; J. Control Release. 2010 Aug. 3; 145(3):178-81).

Suitable examples of PEG-lipids include, but are not limited to, PEG coupled to dialkyloxypropyls (PEG-DAA), PEG coupled to diacylglycerol (PEG-DAG), PEG coupled to phospholipids such as phosphatidylethanolamine (PEG-PE), PEG conjugated to ceramides, PEG conjugated to cholesterol or a derivative thereof, and mixtures thereof.

PEG is a linear, water-soluble polymer of ethylene PEG repeating units with two terminal hydroxyl groups. PEGs are classified by their molecular weights and include the following: monomethoxypolyethylene glycol (MePEG-OH), monomethoxypolyethylene glycol-succinate (MePEG-S), monomethoxypolyethylene glycol-succinimidyl succinate (MePEG-S—NHS), monomethoxypolyethylene glycol-amine (MePEG-NH$_2$), monomethoxypolyethylene glycol-tresylate (MePEG-TRES), monomethoxypolyethylene glycol-imidazolyl-carbonyl (MePEG-IM), as well as such compounds containing a terminal hydroxyl group instead of a terminal methoxy group (e.g., HO-PEG-S, HO-PEG-S—NHS, HO-PEG-NH$_2$).

The PEG moiety of the PEG-lipid conjugates described herein may comprise an average molecular weight ranging from about 550 daltons to about 10,000 daltons. In certain instances, the PEG moiety has an average molecular weight of from about 750 daltons to about 5,000 daltons (e.g., from about 1,000 daltons to about 5,000 daltons, from about 1,500 daltons to about 3,000 daltons, from about 750 daltons to about 3,000 daltons, from about 750 daltons to about 2,000 daltons). In preferred embodiments, the PEG moiety has an average molecular weight of about 2,000 daltons or about 750 daltons. The average molecular weight may be any value or subvalue within the recited ranges, including endpoints.

In certain instances, the PEG can be optionally substituted by an alkyl, alkoxy, acyl, or aryl group. The PEG can be conjugated directly to the lipid or may be linked to the lipid via a linker moiety. Any linker moiety suitable for coupling the PEG to a lipid can be used including, e.g., non-ester-containing linker moieties and ester-containing linker moieties. In a preferred embodiment, the linker moiety is a non-ester-containing linker moiety. Suitable non-ester-containing linker moieties include, but are not limited to, amido (—C(O)NH—), amino (—NR—), carbonyl (—C(O)—), carbamate (—NHC(O)O—), urea (—NHC(O)NH—), disulfide (—S—S—), ether (—O—), succinyl (—(O)CCH$_2$CH$_2$C(O)—), succinamidyl (—NHC(O)CH$_2$CH$_2$C(O)NH—), ether, as well as combinations thereof (such as a linker containing both a carbamate linker moiety and an amido linker moiety). In a preferred embodiment, a carbamate linker is used to couple the PEG to the lipid.

In other embodiments, an ester-containing linker moiety is used to couple the PEG to the lipid. Suitable ester-containing linker moieties include, e.g., carbonate (—OC(O)O—), succinoyl, phosphate esters (—O—(O)POH—O—), sulfonate esters, and combinations thereof.

Phosphatidylethanolamines having a variety of acyl chain groups of varying chain lengths and degrees of saturation can be conjugated to PEG to form the lipid conjugate. Such phosphatidylethanolamines are commercially available or can be isolated or synthesized using conventional techniques known to those of skill in the art. Phosphatidylethanolamines containing saturated or unsaturated fatty acids with carbon chain lengths in the range of C10 to C20 are preferred. Phosphatidylethanolamines with mono- or di-unsaturated fatty acids and mixtures of saturated and unsaturated fatty acids can also be used. Suitable phosphatidylethanolamines include, but are not limited to, dimyristoyl-phosphatidylethanolamine (DMPE), dipalmitoyl-phosphatidylethanolamine (DPPE), dioleoyl-phosphatidylethanolamine (DOPE), and distearoyl-phosphatidylethanolamine (DSPE).

In some embodiments, the PEG-DAA conjugate is a PEG-didecyloxypropyl ($C_{10}$) conjugate, a PEG-dilauryloxypropyl ($C_{12}$) conjugate, a PEG-dimyristyloxypropyl ($C_{14}$) conjugate, a PEG-dipalmityloxypropyl ($C_{16}$) conjugate, or a PEG-distearyloxypropyl ($C_{18}$) conjugate. In these embodiments, the PEG preferably has an average molecular weight of about 750 or about 2,000 daltons. In particular embodiments, the terminal hydroxyl group of the PEG is substituted with a methyl group.

In addition to the foregoing, other hydrophilic polymers can be used in place of PEG. Examples of suitable polymers that can be used in place of PEG include, but are not limited to, polyvinylpyrrolidone, polymethyloxazoline, polyethyloxazoline, polyhydroxypropyl, methacrylamide, polymethacrylamide, and polydimethylacrylamide, polylactic acid, polyglycolic acid, and derivatized celluloses such as hydroxymethylcellulose or hydroxyethylcellulose.

In some embodiments, the lipid conjugate (e.g., PEG-lipid) comprises from about 0.1 mol % to about 2 mol %, from about 0.5 mol % to about 2 mol %, from about 1 mol % to about 2 mol %, from about 0.6 mol % to about 1.9 mol %, from about 0.7 mol % to about 1.8 mol %, from about 0.8 mol % to about 1.7 mol %, from about 0.9 mol % to about 1.6 mol %, from about 0.9 mol % to about 1.8 mol %, from about 1 mol % to about 1.8 mol %, from about 1 mol % to about 1.7 mol %, from about 1.2 mol % to about 1.8 mol %, from about 1.2 mol % to about 1.7 mol %, from about 1.3 mol % to about 1.6 mol %, or from about 1.4 mol % to about 1.6 mol % (or any fraction thereof or range therein) of the total lipid present in the lipid nanoparticle. In other embodiments, the lipid conjugate (e.g., PEG-lipid) comprises about 0.5%, 0.6%, 0.7%, 0.8%, 0.9%, 1.0%, 1.2%, 1.3%, 1.4%, 1.5%, 1.6%, 1.7%, 1.8%, 1.9%, 2.0%, 2.5%, 3.0%, 3.5%, 4.0%, 4.5%, or 5%, (or any fraction thereof or range therein) of the total lipid present in the lipid nanoparticle. The amount may be any value or subvalue within the recited ranges, including endpoints.

The percentage of lipid conjugate (e.g., PEG-lipid) present in the lipid nanoparticles of the disclosure is a target amount, and the actual amount of lipid conjugate present in the formulation may vary, for example, by ±0.5 mol %. One of ordinary skill in the art will appreciate that the concentration of the lipid conjugate can be varied depending on the lipid conjugate employed and the rate at which the lipid nanoparticle is to become fusogenic.

Lipid Nanoparticle-Nucleic Acid Formulations

In the context of the present disclosure, a lipid nanoparticle delivery vehicle typically serves to transport a nucleic acid (e.g., RNA) to a target cell or tissue. Example nucleic acids include both DNA and RNA. In preferred embodiments, the lipid nanoparticles comprise an RNA, a cationic lipid (e.g., one or more cationic lipids or salts thereof), a phospholipid, and a conjugated lipid that inhibits aggregation of the particles (e.g., one or more PEG-lipid conjugates). The lipid nanoparticles can also include cholesterol.

In some embodiments, the RNA is fully encapsulated within the lipid portion of the lipid nanoparticle such that the RNA is resistant in aqueous solution to nuclease degradation.

The term "RNA" means a molecule comprising at least one ribonucleotide residue. By "ribonucleotide" is meant a nucleotide with a hydroxyl group at the 2' position of a β-D-ribo-furanose moiety. The terms includes double-stranded RNA, single-stranded RNA, isolated RNA such as partially purified RNA, essentially pure RNA, synthetic RNA, recombinantly produced RNA, as well as altered RNA that differs from naturally occurring RNA by the addition, deletion, substitution, and/or alteration of one or more nucleotides. Such alterations can include addition of non-nucleotide material, such as to the end(s) of an interfering RNA or internally, for example at one or more nucleotides of the RNA. Nucleotides in the RNA molecules of the instant disclosure can also comprise non-standard nucleotides, such as non-naturally occurring nucleotides or chemically synthesized nucleotides or deoxynucleotides. These altered RNAs can be referred to as analogs or analogs of naturally-occurring RNA. As used herein, the terms "ribonucleic acid" and "RNA" refer to a molecule containing at least one ribonucleotide residue, including siRNA, antisense RNA, single stranded RNA, microRNA, mRNA, noncoding RNA, and multivalent RNA.

In some embodiments the RNA is a self-replicating RNA. In some embodiments, the RNA is mRNA. In some embodiments, the RNA is siRNA. In some embodiments, the nucleic acid is from about 1000 nucleotides to about 13000 nucleotides in length.

The lipid nanoparticles of the disclosure also typically have a total lipid:RNA ratio (mass/mass ratio) of from about 1:1 to about 100:1, from about 1:1 to about 50:1, from about 2:1 to about 45:1, from about 3:1 to about 40:1, from about 5:1 to about 38:1, or from about 6:1 to about 40:1, or from about 7:1 to about 35:1, or from about 8:1 to about 30:1; or from about 10:1 to about 25:1; or from about 8:1 to about 12:1; or from about 13:1 to about 17:1; or from about 18:1 to about 24:1; or from about 20:1 to about 30:1. In some preferred embodiments, the total lipid:RNA ratio (mass/mass ratio) is from about 10:1 to about 25:1. In some embodiments, the total lipid to RNA weight ratio in the suspension is about 50:1 to about 10:1. In some embodiments, the total lipid to RNA weight ratio in the suspension is about 40:1 to about 20:1. In some embodiments, the total lipid to RNA weight ratio in the suspension is about 35:1 to about 25:1. The ratio may be any value or subvalue within the recited ranges, including endpoints.

The lipid nanoparticles of the present disclosure typically have a mean diameter of from about 30 nm to about 150 nm, from about 40 nm to about 150 nm, from about 50 nm to about 150 nm, from about 60 nm to about 130 nm, from about 70 nm to about 110 nm, from about 70 nm to about 100 nm, from about 80 nm to about 100 nm, from about 90 nm to about 100 nm, from about 70 to about 90 nm, from about 80 nm to about 90 nm, from about 70 nm to about 80 nm, or about 30 nm, about 35 nm, about 40 nm, about 45 nm, about 50 nm, about 55 nm, about 60 nm, about 65 nm, about 70 nm, about 75 nm, about 80 nm, about 85 nm, about 90 nm, about 95 nm, about 100 nm, about 105 nm, about 110 nm, about 115 nm, about 120 nm, about 125 nm, about 130 nm, about 135 nm, about 140 nm, about 145 nm, or about 150 nm, and are substantially non-toxic. The diameter may be any value or subvalue within the recited ranges, including endpoints.

In the context of nucleic acids, full encapsulation may be determined by performing a membrane-impermeable fluorescent dye exclusion assay, which uses a dye that has enhanced fluorescence when associated with nucleic acid. Encapsulation is determined by adding the dye to a lipid nanoparticle, measuring the resulting fluorescence, and comparing it to the fluorescence observed upon addition of a small amount of nonionic detergent. Detergent-mediated disruption of the lipid layer releases the encapsulated nucleic acid, allowing it to interact with the membrane-impermeable dye. Nucleic acid encapsulation may be calculated as $E=(I_0-I)/I_0$, where $I$ and $I_0$ refer to the fluorescence intensities before and after the addition of detergent.

In some embodiments, the lipid nanoparticles comprise an RNA that is fully encapsulated within the lipid portion of the formulation, such that from about 30% to about 100%, from about 40% to about 100%, from about 50% to about 100%, from about 60% to about 100%, from about 70% to about 100%, from about 80% to about 100%, from about 90% to about 100%, from about 30% to about 95%, from about 40% to about 95%, from about 50% to about 95%, from about 60% to about 95%, from about 70% to about 95%, from about 80% to about 95%, from about 85% to about 95%, from about 90% to about 95%, from about 30% to about 90%, from about 40% to about 90%, from about 50% to about 90%, from about 60% to about 90%, from about 70% to about 90%, from about 80% to about 90%, or at least about 30%, about 35%, about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99% (or any fraction thereof or range therein) of the particles have the RNA encapsulated therein. The amount may be any value or subvalue within the recited ranges, including endpoints.

Suspensions and Liquid Media

A suspension is a heterogeneous mixture in which the solute particles do not dissolve, but get suspended throughout the bulk of the solvent, left floating around freely in the medium. The internal phase (solid) is dispersed throughout the external phase (fluid), which can be facilitated by the use of certain excipients or suspending agents. The liquid media used for suspending the lipid nanoparticles can be comprise any suitable liquid medium known in the art. Suitable liquids used in pharmaceutical suspensions include alcohol, glycerin, polyethylene glycol and polypropylene glycol. The mechanism by which these liquids provide wetting is that they are miscible with water and reduce liquid air interfacial tension. Liquid penetrates in individual particle and facilitates wetting. In some embodiments, the liquid medium is an aqueous medium.

In the present disclosure, the concentration of lipid nanoparticles in the suspension is disclosed as the concentration of the encapsulated RNA per mL of suspension. In some embodiments, the RNA in the suspension has a concentration in the range of about 0.1 mg/mL to about 2.0 mg/mL. In some embodiments, the RNA in the suspension has a concentration in the range of about 0.1 mg/mL to about 1.5 mg/mL. In some embodiments, the RNA in the suspension has a concentration in the range of about 0.1 mg/mL to about 1.0 mg/mL. In some embodiments, the RNA in the suspension has a concentration in the range of about 0.1 mg/mL to about 0.5 mg/mL.

Excipients, Lyoprotectants, Cryoprotectants, and Buffers

The lipid nanoparticle-RNA formulations can be pretreated to facilitate lyophilization and reconstitution. Typically, buffered suspensions of lipid nanoparticle-RNA formulations are combined with special excipients, some of which serve as lyoprotectants and/or cryoprotectants. As used herein, the term "lyoprotectant" refers to a substance, compound, or excipient that is added to a composition in order to protect the active ingredients during the drying stages of lyophilization, to help preserve or stabilize the lyophilized product, and/or to help make the lyophilized product more easily reconstituted. A lyoprotectant can also be used as the bulking agent. As used herein, a "cryoprotectant" refers to a substance, compound, or excipient that is added to a biological or pharmaceutical composition to protect it from freezing damage.

In some embodiments, the pretreated suspension comprises a lyoprotectant. In some embodiments, the pretreated suspension comprises a cyroprotectant.

Suitable examples of excipients used in the lyophilization process either as a lyoprotectant or a cryoprotectant include saccharide compounds (e.g., a monosaccharide, a disaccharide, etc.). Examples of protectant sugar compounds include monosaccharides such as $C_{5-6}$ aldoses and ketoses, as well as disaccharides such as sucrose, lactose, maltose, trehalose, cellobiose, kojbiose, sakebiose, isomaltose, sophorose, laminaribiose, gentiobiose, turanose, maltulose, isomaltulose, gentiobiulose, mannobiose, melibiose, melibiulose, and xylobiose.

In some embodiments, the pretreated suspension comprises a thiosulfate. The thiosulfate can be any suitable thiosulfate salt for in vivo administration. In some embodiments, the thiosulfate is sodium thiosulfate or potassium thiosulfate. In some embodiments, the thiosulfate is sodium thiosulfate. In some embodiments, the pretreated suspension has a thiosulfate concentration of about 0.025% w/v to about 1.0% w/v. In some embodiments, the thiosulfate is sodium thiosulfate. In some embodiments, the pretreated suspension has a thiosulfate concentration of about 0.025% w/v to about 0.75% w/v. In some embodiments, the thiosulfate is sodium thiosulfate. In some embodiments, the pretreated suspension has a thiosulfate concentration of about 0.025% w/v to about 0.5% w/v. In some embodiments, the thiosulfate is sodium thiosulfate. In some embodiments, the pretreated suspension has a thiosulfate concentration of about 0.05% w/v to about 0.3% w/v. In some embodiments, the thiosulfate is sodium thiosulfate. In some embodiments, the pretreated suspension has a thiosulfate concentration of about 0.05% w/v to about 0.25% w/v.

In some embodiments, the pretreated suspension comprises potassium sorbate. In some embodiments, the pretreated suspension has a potassium sorbate concentration of about 0.01 M to about 0.5 M. In some embodiments, the pretreated suspension has a potassium sorbate concentration of about 0.02 M to about 0.4 M. In some embodiments, the pretreated suspension has a potassium sorbate concentration of about 0.025 M to about 0.3 M. In some embodiments, the pretreated suspension has a potassium sorbate concentration of about 0.03 M to about 0.2 M. In some embodiments, the pretreated suspension has a potassium sorbate concentration of about 0.035 M to about 0.1 M. In some embodiments, the pretreated suspension has a potassium sorbate concentration of about 0.04 M to about 0.08 M. In some embodiments, the pretreated suspension has a potassium sorbate concentration of about 0.015 M to about 0.06 M. In some embodiments, the pretreated suspension has a potassium sorbate concentration of about 0.02 M to about 0.04 M. In some embodiments, the pretreated suspension has a potassium sorbate concentration of about 0.005, 0.006, 0.007, 0.008, 0.009, 0.010, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.030, 0.035, 0.040, 0.045, 0.050, 0.055, 0.060, 0.070, 0.080, 0.090, or 0.10 M.

In some embodiments, the pretreated suspension comprises iodixanol. In some embodiments, the pretreated suspension has an iodixanol concentration of about 5% w/v to about 15% w/v. In some embodiments, the pretreated suspension has an iodixanol concentration of about 6% w/v to about 13% w/v. In some embodiments, the pretreated suspension has an iodixanol concentration of about 7% w/v to about 11% w/v. In some embodiments, the pretreated suspension has an iodixanol concentration of about 8% w/v to about 10% w/v.

In some embodiments, the pretreated suspension comprises sodium benzoate. In some embodiments, the pretreated suspension has a sodium benzoate has a concentration of about 0.01 M to about 0.6 M. In some embodiments, the pretreated suspension has a sodium benzoate has a concentration of about 0.02 M to about 0.5 M. In some embodiments, the pretreated suspension has a sodium benzoate has a concentration of about 0.03 M to about 0.4 M. In some embodiments, the pretreated suspension has a sodium benzoate has a concentration of about 0.04 M to about 0.3 M. In some embodiments, the pretreated suspension has a sodium benzoate has a concentration of about 0.05 M to about 0.2 M.

In some embodiments, a pretreated suspension comprises a combination of excipients selected from a thiosulfate, potassium sorbate, iodixanol, and sodium benzoate in a concentration described herein.

In some embodiments, the pretreated solution comprising thiosulfate, potassium sorbate, iodixanol, and/or sodium benzoate further comprises a polyvinyl alcohol (PVA). PVA is a water-soluble synthetic polymer and has the idealized formula [CH2CH(OH)]n. Any suitable PVA can be used in the pretreated suspension of the present disclosure. PVA types are known in the art and commercially available from several sources (Sigma-Aldrich, TCI, Alfa Aesar, VWR). In some embodiments, the PVA has an average molecular weight from about 9 kDa to about 186 kDa. In some embodiments, the PVA is PVA3 as described herein having a molecular weight of about 27 kDa. In some embodiments, the PVA is PVA10 as described herein having a molecular weight of about 13 kDA to about 23 kDa. In some embodiments, the pretreated suspension has a PVA concentration of about 0.01% w/v to about 0.75% w/v.

In some embodiments, the pretreated suspension comprising thiosulfate, potassium sorbate, iodixanol, and/or sodium benzoate further comprises NaCl. In some embodiments, the pretreated suspension has NaCl concentration of about 0.005 M to about 0.5 M. In some embodiments, the pretreated suspension has NaCl concentration of about 0.01 M to about 0.4 M. In some embodiments, the pretreated suspension has NaCl concentration of about 0.015 M to about 0.3 M. In some embodiments, the pretreated suspension has NaCl concentration of about 0.015 M to about 0.2 M. In some embodiments, the pretreated suspension has NaCl concentration of about 0.015 M to about 0.1 M. In some embodiments, the pretreated suspension has NaCl concentration of about 0.02 M to about 0.05 M. In some embodiments, the pretreated suspension has a NaCl concentration of about 1 mM to about 500 mM, about 2 mM to about 475 mM, about 3 mM to about 450 mM, about 4 mM to about 425 mM, about 5 mM to about 400 mM, about 6 mM to about 375 mM, about 7 mM to about 350 mM, about 8 mM to about 325 mM, about 9 mM to about 300 mM, about 10 mM to about 275 mM, about 15 mM to about 250 mM, about 20 mM to about 200 mM, about 25 mM to about 150 mM, about 30 mM to about 100 mM, about 35 mM to about 75 mM, about 40 mM to about 60 mM, about 45 mM to about 55 mM, or about 25 mM to about 75 mM.

In some embodiments, the pretreated suspension comprising thiosulfate, potassium sorbate, iodixanol, and/or sodium benzoate further comprises sucrose. In some embodiments, the pretreated suspension has a sucrose concentration of about 5% w/v to about 15% w/v. In some embodiments, the pretreated suspension has a sucrose concentration of about 7% w/v to about 11% w/v. In some embodiments, the pretreated suspension has a sucrose concentration of about 8% w/v to about 10% w/v.

In some embodiments, the liquid medium or pretreated suspension comprising thiosulfate, potassium sorbate, iodixanol, and/or sodium benzoate further comprises a buffer. In some embodiments, the buffer is selected from MOPS, HEPES, TRIS, MES, citrate, and phosphate buffered saline (PBS). In some embodiments, the buffer is in a concentration of about 7 mg/mL to about 15 mg/mL. In some embodiments, the liquid medium or the pretreated suspension has a pH of about 7.4. In some embodiments, the liquid medium or the pretreated suspension has a pH of about 7.0 to about 8.0.

In one embodiment, a liquid medium is provided comprising encapsulated RNA in a concentration of about 0.005 mg/mL to about 2.0 mg/mL, potassium sorbate in a concentration of about 0.005 M to about 0.5 M, a poloxamer in a concentration of about 0.005 to about 0.5% w/v, a sugar in a concentration of about 4% to about 22% w/v, NaCl in a concentration of about 5 mM to about 500 mM, and a buffer having a pH of about 7.4 to about 8.0 in a concentration of about 1 mM to about 300 mM. In some embodiments, the poloxamer is poloxamer 188 (aka, P188). In some embodiments, the sugar is sucrose. In some embodiments, the RNA is in a concentration of about 0.010 to about 1.5 mg/mL. In some embodiments, the RNA is in a concentration of about 0.050 to about 0.8 mg/mL. In some embodiments, the potassium sorbate is in a concentration of about 0.010 M to about 0.3 M. In some embodiments the potassium sorbate is in a concentration of about 0.015 M to about 0.1 M. In some embodiments, the poloxamer is in a concentration of about 0.10 to about 0.40% w/v. In some embodiments, the poloxamer is in a concentration of about 0.015 to about 0.30% w/v. In some embodiments, the poloxamer is in a concentration of about 0.020 to about 0.20% w/v. in some embodiments, the poloxamer is in a concentration of about 0.030 to about 0.10% w/v. In some embodiments, the sugar is in a concentration of about 8 to about 20% w/v. In some embodiments, the sugar is in a concentration of about 12 to about 20% w/v. In some embodiments, the sugar is in a concentration of about 16 to about 20% w/v. In some embodiments, the buffer is Tris. In some embodiments, the buffer is in a concentration of about 2 mM to about 250 mM. In some embodiments, the buffer is in a concentration of about 3 mM to about 200 mM. In some embodiments, the buffer is in a concentration of about 4 mM to about 150 mM. In some embodiments, the buffer is in a concentration of about 5 mM to about 100 mM. In some embodiments the buffer is in a concentration of about 8 mM to about 50 mM. In some embodiments the buffer is in a concentration of about 10 mM to about 40 mM. In some embodiments the buffer is in a concentration of about 12 mM to about 30 mM. In some embodiments the buffer is in a concentration of about 15 mM to about 25 mM.

Lyophilized Compositions

In another aspect, a lyophilized composition is provided comprising lipid nanoparticles encapsulating a nucleic acid and one or more excipients selected from potassium sorbate, thiosulfate, sodium benzoate, and iodixanol. In some embodiments, the nucleic acid is RNA. In some embodiments, the RNA is a mRNA. In some embodiments, the RNA is siRNA. In some embodiments, the RNA is self-replicating RNA.

In some embodiments, the lyophilized composition comprising potassium sorbate, thiosulfate, sodium benzoate, and/or iodixanol has a total lipid to nucleic acid weight ratio in the lyophilized composition of about 50:1 to about 10:1. In some embodiments, the lyophilized composition has a total lipid to nucleic acid weight ratio in the lyophilized composition of about 40:1 to about 20:1. In some embodiments, the lyophilized composition has a total lipid to nucleic acid weight ratio in the lyophilized composition of about 35:1 to about 25:1. In some embodiments, the lyophilized composition has a total lipid to nucleic acid weight ratio in the lyophilized composition of about 45:1 to about 30:1.

The potassium sorbate, thiosulfate, sodium benzoate, and/or iodixanol can be present in a weight ratio of the selected excipient to nucleic acid (e.g., RNA) described hereinbelow.

In some embodiments, the lyophilized composition comprises potassium sorbate in a weight ratio of potassium sorbate to nucleic acid of about 30:1 to about 250:1. In some embodiments, the lyophilized composition comprises potassium sorbate in a weight ratio of potassium sorbate to nucleic acid of about 40:1 to about 200:1. In some embodiments, the lyophilized composition comprises potassium sorbate in a weight ratio of potassium sorbate to nucleic acid of about 50:1 to about 175:1. In some embodiments, the lyophilized composition comprises potassium sorbate in a weight ratio of potassium sorbate to nucleic acid of about 5:1 to about 150:1. In some embodiments, the lyophilized composition comprises potassium sorbate in a weight ratio of potassium sorbate to nucleic acid of about 10:1 to about 125:1. In some embodiments, the lyophilized composition comprises potassium sorbate in a weight ratio of potassium sorbate to nucleic acid of about 15:1 to about 100:1. In some embodiments, the lyophilized composition comprises potassium sorbate in a weight ratio of potassium sorbate to nucleic acid of about 20:1 to about 80:1. In some embodiments, the lyophilized composition comprises potassium sorbate in a weight ratio of potassium sorbate to nucleic acid of about 25:1 to about 60:1. In some embodiments, the lyophilized composition comprises potassium sorbate in a weight ratio of potassium sorbate to nucleic acid of about 30:1 to about 50:1.

In some embodiments, lyophilized composition comprises sodium thiosulfate in a weight ratio of sodium thiosulfate to nucleic acid of about 1:1 to about 12:1. In some embodiments, the lyophilized composition comprises sodium thiosulfate in a weight ratio of sodium thiosulfate to nucleic acid of about 2:1 to about 10:1. In some embodiments, the lyophilized composition comprises sodium thiosulfate in a weight ratio of sodium thiosulfate to nucleic acid of about 3:1 to about 8:1.

In some embodiments, the lyophilized composition comprises sodium benzoate in a weight ratio of sodium benzoate to nucleic acid of about 1:1 to about 12:1. In some embodiments, the lyophilized composition comprises sodium benzoate in a weight ratio of sodium benzoate to nucleic acid of about 2:1 to about 10:1. In some embodiments, the lyophilized composition comprises sodium benzoate in a weight ratio of sodium benzoate to nucleic acid of about 3:1 to about 9:1.

In some embodiments, the lyophilized composition comprises iodixanol in a weight ratio of iodixanol to nucleic acid of about 100:1 to about 800:1. In some embodiments, the lyophilized composition comprises iodixanol in a weight ratio of iodixanol to nucleic acid of about 150:1 to about 750:1. In some embodiments, the lyophilized composition comprises iodixanol in a weight ratio of iodixanol to nucleic acid of about 200:1 to about 700:1. In some embodiments, the lyophilized composition comprises iodixanol in a weight ratio of iodixanol to nucleic acid of about 250:1 to about 650:1.

In some embodiments, the lyophilized composition comprising potassium sorbate, thiosulfate, sodium benzoate, and/or iodixanol further comprises polyvinyl alcohol (PVA) in a weight ratio of PVA to nucleic acid of about 1:1 to about 12:1.

In some embodiments, the lyophilized composition comprising potassium sorbate, thiosulfate, sodium benzoate, and/or iodixanol further comprises sucrose in a weight ratio of sucrose to nucleic acid of about 100:1 to about 800:1.

In some embodiments, the lyophilized composition comprising potassium sorbate, thiosulfate, sodium benzoate, and/or iodixanol further comprises a buffer selected from HEPES, MOPS, TRIS, MES, citrate, and phosphate in a weight ratio of buffer to nucleic acid of about 3:1 to about 150:1. In some embodiments, the buffer is TRIS.

In some embodiments, the lyophilized composition comprising potassium sorbate, thiosulfate, sodium benzoate, and/or iodixanol further comprises NaCl. In some embodiments, the lyophilized composition comprises about 0.5% w/w to about 5.0% w/w NaCl. In some embodiments, the lyophilized composition comprises about 0.6% w/w to about 4.5% w/w NaCl. In some embodiments, the lyophilized composition comprises about 0.7% w/w to about 4.0% w/w NaCl. In some embodiments, the lyophilized composition comprises about 0.8% w/w to about 3.5% w/w NaCl. In some embodiments, the lyophilized composition comprises about 0.9% w/w to about 3.0% w/w NaCl. In some embodiments, the lyophilized composition comprises about 1.0% w/w to about 2.5% w/w NaCl. In some embodiments, the lyophilized composition comprises about 1.1% w/w to about 2.4% w/w NaCl. In some embodiments, the lyophilized composition comprises about 1.2% w/w to about 2.3% w/w NaCl. In some embodiments, the lyophilized composition comprises about 1.3% w/w to about 2.1% w/w NaCl. In some embodiments, the lyophilized composition comprises about 1.4% w/w to about 2.0% w/w NaCl. In some embodiments, the lyophilized composition comprises about 1.4% w/w to about 1.6% w/w NaCl. In some embodiments, the lyophilized composition comprises about 0.75% w/w to about 2.25% w/w NaCl. In some embodiments, the lyophilized composition comprises about 1.0% w/w to about 2.0% w/w NaCl.

In some embodiments, the lyophilized composition comprises about 85 to about 96% w/w of a sugar. In some embodiments, the sugar is sucrose. In some embodiments, the lyophilized composition comprises about 88 to about 95% w/w of the sugar. In some embodiments, the lyophilized composition comprises about 90 to about 95% w/w of the sugar. In some embodiments, the lyophilized composition comprises about 85%, 86%, 87%, 88%, 89%, 90%, 91%, 92%, 93%, 94%, 95%, 96%, 97%, or 98% w/w of the sugar. For the foregoing percentage of the sugar, the term "about" shall mean to be ±0.5%.

In some embodiments, the lyophilized composition comprises about 0.01 to about 1.0% w/w of a poloxamer. In some embodiments, the lyophilized composition comprises about 0.02 to about 0.8% w/w of the poloxamer. In some embodiments, the lyophilized composition comprises about 0.03 to about 0.7% w/w of the poloxamer. In some embodiments, the lyophilized composition comprises about 0.04 to about 0.6% w/w of the poloxamer. In some embodiments, the lyophilized composition comprises about 0.05 to about 0.5% w/w of the poloxamer. In some embodiments, the lyophilized composition comprises about 0.06 to about 0.4% w/w of the poloxamer. In some embodiments, the lyophilized composition comprises about 0.07 to about 0.3% w/w of the poloxamer. In some embodiments, the lyophilized composition comprises about 0.09 to about 0.2% w/w of the poloxamer. In some embodiments, the poloxamer is poloxamer 188.

In one embodiment, a lyophilized composition is provided comprising lipid nanoparticles encapsulating an RNA, poloxamer, potassium sorbate, and a sugar. In some embodiments, the poloxamer is poloxamer 188. In some embodiments, the lyophilized composition comprises about 0.001 to about 1.0% w/w of the RNA. In some embodiments, the lyophilized composition comprises about 0.005 to about 0.8% w/w of the RNA. In some embodiments, the lyophilized composition comprises about 0.01 to about 0.5% w/w of the RNA. In some embodiments, the lyophilized composition comprises about 0.02 to about 0.4% w/w of the RNA. In some embodiments, the lyophilized composition comprises about 0.03 to about 0.3% w/w of the RNA. In some embodiments, the lyophilized composition comprises about 0.04 to about 0.2% w/w of the RNA. In some embodiments, the lyophilized composition comprises about 0.5 to about 5.0% w/w lipids. In some embodiments, the lyophilized composition comprises about 1.0 to about 4.0% w/w lipids. In some embodiments, the lyophilized composition comprises about 1.25 to about 3.0% w/w lipids. In some embodiments, the lyophilized composition comprises about 0.5 to about 2.5% w/w of TRIS buffer. In some embodiments, the lyophilized composition comprises about 0.75 to about 2.25% w/w of TRIS buffer. In some embodiments, the lyophilized composition comprises about 1.0 to about 2.0% w/w of TRIS buffer. In some embodiments, the lyophilized composition comprises about 0.75 to about 2.75% w/w of NaCl. In some embodiments, the lyophilized composition comprises about 1.0 to about 2.5% w/w of NaCl. In some embodiments, the lyophilized composition comprises about 1.25 to about 1.80% w/w of NaCl. In some embodiments, the lyophilized composition comprises about 85 to about 96% w/w of the sugar. In some embodiments, the lyophilized composition comprises about 88 to about 95% w/w of the sugar. In some embodiments, the lyophilized composition comprises about 90 to about 95% w/w of the sugar. In some embodiments, the sugar is sucrose. In some embodiments, the lyophilized composition comprises about 0.01 to about 1.0% w/w of the poloxamer. In some embodiments, the lyophilized composition comprises about 0.02 to about 0.8% w/w of the poloxamer. In some embodiments, the lyophilized composition comprises about 0.03 to about 0.7% w/w of the poloxamer. In some embodiments, the lyophilized composition comprises about 0.04 to about 0.6% w/w of the poloxamer. In some embodiments, the lyophilized composition comprises about 0.05 to about 0.5% w/w of the poloxamer. In some embodiments, the lyophilized composition comprises about 0.06 to about 0.4% w/w of the poloxamer. In some embodiments, the lyophilized composition comprises about 0.07 to about 0.3% w/w of the poloxamer. In some embodiments, the lyophilized composition comprises about 0.09 to about 0.2% w/w of the poloxamer. In some embodiments, the poloxamer is poloxamer 188. In some embodiments, the lyophilized composition comprises about 0.5 to about 5.0% w/w of potassium sorbate. In some embodiments, the lyophilized composition comprises about 0.75 to about 4.0% w/w of potassium sorbate. In some embodiments, the lyophilized composition comprises about 1.0 to about 3.0% w/w of potassium sorbate. In some embodiments, the lyophilized composition comprises about 1.25 to about 2.75% w/w of potassium sorbate.

Preservation, Reconstitution, and Administration of Lyophilized Compositions

A lyophilized composition prepared by a process described herein or a lyophilized composition described herein can be stably stored at higher temperatures than lipid nanoparticles suspensions. Typically, lipid nanoparticle suspensions are stored at −70° C., which is not a suitable temperature for transport and storage for facilities that lack equipment capable of achieving and maintaining this temperature. The lyophilized compositions can be stably stored at temperatures above 70° C. In some embodiments, a method of preserving a lyophilized composition is provided herein comprising storing a lyophilized product of the present disclosure at a temperature of about −20° C. to about 8° C. In some embodiments, the method comprises storing a lyophilized product of the disclosure at a temperature of about −20, −19, −18, −17, −16, −15, −14, −13, −12, −11, −10, −9, −8, −7, −6, −5, −4, −3, −2, −1, 0, 1, 2, 3, 4, 5, 6, 7, or 8° C. In some embodiments, the method comprises storing a lyophilized product of the present disclosure at a temperature of about −20° C. to about 8° C.

In some embodiments, a method of reconstituting a lyophilized composition of the present disclosure is provided comprising adding a liquid medium to the lyophilized composition.

In some embodiments, a method of treating a disease or disorder in a subject is provided comprising administering to the subject a lyophilized composition of the present disclosure reconstituted in a liquid medium. In some embodiments, the reconstituted lyophilized composition is administered intravenously. In some embodiments, the reconstituted lyophilized composition is administered intramuscularly. In some embodiments, the reconstituted lyophilized composition is administered via inhalation. Methods for intravenous, intramuscular, and inhalable administration are known in the art and readily adapted to the reconstituted formulations described herein.

Definitions

At various places in the present specification, substituents of compounds of the present disclosure are disclosed in groups or in ranges. It is specifically intended that the present disclosure include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "anionic lipid" means a lipid that is negatively charged at physiological pH. These lipids include, but are not limited to, phosphatidylglycerols, cardiolipins, diacylphosphatidylserines, diacylphosphatidic acids, N-dodecanoyl phosphatidylethanolamines, N-succinyl phosphatidylethanolamines, N-glutarylphosphatidylethanolamines, lysylphosphatidylglycerols, palmitoyloleyolphosphatidylglycerol (POPG), and other anionic modifying groups joined to neutral lipids.

The phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The terms "include," "have," or the like is used in the description or the claims, such term is intended to be inclusive in a manner similar to the term "comprise" as "comprise" is interpreted when employed as a transitional word in a claim.

The term "cationic lipid" means amphiphilic lipids and salts thereof having a positive, hydrophilic head group; one, two, three, or more hydrophobic fatty acid or fatty alkyl chains; and a connector between these two domains. An ionizable or protonatable cationic lipid is typically protonated (i.e., positively charged) at a pH below its $pK_a$ and is substantially neutral at a pH above the $pK_a$. Preferred ionizable cationic lipids are those having a pKa that is less than physiological pH, which is typically about 7.4. The cationic lipids of the disclosure may also be termed titratable cationic lipids. The cationic lipids can be an "amino lipid" having a protonatable tertiary amine (e.g., pH-titratable) head group. Some amino exemplary amino lipid can include $C_{18}$ alkyl chains, wherein each alkyl chain independently has 0 to 3 (e.g., 0, 1, 2, or 3) double bonds; and ether, ester, or ketal linkages between the head group and alkyl chains. Such cationic lipids include, but are not limited to, DSDMA, DODMA, DLinDMA, DLenDMA, γ-DLenDMA, DLin-K-DMA, DLin-K-C2-DMA (also known as DLin-C2K-DMA, XTC2, and C2K), DLin-K-C3-DM A, DLin-K-C4-DMA, DLen-C2K-DMA, y-DLen-C2K-DMA, DLin-M-C2-DMA (also known as MC2), DLin-M-C3-DMA (also known as MC3) and (DLin-MP-DMA)(also known as 1-Bl 1).

The term "comprising" is intended to be open and permits but does not require the inclusion of additional elements or steps. When the term "comprising" is used herein, the term "consisting of" is thus also encompassed and disclosed.

The term "composition" means a product comprising the specified ingredients in the specified amounts, as well as any product that results, directly or indirectly, from combination of the specified ingredients in the specified amounts.

The term "commercially available chemicals" and the chemicals used in the Examples set forth herein may be obtained from standard commercial sources, where such sources include, for example, Acros Organics (Pittsburgh, Pa.), Sigma-Adrich Chemical (Milwaukee, Wis.), Avocado Research (Lancashire, U.K.), Bionet (Cornwall, U.K.), Boron Molecular (Research Triangle Park, N.C.), Combi-Blocks (San Diego, Calif.), Eastman Organic Chemicals, Eastman Kodak Company (Rochester, N.Y.), Fisher Scientific Co. (Pittsburgh, Pa.), Frontier Scientific (Logan, Utah), ICN Biomedicals, Inc. (Costa Mesa, Calif), Lancaster Synthesis (Windham, N.H.), Maybridge Chemical Co. (Cornwall, U.K.), Pierce Chemical Co. (Rockford, Ill.), Riedel de Haen (Hannover, Germany), Spectrum Quality Product, Inc. (New Brunswick, N.J.), TCI America (Portland, Oreg.), and Wako Chemicals USA, Inc. (Richmond, Va.).

The phrase "compounds described in the chemical literature" may be identified through reference books and databases directed to chemical compounds and chemical reactions, as known to one of ordinary skill in the art. Suitable reference books and treatise that detail the synthesis of reactants useful in the preparation of compounds disclosed herein, or provide references to articles that describe the preparation of compounds disclosed herein, include for example, "Synthetic Organic Chemistry", John Wiley and Sons, Inc. New York; S. R. Sandler et al, "Organic Functional Group Preparations," 2nd Ed., Academic Press, New York, 1983; H. O. House, "Modern Synthetic Reactions," 2nd Ed., W. A. Benjamin, Inc. Menlo Park, Calif, 1972; T. L. Glichrist, "Heterocyclic Chemistry," 2nd Ed. John Wiley and Sons, New York, 1992; J. March, "Advanced Organic Chemistry: reactions, Mechanisms and Structure," 5th Ed., Wiley Interscience, New York, 2001; Specific and analogous reactants may also be identified through the indices of known chemicals prepared by the Chemical Abstract Service of the American Chemical Society, which are available in most public and university libraries, as well as through online databases (the American Chemical Society, Washington, D.C. may be contacted for more details). Chemicals that are known but not commercially available in catalogs may be prepared by custom chemical synthesis houses, where many of the standard chemical supply houses (such as those listed above) provide custom synthesis services.

The term "effective amount" of an agent, as used herein, is that amount sufficient to effect beneficial or desired results, for example, clinical results, and, as such, an "effective amount" depends upon the context in which it is being applied. For example, in the context of administering an agent that treats cancer, an effective amount of an agent is, for example, an amount sufficient to achieve treatment, as defined herein, of cancer, as compared to the response obtained without administration of the agent.

The term "fully encapsulated" means that the nucleic acid (e.g., mRNA) in the nucleic acid-lipid particle is not significantly degraded after exposure to serum or a nuclease assay that would significantly degrade free RNA. When fully encapsulated, preferably less than 25% of the nucleic acid in the particle is degraded in a treatment that would normally degrade 100% of free nucleic acid, more preferably less than 10%, and most preferably less than 5% of the nucleic acid in the particle is degraded. "Fully encapsulated" also means that the nucleic acid-lipid particles do not rapidly decompose into their component parts upon in vivo administration.

The term "nucleic acid" means deoxyribonucleotides or ribonucleotides and polymers thereof in single- or double-stranded form. The term encompasses nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, without limitation, phosphorothioates, phosphoramidates, methyl phosphonates, chiral-methyl phosphonates, 2'-O-methyl ribonucleotides, peptide-nucleic acids (PNAs).

The term "compound," is meant to include all stereoisomers, geometric isomers, tautomers, and isotopes of the structures depicted.

The term "delivery" refers to the act or manner of delivering a compound, substance, entity, moiety, cargo or payload.

The term "delivery agent" or "delivery vehicle" refers to any substance which facilitates, at least in part, the in vivo delivery of a polynucleotide to targeted cells.

The term "expression" of a nucleic acid sequence refers to one or more of the following events: (1) production of an RNA template from a DNA sequence (e.g., by transcription); (2) processing of an RNA transcript (e.g., by splicing, editing, 5' cap formation, and/or 3' end processing); (3) translation of an RNA into a polypeptide or protein; and (4) post-translational modification of a polypeptide or protein.

The term "feature" refers to a characteristic, a property, or a distinctive element.

The term "hydrophobic lipids" means compounds having apolar groups that include, but are not limited to, long-chain saturated and unsaturated aliphatic hydrocarbon groups and such groups optionally substituted by one or more aromatic, cycloaliphatic, or heterocyclic group(s). Suitable examples include, but are not limited to, diacylglycerol, dialkylglycerol, N—N-dialkylamino, 1,2-diacyloxy-3-aminopropane, and 1,2-dialkyl-3-aminopropane.

The term "lipid" means an organic compound that comprises an ester of fatty acid and is characterized by being insoluble in water, but soluble in many organic solvents. Lipids are usually divided into at least three classes: (1) "simple lipids," which include fats and oils as well as waxes; (2) "compound lipids," which include phospholipids and glycolipids; and (3) "derived lipids" such as steroids.

The term "lipid delivery vehicle" means a lipid formulation that can be used to deliver a therapeutic nucleic acid (e.g., mRNA) to a target site of interest (e.g., cell, tissue, organ, and the like). The lipid delivery vehicle can be a nucleic acid-lipid particle, which can be formed from a cationic lipid, a non-cationic lipid (e.g., a phospholipid), a conjugated lipid that prevents aggregation of the particle (e.g., a PEG-lipid), and optionally cholesterol. Typically, the therapeutic nucleic acid (e.g., mRNA) may be encapsulated in the lipid portion of the particle, thereby protecting it from enzymatic degradation.

The term "lipid encapsulated" means a nucleic acid such as an mRNA that is completely encapsulated, partial encapsulated, or both in a lipid formulation. In a preferred embodiment, the nucleic acid (e.g., mRNA) is fully encapsulated in the lipid particle.

The term "lipid conjugate" means a conjugated lipid that inhibits aggregation of lipid particles. Such lipid conjugates include, but are not limited to, PEG-lipid conjugates such as, e.g., PEG coupled to dialkyloxypropyls (e.g., PEG-DAA conjugates), PEG coupled to diacylglycerols (e.g., PEG-DAG conjugates), PEG coupled to cholesterol, PEG coupled to phosphatidylethanolamines, and PEG conjugated to ceramides, cationic PEG lipids, polyoxazoline (POZ)-lipid conjugates, polyamide oligomers, and mixtures thereof. PEG or POZ can be conjugated directly to the lipid or may be linked to the lipid via a linker moiety. Any linker moiety suitable for coupling the PEG or the POZ to a lipid can be used including, e.g., non-ester-containing linker moieties and ester-containing linker moieties. In certain preferred embodiments, non-ester-containing linker moieties, such as amides or carbamates, are used.

The term "amphipathic lipid" or "amphiphilic lipid" means the material in which the hydrophobic portion of the lipid material orients into a hydrophobic phase, while the hydrophilic portion orients toward the aqueous phase. Hydrophilic characteristics derive from the presence of polar or charged groups such as carbohydrates, phosphate, carboxylic, sulfato, amino, sulfhydryl, nitro, hydroxyl, and other like groups. Hydrophobicity can be conferred by the inclusion of apolar groups that include, but are not limited to, long-chain saturated and unsaturated aliphatic hydrocarbon groups and such groups substituted by one or more aromatic, cycloaliphatic, or heterocyclic group(s). Examples of amphipathic compounds include, but are not limited to, phospholipids, aminolipids, and sphingolipids.

The term "messenger RNA" (mRNA) refers to any polynucleotide which encodes a protein or polypeptide of interest and which is capable of being translated to produce the encoded protein or polypeptide of interest in vitro, in vivo, in situ or ex vivo.

The term "nucleotide" is meant to include nucleotides that have natural bases (standard) or modified bases well known in the art. Such bases are generally located at the 1' position of a nucleotide sugar moiety. Nucleotides generally comprise a base, sugar, and a phosphate group. The nucleotides can be unmodified or modified at the sugar, phosphate, and/or base moiety, (also referred to interchangeably as nucleotide analogs, modified nucleotides, non-natural nucleotides, non-standard nucleotides and other; see, for example, Usman and McSwiggen, supra; Eckstein, et al., International PCT Publication No. WO 92/07065; Usman, et al., International PCT Publication No. WO 93/15187; Uhlman & Peyman). There are several examples of modified nucleic acid bases known in the art as summarized by Limbach, et al, Nucleic Acids Res. 22:2183, 1994. Some of the non-limiting examples of base modifications that can be introduced into nucleic acid molecules include: inosine, purine, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g., 6-methyluridine), propyne, and others (Burgin, et al., Biochemistry 35:14090, 1996; Uhlman & Peyman, supra). By "modified bases" in this aspect is meant nucleotide bases other than adenine, guanine, cytosine, and uracil at 1' position or their equivalents.

The term "patient" refers to a subject who may seek or be in need of treatment, requires treatment, is receiving treatment, will receive treatment, or a subject who is under care by a trained professional for a particular disease or condition.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspending or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

The phrase "pharmaceutically acceptable salts" refers to derivatives of the disclosed compounds wherein the parent compound is modified by converting an existing acid or base moiety to its salt form (e.g., by reacting the free base group with a suitable organic acid). Examples of pharmaceutically acceptable salts include, but are not limited to, mineral or organic acid salts of basic residues such as amines; alkali or organic salts of acidic residues such as carboxylic acids; and the like. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts, and the like. Representative alkali or alkaline earth metal salts include sodium, lithium, potassium, calcium, magnesium, and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine, and the like. The pharmaceutically acceptable salts of the present disclosure include the conventional non-toxic salts of the parent compound formed, for example, from non-toxic inorganic or organic acids. The pharmaceutically acceptable salts of the present disclosure can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

The terms "purify," "purified," "purification" means to make substantially pure or clear from unwanted components, material defilement, admixture or imperfection.

The terms "significant" or "significantly" are used synonymously with the term "substantially."

The term "stable" refers to a compound that is sufficiently robust to survive isolation to a useful degree of purity from a reaction mixture, and preferably capable of formulation into an efficacious therapeutic agent.

The terms "stabilize", "stabilized," "stabilized region" means to make or become stable.

The term "substantially" refers to the qualitative condition of exhibiting total or near-total extent or degree of a characteristic or property of interest. One of ordinary skill in the biological arts will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

The term "treating" refers to partially or completely alleviating, ameliorating, improving, relieving, delaying onset of, inhibiting progression of, reducing severity of, and/or reducing incidence of one or more symptoms or features of a particular infection, disease, disorder, and/or condition. For example, "treating" cancer may refer to inhibiting survival, growth, and/or spread of a tumor. Treatment may be administered to a subject who does not exhibit signs of a disease, disorder, and/or condition and/or to a subject who exhibits only early signs of a disease, disorder, and/or condition for the purpose of decreasing the risk of developing pathology associated with the disease, disorder, and/or condition.

The term "in vitro" refers to events that occur in an artificial environment, e.g., in a test tube or reaction vessel, in cell culture, in a Petri dish, etc., rather than within an organism (e.g., animal, plant, or microbe).

The term "in vivo" refers to events that occur within an organism (e.g., animal, plant, or microbe or cell or tissue thereof).

The term "neutral lipid" means a lipid species that exist either in an uncharged or neutral zwitterionic form at a selected pH. At physiological pH, such lipids include, for example, diacylphosphatidylcholine, diacylphosphatidylethanolamine, ceramide, sphingomyelin, cephalin, cholesterol, cerebrosides, and diacylglycerols.

The term "non-cationic lipid" means an amphipathic lipid, a neutral lipid or anionic lipid as described herein.

The term "oligomer" may be used interchangeably with "polynucleotide" and refers to a molecule comprising at least two monomers and includes oligonucleotides such as DNAs and RNAs. In the case of oligomers containing RNA monomers and/or unlocked nucleic acid (UNA) monomers, the oligomers of the present disclosure may contain sequences in addition to the coding sequence (CDS). These additional sequences may be untranslated sequences, i.e., sequences which are not converted to protein by a host cell. These untranslated sequences can include a 5' cap, a 5' untranslated region (5' UTR), a 3' untranslated region (3' UTR), and a tail region, e.g., a polyA tail region. As described in further detail herein, any of these untranslated sequences may contain one or more UNA monomers—these UNA monomers are not capable of being translated by a host cell's machinery. In the context of the present disclosure, a "mRNA sequence", a "mRNA sequence", "translatable polynucleotide", or "translatable compound" refers to a sequence that comprises a region, e.g., the coding region of an RNA (e.g., the coding sequence of human cystic fibrosis transmembrane conductance regulator (CFTR) or a codon-optimized version thereof), that is capable of being converted to a protein or a fragment thereof, e.g., the human CFTR protein or a fragment thereof.

The terms "subject" refers to any organism to which a composition in accordance with the disclosure may be administered, e.g., for experimental, diagnostic, prophylactic, and/or therapeutic purposes. Typical subjects include animals (e.g., mammals such as mice, rats, rabbits, non-human primates, and humans) and/or plants.

EXAMPLES

Additional embodiments of the present disclosure are illustrated in further detail in the following examples, which are not in any way intended to limit the scope of the claims.

Example 1: Materials and Methods Generally

The experiments conducted in the examples described herein were conducted using lipid nanoparticle compositions that were manufactured according to well-known processes, for example, those described in U.S. application Ser. No. 16/823,212, the contents of which are incorporated by reference for the specific purpose of teaching lipid nanoparticle manufacturing processes. The lipid nanoparticle compositions and the lyophilized products were characterized for several properties. The materials and methods for these characterization process as well as a general method of manufacturing the lipid nanoparticle compositions that were used for lyophilization experiments are provided in this example.

Lipid Nanoparticle Manufacture

Lipid nanoparticle formulations used in the Examples were manufactured by mixing lipids (cationic lipid:helper lipid:cholesterol:PEG-lipid) in ethanol with RNA dissolved in citrate buffer. The mixed material was instantaneously diluted with phosphate buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 10-300 (for example, 40-60) mM NaCl and 5-15% sucrose, pH 7.3. The formulation was concentrated followed by 0.2 μm filtration using polyethersuflone (PES) filters. The RNA concentration in the formulation was then measured by RIBOGREEN™ fluorimetric assay, and the concentration was adjusted to a final desired concentration by diluting with HEPES buffer containing 10-100 (for example 40-60) mM NaCl, 0-15% sucrose, pH 7.2-8.5 containing glycerol. If not used immediately for further studies, the final formulation was then filtered through a 0.2 μm filter and filled into glass vials, stoppered, capped and placed at −70±5° C. The lipid nanoparticles formulations were characterized for their pH and osmolality. Lipid content and RNA content were measured by high performance liquid chromatography (HPLC), and mRNA integrity by was measured by fragment analyzer.

Dynamic Light Scattering (DLS)

The average particle size (z) and polydispersity index (PDI) of lipid nanoparticle formulations used in the Examples was measured by dynamic light scattering on a Malvern Zetasizer Nano ZS (United Kingdom).

RIBOGREEN™ Assay

The encapsulation efficiency of the lipid nanoparticle formulations was characterized using the RIBOGREEN™ fluorometric assay, which is a proprietary fluorescent dye (Molecular Probes/Invitrogen a division of Life Technologies, now part of Thermo Fisher Scientific of Eugene, Oregon, United States) that is used in the detection and quantification of nucleic acids, including both RNA and DNA. In its free form, RIBOGREEN™ exhibits little fluorescence and possesses a negligible absorbance signature. When bound to nucleic acids, the dye fluoresces with an intensity that is several orders of magnitude greater than the unbound form. The fluorescence can be then be detected by a sensor (fluorimeter) and the nucleic acid can be quantified.

Western Blot

In vivo efficacy of lipid nanoparticle formulations was tested by measuring applicable protein expression or knock-down activity using a Western blot assay. In the assay, 96-well collagen plates were used to seed cells transfected by the applicable lipid nanoparticle formulation at the appropriate density in Dulbecco's Modified Eagle Media (DMEM)/Fetal Bovine Serum (FBS) culture media. At the optimal confluence, the cells were transfected with a lipid nanoparticle formulation and diluted in the transfection reagent mix (MessengerMax and Opti-MEM). The cells were then placed in a $CO_2$ incubator and allowed to grow. At the desire timepoint, media was removed, and cells were fixed in 4% fresh paraformaldehyde (PFA) for 20 min. After that, fixative was removed, and cells were permeabilized several times in Tris buffered saline with Tris-buffered saline with 0.1% TWEEN® 20 detergent (TBST) for 5 minutes each time. When the permeabilization washes were complete, the cells were incubated with a blocking buffer (ODYSSEY® Blocking Buffer (PBS) (Li-Cor, Lincoln, NE)) for 45 min. Primary antibody was then added and incubated for 1 hour at room temperature. The cells were then washed several times in TBST and incubated for 1 hour with a secondary antibody diluted in blocking buffer and containing a CellTag™ 700 stain. Finally, the cells were washed several times in TBST followed by a last wash in Tris-buffered saline (TBS). The plate was imaged using the Licor (Lincoln, Nebraska USA) detection system, and data was normalized to the total number of cells labeled by the CellTag™ 700.

Example 2: Evaluation of Various Excipients (Lyoprotectants) in Pretreatment Suspension Experiments were conducted to evaluate the effect of various excipients on the quality of lyophilized product for lipid nanoparticle formulations prepared as described in Example 1. The quality of lyophilized lipid nanoparticle formulations was assessed by analyzing the formulations post-lyophilization and comparing this to the lipid nanoparticle formulation prior to lyophilization as well as after a conventional freeze/thaw cycle (i.e., frozen at ~−70° C. then allowed to thaw at room temperature).

The analysis of the lipid nanoparticle formulations included the analysis of particle size and polydispersity (PDI) and encapsulation efficiency (% Encap). The particles size post-lyophilization was compared to the particle size pre-lyophilization and the difference is reported as a delta (δ). The various compositions tested were screened as to whether a threshold of properties was met including minimal particle size increase (δ<10 nm), the maintenance of PDI (<0.2), and maintain high encapsulation efficiency (>85%).

The lyophilized lipid nanoparticle formulations were prepared by first pretreating a suspension of lipid nanoparticle formulation prepared according to Example 1 post-filtration by adding the excipients identified below to achieve the listed concentrations. A lyophilization cycle of a slow freezing gradient with primary drying conducted at −20° C., followed by secondary drying at 25° C. was applied. The lyophilization cycle was carried out in a Millrock Revo Freeze Dryer (Model No. RV85S4), using aliquots of 2.0 mL of suspension having a lipid nanoparticle concentration of 0.25 mg RNA/mL. Post-lyophilization the lyophilized product was reconstituted in 2.0 mL of water and analyzed as described above.

The excipients investigated in the presently disclosed studies are listed in Tables 1 below.

TABLE 1

List of Excipients Studied

| Excipient No. | Excipient | Description | Vendor | Product No. |
|---|---|---|---|---|
| 1 | PVA1 | MW 89,000-98,000, 99+% hydrolyzed | Sigma-Aldrich | 341584 |
| 2 | PVA2 | MW ~67,000 | Sigma-Aldrich | 81383 |
| 3 | PVA3 | MW ~27,000 | Sigma-Aldrich | 81382 |
| 4 | PVA4 | MW 146,000-186,000, 99+% hydrolyzed | Sigma-Aldrich | 363065 |
| 5 | PVA5 | MW 85,000-124,000, 99+% hydrolyzed | Sigma-Aldrich | 363146 |
| 6 | PVA6 | MW 130,000, 99+% hydrolyzed | Sigma-Aldrich | 563900 |
| 7 | PVA7 | Fully hydrolyzed | Sigma-Aldrich | p 1763 |
| 8 | PVA8 | MW 9,000-10,000, 80% hydrolyzed | Sigma-Aldrich | 360627 |
| 9 | PVA9 | MW 13,000-23,000, 87-89% hydrolyzed | Sigma-Aldrich | 363170 |
| 10 | PVA10 | average MW 13,000-23,000, 98% hydrolyzed | Sigma-Aldrich | 348406 |
| 11 | PVA11 | Poly(vinyl Alcohol), n = 1750 +/− 50 | TCI | P0469 |
| 12 | PVA12 | n = 2,000 (degree of saponification ~80 mol %) | TCI | P0804 |
| 13 | PVA13 | 86-89% hydrolyzed, low molecular weight | AlfaAesar | 41238 |
| 14 | PVA14 | | VWR | 10118-162 |
| 15 | PVA15 | M.W. ~10,000-26,000, 98-99% hydrolyzed | AlfaAesar | 41241 |
| 16 | Sucrose | | | |
| 17 | Trehalose | | | |
| 18 | NaCl | Sodium Chloride | | |
| 19 | KS | Potassium Sorbate | | |
| 20 | NaB | Sodium Benzoate | | |
| 21 | $(NH_4)_2SO_4$ | Ammonium Sulfate | | |
| 22 | Pro | L-Proline | | |
| 23 | PS20 | Polysorbate20 | | |
| 24 | PS80 | Polysorbate80 | | |
| 25 | P188 | Kolliphore P188 | | |
| 26 | P HS15 | Kolliphore HS15 | | |
| 27 | PVP | Polyvinylpyrrolidone K30 | | |
| 28 | HA | Human Serum Albumin | | |
| 29 | Iodixanol | | | |
| 30 | NaA | Sodium Ascorbate | | |
| 31 | NaS | Sodium Saccharin | | |

Two of the above excipients, human albumin (HA) and polyvinyl alcohol 1 (PVA1) were used for initial evaluation with the parameters and results listed in Table 2 below. Comparative formulations in which no excipients or having glycerol were also studied.

TABLE 2

Conditions and Results of Study

| | | Pre freeze | | Freeze Thaw | | Reconstituted | | |
|---|---|---|---|---|---|---|---|---|
| | Excipients | Size | PDI | Size | PDI | Size | PDI | δ |
| Group 1 | 10% HA | 59.05 | 0.236 | 189.6 | 0.178 | 217.9 | 0.384 | 158.85 |
| Group 2 | 5% HA | 58.37 | 0.156 | 81.86 | 0.248 | 132.8 | 0.479 | 74.43 |
| Group 3 | 2.5% HA | 60.83 | 0.139 | 65.8 | 0.17 | 81.3 | 0.348 | 20.47 |
| Group 4 | 1.0% HA | 61.28 | 0.12 | 62.46 | 0.114 | 79.7 | 0.259 | 18.42 |
| Group 5 | 0.5% HA | 62.25 | 0.1 | 62.02 | 0.109 | 83.34 | 0.227 | 21.09 |
| Group 6 | 1% PVA1 | 62.72 | 0.117 | 85.41 | 0.158 | 262.4 | 0.361 | 199.68 |
| Group 7 | 0.5% PVA1 | 61.37 | 0.082 | 71.18 | 0.055 | 99.68 | 0.095 | 38.31 |
| Group 8 | 0.1% PVA1 | 61.13 | 0.102 | 67.78 | 0.082 | 89.92 | 0.062 | 28.79 |

TABLE 2-continued

| | | Pre freeze | | Freeze Thaw | | Reconstituted | | |
|---|---|---|---|---|---|---|---|---|
| | Excipients | Size | PDI | Size | PDI | Size | PDI | δ |
| Group 9 | 0.05% PVA1 | 59.81 | 0.087 | 68.18 | 0.035 | 85.76 | 0.095 | 25.95 |
| Group 10 | 5% Glycerol | 62.11 | 0.072 | 59.56 | 0.093 | 295.6 | 0.405 | 233.49 |
| Group 11 | No Excipients | 61.22 | 0.078 | 67.82 | 0.086 | 101.1 | 0.251 | 39.88 |

Conditions and Results of Study

As seen in the Table 2, the lyophilization cycle and excipients tested did not produce lipid nanoparticle formulations with adequate properties. A concentration of 1.0% w/v for HA and 0.05% w/v PVA1 provided the best results.

Example 3: Evaluation of the Effect of Lipid Nanoparticle Concentration

Additional experiments were conducted to study the effect of lipid nanoparticle concentration (measured as the concentration of RNA in the suspension), buffer concentration, salt concentration, cryoprotectant concentration and lyoprotectant concentration (poloxamer) on the quality and properties of the lyophilized product.

The parameters were studied in nine different lyophilization experiments outlined in Table 3 below. The lyophilized lipid nanoparticle formulations were prepared by first pretreating a suspension of lipid nanoparticle formulation comprising a siRNA of about 21 nucleotides prepared according to Example 1 post-filtration to comprise the excipients and conditions listed in Table 3. After pretreatment, the pretreated formulations were lyophilized under conditions similar to those described in Example 2. Each of the experiments 1-9 listing in Table 3 were conducted at lipid nanoparticle concentrations of 0.25 mg/mL, 0.5 mg/mL, 1.0 mg/mL, and 2.0 mg/mL. The resulting lyophilized compositions were then reconstituted and characterized for their particle size, percent encapsulation, and PDI.

TABLE 3

Lyophilization Experimental Conditions

| Experiment# | Cryoprotectant (Glycerol) | Buffer (HEPES) | Salt (NaCl) | Poloxamer (P188) |
|---|---|---|---|---|
| 1 | 10% (A1) | 5 mM (B1) | 0 mM (C1) | 0% (D1) |
| 2 | 10% (A1) | 10 mM (B2) | 50 mM (C2) | 0.1% (D2) |
| 3 | 10% (A1) | 15 mM (B3) | 100 mM (C3) | 0.2% (D3) |
| 4 | 20% (A2) | 5 mM (B1) | 50 mM (C2) | 0.2% (D3) |
| 5 | 20% (A2) | 10 mM (B2) | 100 mM (C3) | 0% (D1) |
| 6 | 20% (A2) | 15 mM (B3) | 0 mM (C1) | 0.1% (D2) |
| 7 | 15% (A3) | 5 mM (B1) | 100 mM (C3) | 0.1% (D2) |
| 8 | 15% (A3) | 10 mM (B2) | 0 mM (C1) | 0.2% (D3) |
| 9 | 15% (A3) | 15 mM (B3) | 50 mM (C2) | 0% (D1) |

The results of the 1 mg lipid nanoparticle/mL study are shown in FIG. 1 It can be seen that for the particle size parameters A3, B2, C1/C3, and D2 showed the smallest particle size with A3 showing the best overall particle size. For percent encapsulation, parameters A3, B2, C1, and D1 showed the best results for their respective excipient group, with D1 showing the best percent encapsulation overall. Finally, for polydispersity (PDI), parameters A3, B2, C3, and D1 showed the best PDI for their respective excipient groups, with C3 showing the best PDI overall. These experiment thus determined that for the given excipients a composition comprising A3 (15% glycerol), B2 (10 mM Buffer), C1 (0 mM Salt), and D1/D2 (0%-0.1% Poloxamer) would provide the best result. This same analysis was also conducted for the concentrations of lipid nanoparticle tested, and the optimal conditions found for each concentration are shown in Table 4.

TABLE 4

Results of Lyophilization Study for Different Lipid Nanoparticle Concentrations

| Concentration (mg/mL) | Optimal Conditions | Cryoprotectant (%) | Buffer (mM) | Salt (mM) | Poloxamer (%) | Condition # |
|---|---|---|---|---|---|---|
| 0.25 | A3, B2, C1/C2, D1/D2 | 15 | 10 | 0 or 50 | 0 | Condition 1 |
| 0.5 | A3, B2, C2, D1/D2 | 15 | 10 | 50 | 0 or 0.1 | Condition 2 |
| 1 | A3, B2, C1, D2 | 15 | 10 | 0 | 0.2 | Condition 3 |
| 2 | A3, B3, C1, D2 | 15 | 15 | 0 | 0.2 | Condition 4 |

Figure 2A:
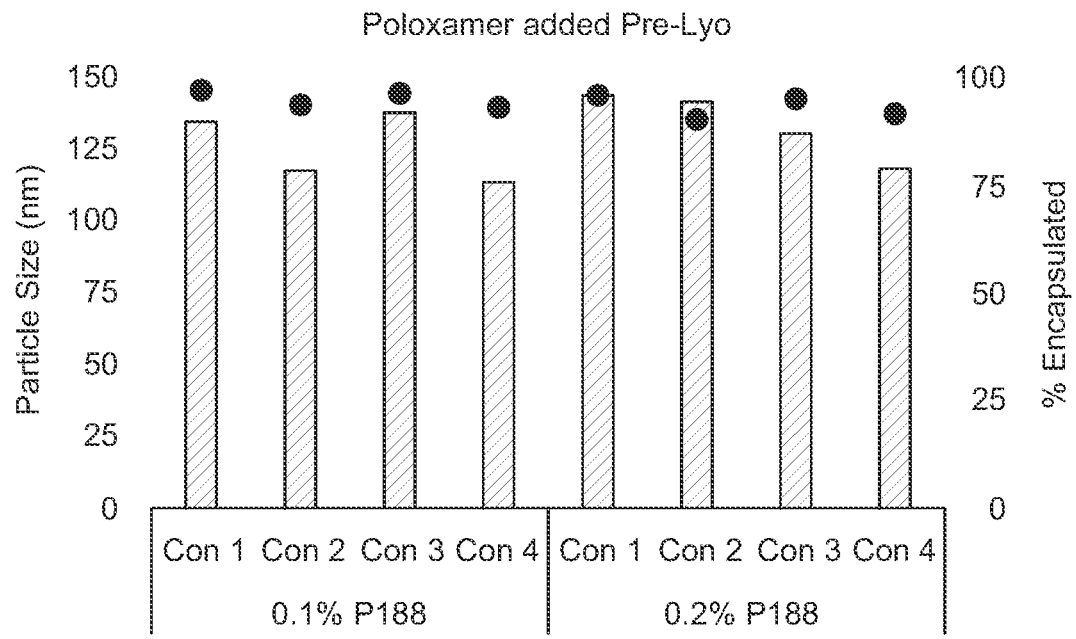
FIG. 2A shows particle size measurements (bar chart) and percent encapsulation (circles) for formulations prepared using P188 poloxamer (KOLLIPHOR® P 188) added to the suspension pre-lyophilization as described in Example 3.
Figure 2B:
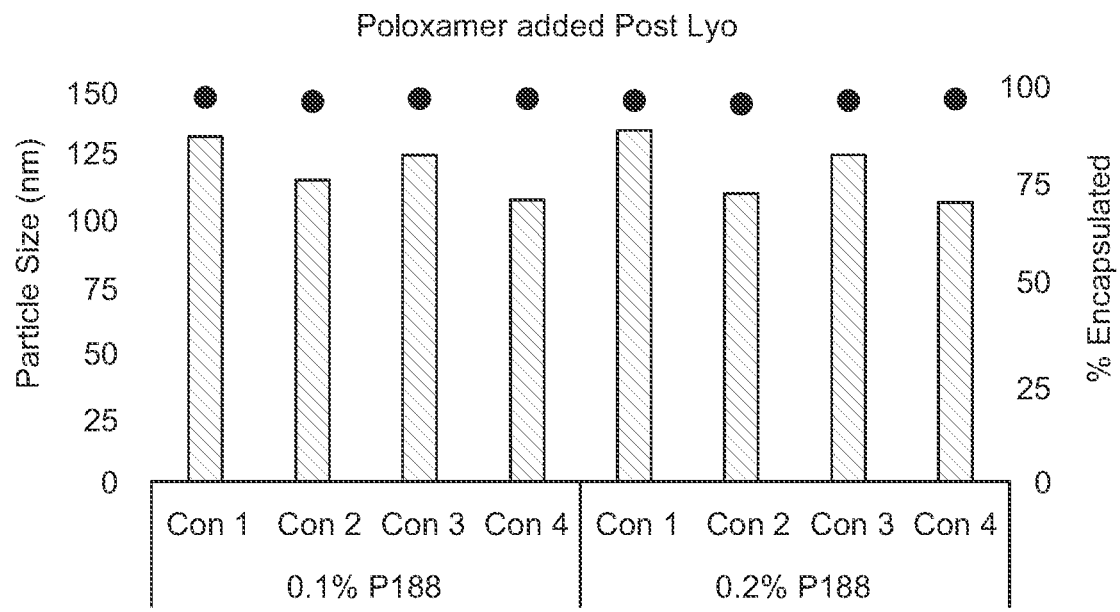
FIG. 2B shows particle size measurements (bar chart) and percent encapsulation (circles) for formulations prepared using P188 poloxamer (KOLLIPHOR® P 188) added to the formulation post-lyophilization as described in Example 3.

Further studies were conducted, to determine the effect of adding poloxamer (lyoprotectant) pre- versus post-lyophilization at concentrations of 0.1% and 0.2% P188 for Conditions 1-4. FIG. 2A shows the results for the pre-lyophilization experiment while FIG. 2B shows the results for the post-lyophilization experiment. It can be seen that adding poloxamer post-lyophilization (as part of reconstitution) was found to be the best at maintaining the percent encapsulation (shown as circles in the charts).

Figure 3:
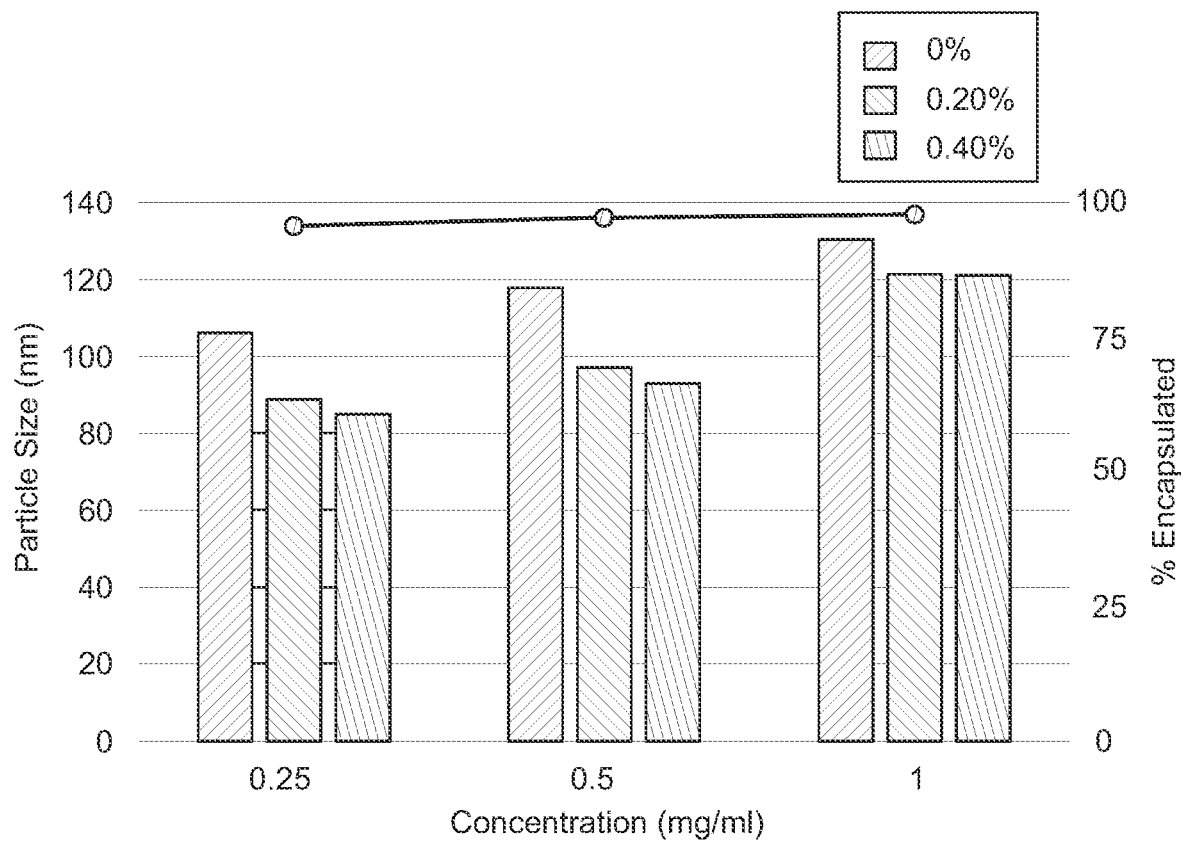
FIG. 3 shows the concentration dependence for lipid nanoparticle concentration (0.25, 0.5, and 1.0 mg RNA/mL) for particle size (bar chart) and percent encapsulation (circles) for P188 formulations treated post-lyophilization at different concentrations of P188 as described in Example 3.

Finally, FIG. 3 shows the results for characterizing lipid nanoparticle formulations that were treated with poloxamer post-lyophilization under the different concentrations of lipid nanoparticle. It can be seen that at a concentration of about 0.25 mg/mL, a particle size of about 85 nm was observed, while larger particle sizes were observed at higher concentrations. The percent encapsulation is shown as a bar curve in this figure and shows good encapsulation for each of the formulations.

Example 4: Evaluation of Two Additional PVA Excipients

After the results were obtained from Examples 2 and 3, further studies were conducted to compare the effect of other PVA excipients on the lyophilized product. The two PVA excipients were PVA2 and PVA3 as described in Table 1 above. The conditions and results of the experiment are provided in Table 5 below. In these experiments, the lyophilization cycle of Example 2 was repeated with the exception that the primary drying temperature was changed to −25° C.

TABLE 5

Conditions and Results of Evaluation for Two Additional PVA Excipients

|  | Excipients | Pre-lyophilization Size (nm) | PDI | Reconstituted Size (nm) | PDI | δ | % Encap |
|---|---|---|---|---|---|---|---|
| Group 1 | 2.5% HA | 63.47 | 0.111 | 77.77 | 0.304 | 14.3 | 47.41 |
| Group 2 | 1.0% HA | 62.96 | 0.117 | 75.85 | 0.208 | 12.89 | 43.27 |
| Group 3 | 0.5% HA | 63.3 | 0.084 | 77.52 | 0.195 | 14.22 | 43.02 |
| Group 4 | 1.0% HA | 64.45 | 0.114 | 79.52 | 0.174 | 15.07 | 55.75 |
| Group 5 | 0.1% PVA1 | 64.36 | 0.069 | 86.83 | 0.078 | 22.47 | 73.72 |
| Group 6 | 0.05% PVA1 | 64.65 | 0.071 | 87.13 | 0.071 | 22.48 | 73.26 |
| Group 7 | 0.5% PVA2 | 64.3 | 0.074 | 125.3 | 0.168 | 61 | 42.88 |
| Group 8 | 0.1% PVA2 | 63.95 | 0.081 | 96.15 | 0.269 | 32.2 | 42.89 |
| Group 9 | 0.05% PVA2 | 64.5 | 0.087 | 105.4 | 0.293 | 40.9 | 42.38 |
| Group 10 | 0.5% PVA3 | 63.39 | 0.085 | 97.45 | 0.095 | 34.06 | 76.84 |
| Group 11 | 0.1% PVA3 | 63.83 | 0.091 | 85.07 | 0.093 | 21.24 | 74.25 |
| Group 12 | 0.05% PVA3 | 63.34 | 0.077 | 85.96 | 0.065 | 22.62 | 67.64 |
| Group 13 | 1.0% HA + 0.05% PVA1 | 62.64 | 0.093 | 68.91 | 0.158 | 6.27 | 43.12 |
| Group 14 | 1.0% HA + 0.05% PVA2 | 62.12 | 0.104 | 90.17 | 0.294 | 28.05 | 43.55 |
| Group 15 | 1.0% HA + 0.05% PVA3 | 61.97 | 0.111 | 67.01 | 0.107 | 5.04 | 43.55 |

In general, none of the formulations showed acceptable values for both δ and for the percent encapsulation, however Groups 13 and 15 dis show superior values for δ. It was decided to perform further studies with a different lyophilization cycle and to also assess the effect of adding sucrose.

Example 5: Further Studies Regarding PVA Excipients Using a Different Lyophilization Cycle The experiments of Example 4 were extended to study the effect lyophilization cycle and further the effect of adding sucrose. In this study, the lyophilization cycle of Examples 2 and 4 were changed to have vials loaded with suspension and frozen at −48° C., a primary drying temperature of −35° C., a secondary drying step of 10° C., and the volume of suspension lyophilized was reduced to 1.5 mL. The conditions and results of this study are provided in Table 6 below.

TABLE 6

Conditions and Results of Studies on Lyophilization Cycle and Addition of Sucrose

|  |  | Excipients | Size (nm) | PDI | δ | % Encap | Comments |
|---|---|---|---|---|---|---|---|
|  | Group 1 | 2.5% HA | 78.84 | 0.284 | 15.51 | 69.4 |  |
|  | Group 2 | 1.0% HA | 74.67 | 0.195 | 11.34 | 71.4 |  |
|  | Group 3 | 0.5% HA | 76.64 | 0.186 | 13.31 | 66.6 |  |
|  | Group 4 | 1.0% HA | 78.53 | 0.12 | 15.2 | 80 |  |
|  | Group 5 | 0.5% PVA1 |  |  |  |  | Slow Dissolution |
|  | Group 6 | 0.1% PVA1 |  |  |  |  | Slow Dissolution |
|  | Group 7 | 0.05% PVA1 | 83.69 | 0.089 | 20.36 | 81.9 |  |
|  | Group 8 | 0.5% PVA2 | 125.8 | 0.182 | 62.47 | 62.5 |  |
|  | Group 9 | 0.1% PVA2 | 99.08 | 0.249 | 35.75 | 64.7 |  |
|  | Group 10 | 0.05% PVA2 | 108.2 | 0.299 | 44.87 | 70.6 |  |
|  | Group 11 | 0.5% PVA3 |  |  |  |  | Slow Dissolution |
|  | Group 12 | 0.1% PVA3 | 85.57 | 0.064 | 22.24 | 85.1 |  |
|  | Group 13 | 0.05% PVA3 | 82.71 | 0.077 | 19.38 | 83.9 |  |
|  | Group 14 | 1.0% HA + 0.05% PVA1 | 71.57 | 0.136 | 8.24 | 71.3 |  |
|  | Group 15 | 1.0% HA + 0.05% PVA2 | 83.43 | 0.255 | 20.1 | 63.6 |  |
|  | Group 16 | 1.0% HA + 0.05% PVA3 | 71.0 | 0.117 | 7.67 | 67.5 |  |
| 18% Sucrose | Group 17 | 1.0% HA | 72.22 | 0.168 | 8.89 | 64.6 |  |
|  | Group 18 | 0.1% PVA1 |  |  |  |  | Slow Dissolution |
|  | Group 19 | 0.1% PVA2 | 94.48 | 0.362 | 31.15 | 63.6 |  |
|  | Group 20 | 0.1% PVA3 | 76.01 | 0.12 | 12.68 | 77.9 |  |
|  | Group 21 | 1.0% HA + 0.05% PVA1 | 69.65 | 0.143 | 6.32 | 65.6 |  |

TABLE 6-continued

Conditions and Results of Studies on Lyophilization Cycle and Addition of Sucrose

| | Excipients | Size (nm) | PDI | δ | % Encap | Comments |
|---|---|---|---|---|---|---|
| Group 22 | 1.0% HA + 0.05% PVA2 | 89.67 | 0.369 | 26.34 | 65.6 | |
| Group 23 | 1.0% HA+ 0.05% PVA3 | 69.8 | 0.1 | 6.47 | 64.1 | |

In this further study, the lower drying temperature resulted in higher quality in the lipid nanoparticle formulations, which is most readily observed in comparing the formulations having 1.00 HA (Group 4). It can also be seen that high sucrose improves particle size but decreases the percent encapsulation.

Example 6: Evaluation of Various PVA Excipients

Further studies were designed and conducted to compare the effect of different PVA excipients at various concentrations. The PVA excipients used in this study were PVA0, PVA2, PVA3, PVA4, PVA 5, PVA6, and PVA7. The conditions of the lyophilization experiments and the results are provided in Table 7 below. The lyophilization cycle of Example 5 were used in this experiment.

The lowest δ values in combination with acceptable values for percent encapsulation and PDI were observed with PVA3 formulations. The results of Group 14 also suggest that PVA3 in combination with human albumin (HA) has a better effect than using only PVA3 (Groups 9-12).

Example 7: Additional Round of Evaluation of PVA Excipients

Further studies were conducted to take the learnings of Example 6 and compare them with other PVA excipients, in particular, PVA8, PVA9, and PVA10. The lipid nanoparticle formulations were prepared as described in previous examples, and the lyophilization cycle of Example 5 was applied in these experiments, with the exception that a primary drying temperature of −25° C. was applied. The specific conditions and results are shown in Table 8.

TABLE 7

| Group No. | Conditions | Freeze-Thaw Samples | | | Post Lyophilization Reconstituted Samples | | | |
|---|---|---|---|---|---|---|---|---|
| | | Size | PDI | % Encap | Size | PDI | % Encap | δ |
| Group 1 | 1% HA | 63.83 | 0.159 | 74.8 | 75.61 | 0.216 | 75.1 | 13.98 |
| Group 2 | 1% HA double conc. of API | 65.55 | 0.095 | 76.5 | 79.02 | 0.19 | 72.7 | 17.39 |
| Group 3 | 0.5% PVA1 | 76.18 | 0.1 | 95.4 | 107 | 0.091 | | 45.37 |
| Group 4 | 0.1% PVA1 | 71.33 | 0.061 | 95.5 | 93.89 | 0.105 | 82.0 | 32.26 |
| Group 5 | 0.05% PVA1 | 71.09 | 0.035 | 95.9 | 86.78 | 0.13 | 83.8 | 25.15 |
| Group 6 | 0.1% PVA1 double conc. | 71.97 | 0.077 | 94.5 | 103.4 | 0.102 | 86.8 | 41.77 |
| Group 7 | 0.1% PVA2 | 63.98 | 0.111 | 91.1 | 102.5 | 0.304 | 69.8 | 40.87 |
| Group 8 | 0.05% PVA2 | 68.47 | 0.142 | 93.5 | 107.9 | 0.413 | 81.4 | 46.27 |
| Group 9 | 0.5% PVA3 | 72.54 | 0.082 | 96.4 | 102.7 | 0.099 | 86.2 | 41.07 |
| Group 10 | 0.2% PVA3 | 71.46 | 0.058 | 96.1 | 90.87 | 0.112 | 85.1 | 29.24 |
| Group 11 | 0.1% PVA3 | 70.69 | 0.053 | 95.9 | 83.62 | 0.095 | 84.7 | 21.99 |
| Group 12 | 0.1% PVA3 double conc. | 72.43 | 0.041 | 96.3 | 98.32 | 0.106 | 84.0 | 36.69 |
| Group 13 | 0.1% PVA3 + 1% HA | 64.4 | 0.124 | | 72.54 | 0.134 | | 10.91 |
| Group 14 | 0.05% PVA3 + 0.5% HA | 64.55 | 0.113 | 83.4 | 74.39 | 0.11 | 74.9 | 12.76 |
| Group 15 | 0.05% PVA3 | 68.53 | 0.087 | 95.9 | 85.35 | 0.107 | 81.6 | 23.72 |
| Group 16 | 0.1% PVA4 | 68.06 | 0.093 | 96.2 | 97.87 | 0.08 | 81.4 | 36.24 |
| Group 17 | 0.05% PVA4 | 70.76 | 0.096 | 95.7 | 94.5 | 0.108 | 77.9 | 32.87 |
| Group 18 | 0.05% PVA + 0.5% HA | 64.85 | 0.099 | 80.9 | 75.84 | 0.146 | 78.9 | 14.21 |
| Group 19 | 0.1% PVA5 | 71.7 | 0.072 | 95.2 | 91.72 | 0.089 | 82.3 | 30.09 |
| Group 20 | 0.05% PVA5 | 71.71 | 0.036 | 95.9 | 90.73 | 0.076 | 81.8 | 29.1 |
| Group 21 | 1% HA + 0.05% PVA | 66.75 | 0.1 | 77.3 | 78.7 | 0.129 | 74.2 | 17.07 |
| Group 22 | 0.1% PVA6 | 72.13 | 0.063 | 95.6 | 93.36 | 0.102 | 82.7 | 31.73 |
| Group 23 | 0.05% PVA6 | 73.16 | 0.07 | 95.6 | 91.53 | 0.078 | 77.6 | 29.9 |
| Group 24 | 1% HA + 0.05% PVA6 | 66.61 | 0.077 | 78.8 | 77.49 | 0.111 | 70.8 | 15.86 |
| Group 25 | 0.1% PVA7 | 69.68 | 0.109 | 95.2 | 97.39 | 0.104 | 77.6 | 35.76 |
| Group 26 | 0.05% PVA7 | 72.21 | 0.075 | 96.7 | 97.05 | 0.098 | 79.4 | 35.42 |
| Group 27 | 1% HA + 0.05% PVA7 | 64.48 | 0.109 | 76.4 | 77.37 | 0.147 | 80.3 | 15.74 |

TABLE 8

| Group No. | Conditions | Size | PDI | % Encap | Size | PDI | % Encap | δ |
|---|---|---|---|---|---|---|---|---|
| Group 1 | 1% HA | 79.89 | 0.056 | 97.6 | 86.35 | 0.082 | 80.8 | 6.74 |
| Group 2 | 1% HA double conc. of API | 80.96 | 0.043 | 98.8 | 92.28 | 0.084 | 83.8 | 12.67 |
| Group 3 | 0.5% PVA1 | 83 | 0.048 | 97.1 | 122.1 | 0.169 | 67 | 42.49 |
| Group 4 | 0.1% PVA1 | 80.74 | 0.065 | 97.3 | 91.99 | 0.064 | 81.9 | 12.38 |
| Group 5 | 0.05% PVA1 | 149.9 | 0.252 | 96.9 | 89.3 | 0.058 | 81.2 | 9.69 |
| Group 6 | 0.1% PVA1 double conc. | 81.74 | 0.028 | 94.4 | 103.9 | 0.101 | 85.0 | 24.29 |
| Group 7 | 0.5% PVA3 | 81.95 | 0.052 | 97.1 | 128.3 | 0.147 | 75.5 | 48.69 |
| Group 8 | 0.3% PVA3 | 80.07 | 0.048 | 96.5 | 94.86 | 0.074 | 85.2 | 15.25 |
| Group 9 | 0.2% PVA3 | 79.9 | 0.062 | 96.0 | 92.07 | 0.059 | 81.8 | 12.46 |
| Group 10 | 0.1% PVA3 | 79.5 | 0.063 | 96.2 | 90.5 | 0.063 | 81.5 | 10.89 |
| Group 11 | 0.1% PVA3 + 0.05M NaCl | 80.18 | 0.055 | 97.1 | 88.05 | 0.067 | 84.3 | 8.44 |
| Group 12 | 0.1% PVA3 + 0.1M NaCl | 81.06 | 0.023 | 96.5 | 86.64 | 0.044 | 90.1 | 7.03 |
| Group 13 | 0.1% PVA3 + 0.2M NaCl | 80.92 | 0.027 | 96.8 | 85.41 | 0.063 | 92.9 | 5.8 |
| Group 14 | 0.1% PVA3 double conc. | 80.67 | 0.043 | 96.5 | 99.57 | 0.106 | 84.9 | 19.96 |
| Group 15 | 0.2% PVA3 + 1% HA | 80.31 | 0.025 | 97.8 | 90.19 | 0.086 | 95.5 | 10.58 |
| Group 16 | 0.2% PVA3 + 1% HA + 0.1M NaCl | 80.82 | 0.075 | 97.7 | 83.61 | 0.029 | 91.2 | 4 |
| Group 17 | 0.1% PVA3 + 1% HA + 0.1M NaCl | 80.96 | 0.023 | 97.6 | 81.02 | 0.063 | 95.9 | 1.41 |
| Group 18 | 0.1% PVA3 + 1% HA | 80.3 | 0.053 | 98.0 | 82.04 | 0.056 | 94.8 | 2.43 |
| Group 19 | 0.1% PVA3 + 0.5% HA | 80.03 | 0.009 | 98.2 | 83.86 | 0.08 | 94.0 | 4.25 |
| Group 20 | 0.05% PVA3 + 0.1M NaCl | 76.7 | 0.052 | 96.0 | 83.71 | 0.063 | 89.6 | 4.1 |
| Group 21 | 0.05% PVA3 | 80.82 | 0.028 | 96.2 | 87.34 | 0.047 | 84.7 | 7.73 |
| Group 22 | 0.05% PVA3 + 9% Sucrose | 81.77 | 0.057 | 96.7 | 85.82 | 0.037 | 76.7 | 6.21 |
| Group 23 | 0.5% PVA8 | 82.15 | 0.037 | 93.4 | 92.58 | 0.099 | 56.6 | 12.97 |
| Group 24 | 0.5% PVA8 double conc. | 82.14 | 0.024 | 95.6 | 104.8 | 0.117 | 76.3 | 25.19 |
| Group 25 | 0.2% PVA8 | 81.65 | 0.064 | 94.4 | 89.16 | 0.083 | 71.4 | 9.55 |
| Group 26 | 0.1% PVA8 | 82.34 | 0.056 | 94.7 | 89.47 | 0.097 | 74.8 | 9.86 |
| Group 27 | 0.1% PVA8 double conc. | 81.5 | 0.073 | 94.8 | 97.98 | 0.119 | 81.3 | 18.37 |
| Group 28 | 0.1% PVA8 + 0.1M NaCl | 81.63 | 0.062 | 93.2 | 93.86 | 0.113 | 72.5 | 14.25 |
| Group 29 | 0.1% PVA8 + 1% HA | 80.14 | 0.053 | 97.8 | 85.87 | 0.195 | 65.5 | 6.26 |
| Group 30 | 0.05% PVA8 | 81.72 | 0.039 | 94.1 | 89.88 | 0.078 | 68.8 | 10.27 |
| Group 31 | 0.05% PVA8 + 1% HA | 80.85 | 0.06 | 97.9 | 84.87 | 0.128 | 80.6 | 5.26 |
| Group 32 | 0.05% PVA8 + 9% Sucrose | 82.29 | 0.007 | 94.5 | 87.82 | 0.057 | 54.9 | 8.21 |
| Group 33 | 0.5% PVA9 | 80.3 | 0.028 | 97.2 | 90.22 | 0.053 | 72.6 | 10.61 |
| Group 34 | 0.5% PVA9 double conc. | 82.34 | 0.048 | 97.4 | 108 | 0.076 | 77.2 | 28.39 |
| Group 35 | 0.2% PVA9 | 80.37 | 0.055 | 97.5 | 87.72 | 0.049 | 80.3 | 8.11 |
| Group 36 | 0.1% PVA9 | 80.42 | 0.074 | 97.8 | 86.88 | 0.088 | 81.7 | 7.27 |
| Group 37 | 0.1% PVA9 double conc. | 79.7 | 0.013 | 97.9 | 96.56 | 0.085 | 84.6 | 16.95 |
| Group 38 | 0.1% PVA9 + 0.1M NaCl | 80.16 | 0.017 | 97.4 | 87.7 | 0.103 | 78.7 | 8.09 |
| Group 39 | 0.1% PVA9 + 1% HA | 79.07 | 0.062 | 96.0 | 83.2 | 0.064 | 89.2 | 3.59 |
| Group 40 | 0.05% PVA9 | 82.11 | 0.026 | 98.4 | 86.28 | 0.041 | 78.3 | 6.67 |
| Group 41 | 0.05% PVA9 + 1% HA | 80.69 | 0.037 | 98.7 | 81.88 | 0.059 | 90.5 | 2.27 |
| Group 42 | 0.05% PVA9 + 9% Sucrose | 83.39 | 0.037 | 98.0 | 86.91 | 0.047 | 68.6 | 7.3 |
| Group 43 | 0.5% PVA10 | 80.9 | 0.032 | 98.3 | 103.7 | 0.085 | 87.8 | 24.09 |
| Group 44 | 0.5% PVA10 double conc. | 81.66 | 0.065 | 98.3 | 143.9 | 0.202 | 76.1 | 64.29 |
| Group 45 | 0.2% PVA10 | 81.48 | 0.027 | 98.3 | 90.01 | 0.065 | 87.9 | 10.4 |
| Group 46 | 0.1% PVA10 | 80.96 | 0.03 | 97.9 | 86.49 | 0.05 | 81.9 | 6.88 |
| Group 47 | 0.1% PVA10 double conc. | 81.06 | 0.024 | 98.2 | 96.53 | 0.077 | 86.7 | 16.92 |
| Group 48 | 0.1% PVA10 + 0.1M NaCl | 79.48 | 0.019 | 98.1 | 84.19 | 0.042 | 92.8 | 4.58 |
| Group 49 | 0.1% PVA10 + 1% HA | 80.95 | 0.086 | 98.7 | 80.79 | 0.041 | 93.5 | 1.18 |
| Group 50 | 0.05% PVA | 80.78 | 0.074 | 98.0 | 85.63 | 0.043 | 84.1 | 6.02 |
| Group 51 | 0.05% PVA10 + 1% HA | 79.59 | 0.062 | 98.7 | 79.69 | 0.047 | 94.5 | 0.08 |
| Group 52 | 0.05% PVA10 + 9% Sucrose | 82.08 | 0.03 | 97.8 | 86 | 0.074 | 78.7 | 6.39 |

The results suggest that PVA10 shows great results with Groups 48, 49, and 51, showing good encapsulation and delta values. The PVA3 Groups 12-13 and 16-19 also showed great values.

Example 8: Direct Comparative Studies of PVA3 and PVA10

With the learnings of the studies of Example 7, further experiments were designed to directly compare formulations using PVA3 or PVA10. In this experiment, the lipid nanoparticle formulations were prepared as described in Example 1, and the lyophilization cycle of Example 5 was applied. The conditions and results for these experiments are provided in Table 9.

TABLE 9

Comparison of PVA3 and PVA10 Formulations

| # | Notes | Size (nm) Pre | PDI Pre | % Encap Pre | Size (nm) Post | PDI Post | % Encap Post | δ |
|---|---|---|---|---|---|---|---|---|
| Group 1 | 1% HA | 63.45 | 0.103 | 73.9 | 67.18 | 0.209 | 74.6 | 7.12 |
| Group 2 | 1% HA double conc. of API | 66.17 | 0.12 | 75.0 | 72.17 | 0.18 | 76.2 | 12.11 |
| Group 3 | 1% HA + 0.05M NaCl | 63.06 | 0.146 | 70.0 | 68.83 | 0.226 | 75.0 | 8.77 |
| Group 4 | 1% HA + 0.1M NaCl | 63.38 | 0.133 | 69.9 | 70.9 | 0.245 | 74.3 | 10.84 |
| Group 5 | 1% HA + 0.2M NaCl | 66.26 | 0.142 | 71.1 | 77.79 | 0.215 | 76.6 | 17.73 |
| Group 6 | 1% HA + 0.2M NaCl double conc. | 69.28 | 0.162 | 70.1 | 75.51 | 0.22 | 77.0 | 15.45 |
| Group 7 | 0.5% HA | 63.79 | 0.086 | 74.1 | 319.1 | 0.811 | 74.1 | 259.04 |
| Group 8 | 0.5% HA + 0.1M NaCl | 65.62 | 0.133 | 70.3 | 72.34 | 0.202 | 74.0 | 12.28 |
| Group 9 | 0.5% HA + 0.2M NaCl | 69.88 | 0.156 | 73.8 | 81.07 | 0.174 | 75.8 | 21.01 |
| Group 10 | 0.5% HA + 0.1 double conc. | 69.24 | 0.148 | 71.9 | 74.82 | 0.176 | 74.8 | 14.76 |
| Group 11 | 0.2% PVA3 | 68.66 | 0.083 | 89.8 | 82.2 | 0.1 | 91.7 | 22.14 |
| Group 12 | 0.2% PVA3 + 0.3M NaCl | 70.69 | 0.079 | 89.3 | 168.4 | 0.349 | 84.8 | 108.34 |
| Group 13 | 0.2% PVA3 + 0.2M NaCl | 70.03 | 0.067 | 95.6 | 83.28 | 0.109 | 86.3 | 23.22 |
| Group 14 | 0.2% PVA3 + 0.1M NaCl | 69.83 | 0.066 | 95.3 | 81.42 | 0.082 | 88.3 | 21.36 |
| Group 15 | 0.2% PVA3 + 0.05M NaCl | 63.4 | 0.083 | 96.4 | 80.17 | 0.084 | 94.0 | 20.11 |
| Group 16 | 0.2% PVA3 + 1% HA | 60.41 | 0.112 | 75.6 | 68.54 | 0.121 | 74.9 | 8.48 |
| Group 17 | 0.2% PVA3 + 1% HA + 0.2M NaCl | 59.81 | 0.108 | 72.0 | 62.97 | 0.091 | 71.2 | 2.91 |
| Group 18 | 0.2% PVA3 + 1% HA + 0.1M NaCl | 61.26 | 0.119 | 71.0 | 65.96 | 0.158 | 70.0 | 5.9 |
| Group 19 | 0.2% PVA3 + 1% HA + 0.05M NaCl | 60.58 | 0.102 | 72.4 | 65.74 | 0.119 | 71.2 | 5.68 |
| Group 20 | 0.1% PVA | 69.26 | 0.044 | 96.3 | 79.88 | 0.108 | 91.2 | 19.82 |
| Group 21 | 0.1% PVA3 + 0.3M NaCl | 70.78 | 0.059 | 96.7 | 85.43 | 0.116 | 95.6 | 25.37 |
| Group 22 | 0.1% PVA3 + 0.2M NaCl | 70.9 | 0.043 | 96.7 | 78.47 | 0.033 | 95.9 | 18.41 |
| Group 23 | 0.1% PVA3 + 0.1M NaCl | 69.91 | 0.085 | 96.4 | 78.56 | 0.08 | 94.7 | 18.5 |
| Group 24 | 0.1% PVA3 + 0.05M NaCl | 70.62 | 0.034 | 95.8 | 77.08 | 0.082 | 93.6 | 17.02 |
| Group 25 | 0.1% PVA3 + 1% HA | 62.83 | 0.117 | 74.7 | 68.44 | 0.141 | 73.2 | 8.38 |
| Group 26 | 0.1% PVA3 + 1% HA + 0.2M NaCl | 60.3 | 0.124 | 71.5 | | | 74.2 | −60.06 |
| Group 27 | 0.1% PVA3 + 1% HA + 0.1M NaCl | 60.95 | 0.106 | 70.7 | 62.81 | 0.123 | 72.3 | 2.75 |
| Group 28 | 0.1% PVA3 + 1% HA + 0.05M NaCl | 61.02 | 0.126 | 71.8 | 65.19 | 0.129 | 72.6 | 5.13 |
| Group 29 | 0.05% PVA | 70.22 | 0.091 | 93.9 | 77 | 0.097 | 91.2 | 16.94 |
| Group 30 | 0.05% PVA3 + 0.3M NaCl | 72.1 | 0.056 | 92.4 | 83.68 | 0.052 | 95.5 | 23.62 |
| Group 31 | 0.05% PVA3 + 0.2M NaCl | 70.99 | 0.093 | 89.8 | 77.54 | 0.084 | 95.7 | 17.48 |
| Group 32 | 0.05% PVA3 + 0.1M NaCl | 71.17 | 0.069 | 89.8 | 76.22 | 0.082 | 94.3 | 16.16 |
| Group 33 | 0.05% PVA3 + 0.05M NaCl | 63.28 | 0.068 | 89.2 | 76 | 0.125 | 93.6 | 15.94 |
| Group 34 | 0.05% PVA3 + 1% HA | 61.75 | 0.096 | 73.4 | 68.57 | 0.143 | 73.7 | 8.51 |
| Group 35 | 0.05% PVA3 + 1% HA + 0.2M NaCl | 60.47 | 0.112 | 70.3 | 62.95 | 0.139 | 74.3 | 2.89 |
| Group 36 | 0.05% PVA3 + 1% HA + 0.1M NaCl | 61.57 | 0.122 | 70.0 | 63.78 | 0.154 | 74.3 | 3.72 |
| Group 37 | 0.05% PVA3 + 1% HA + 0.05M NaCl | 63.62 | 0.096 | 69.0 | 66.17 | 0.141 | 71.4 | 6.11 |
| Group 38 | 0.05% PVA3 + 0.5% HA | 63.07 | 0.111 | 73.6 | 69.83 | 0.142 | 73.0 | 9.77 |
| Group 39 | 0.05% PVA3 + 0.5% HA + 0.2M NaCl | 61.36 | 0.111 | 71.2 | 66.71 | 0.12 | 76.7 | 6.65 |
| Group 40 | 0.05% PVA3 + 0.5% HA + 0.1M NaCl | 1.165 | 0.224 | 70.3 | 66.37 | 0.176 | 73.9 | 6.31 |
| Group 41 | 0.2% PVA | 69.16 | 0.058 | 95.3 | 82.3 | 0.123 | 90.0 | 22.24 |
| Group 42 | 0.2% PVA + 0.3M NaCl | 72.17 | 0.073 | 95.6 | 110.2 | 0.134 | 90.6 | 50.14 |
| Group 43 | 0.2% PVA + 0.2M NaCl | 72.05 | 0.047 | 95.6 | 83.5 | 0.076 | 94.4 | 23.44 |
| Group 44 | 0.2% PVA + 0.1M NaCl | 71.07 | 0.067 | 95.7 | 81.46 | 0.078 | 94.3 | 21.4 |
| Group 45 | 0.2% PVA + 0.05M NaCl | 70.9 | 0.055 | 94.3 | 80.45 | 0.091 | 92.9 | 20.39 |
| Group 46 | 0.2% PVA + 1% HA | 64.13 | 0.109 | 72.1 | 68.11 | 0.128 | 73.6 | 8.05 |
| Group 47 | 0.2% PVA + 1% HA + 0.2M NaCl | 61.03 | 0.105 | 71.1 | 63.68 | 0.108 | 77.3 | 3.62 |
| Group 48 | 0.2% PVA + 1% HA + 0.1M NaCl | 60.92 | 0.122 | 69.4 | 64 | 0.115 | 73.8 | 3.94 |
| Group 49 | 0.2% PVA + 1% HA + 0.05M NaCl | 61.59 | 0.115 | 67.4 | 65.08 | 0.145 | 74.1 | 5.02 |
| Group 50 | 0.1% PVA | 71.53 | 0.046 | 94.5 | 78.39 | 0.131 | 91.7 | 18.33 |
| Group 51 | 0.1% PVA + 0.3M NaCl | 70.25 | 0.074 | 95.6 | 85.01 | 0.059 | 95.6 | 24.95 |
| Group 52 | 0.1% PVA + 0.2M NaCl | 69.01 | 0.082 | 95.8 | 78.6 | 0.063 | 95.7 | 18.54 |

TABLE 9-continued

Comparison of PVA3 and PVA10 Formulations

| # | Notes | Size (nm) Pre | PDI Pre | % Encap Pre | Size (nm) Post | PDI Post | % Encap Post | δ |
|---|---|---|---|---|---|---|---|---|
| Group 53 | 0.1% PVA + 0.1M NaCl | 67.71 | 0.073 | 95.6 | 76.41 | 0.089 | 95.1 | 16.35 |
| Group 54 | 0.1% PVA + 0.05M NaCl | 68.22 | 0.048 | 95.3 | 78.25 | 0.105 | 93.0 | 18.19 |
| Group 55 | 0.1% PVA + 1% HA | 61.15 | 0.085 | 71.5 | 68.51 | 0.146 | 73.9 | 8.45 |
| Group 56 | 0.1% PVA + 1% HA + 0.2M NaCl | 58.97 | 0.101 | 69.4 | 62.12 | 0.153 | 77.4 | 2.06 |
| Group 57 | 0.1% PVA + 1% HA + 0.1M NaCl | 58.38 | 0.121 | 68.8 | 63.89 | 0.123 | 75.3 | 3.83 |
| Group 58 | 0.1% PVA + 1% HA + 0.05M NaCl | 59.13 | 0.118 | 68.4 | 65.16 | 0.133 | 75.3 | 5.1 |
| Group 59 | 0.05% PVA | 67.11 | 0.046 | 90.2 | 76.37 | 0.118 | 92.0 | 16.31 |
| Group 60 | 0.05% PVA + 0.3M NaCl | 70.75 | 0.042 | 90.9 | 84.12 | 0.099 | 95.3 | 24.06 |
| Group 61 | 0.05% PVA + 0.2M NaCl | 69.93 | 0.05 | 97.0 | 81.09 | 0.076 | 95.4 | 21.03 |
| Group 62 | 0.05% PVA + 0.1M NaCl | 69.66 | 0.03 | 96.9 | 76.68 | 0.091 | 94.3 | 16.62 |
| Group 63 | 0.05% PVA + 0.05M NaCl | 69.33 | 0.061 | 96.8 | 76.45 | 0.133 | 93.6 | 16.39 |
| Group 64 | 0.05% PVA + 1% HA | 61.78 | 0.104 | 72.6 | 67.66 | 0.137 | 72.2 | 7.6 |
| Group 65 | 0.05% PVA + 1% HA + 0.2M NaCl | 59.94 | 0.111 | 71.3 | 63.65 | 0.093 | 77.9 | 3.59 |
| Group 66 | 0.05% PVA + 1% HA + 0.1M NaCl | 59.4 | 0.136 | 70.1 | 63.8 | 0.147 | 76.4 | 3.74 |
| Group 67 | 0.05% PVA + 1% HA + 0.05M NaCl | 59.72 | 0.121 | 69.3 | 65.91 | 0.135 | 74.2 | 5.85 |
| Group 68 | 0.05% PVA + 0.5% HA | 63.06 | 0.068 | 76.8 | 70.14 | 0.118 | 72.5 | 10.08 |
| Group 69 | 0.05% PVA + 0.5% HA + 0.2M NaCl | 61.43 | 0.106 | 74.1 | 67.36 | 0.137 | 81.2 | 7.3 |
| Group 70 | 0.05% PVA + 0.5% HA + 0.1M NaCl | 60.77 | 0.101 | 73.7 | 67.77 | 0.151 | 77.8 | 7.71 |

The delta values from these studies were large for several groups, and groups that showed delta values less than 5 had low encapsulation efficiency. Conversely, other groups showed good encapsulation efficiency values above 9000, but higher delta values. PVA3 and PVA10 are comparable at the conditions tested, and the optimal conditions from this experiment appear to be those of Group 33 and Group 63.

Example 9: Studies Using Potassium Sorbate

Experiments were next designed to assess the effect of Potassium Sorbate (KS) on lyophilized lipid nanoparticles that could include PVA. The lipid nanoparticle formulations were prepared as described in Example 1 and the lyophilization cycle of Example 5 was applied. The specific conditions and results are shown in Table 10.

TABLE 10

Conditions and Results of Potassium Sorbate Formulations

| Group No. | Conditions | Size (nm) Pre | PDI Pre | % Encap Pre | Size (nm) Post | PDI Post | % Encap Post | δ |
|---|---|---|---|---|---|---|---|---|
| Group 1 | 0.1% PVA + 0.1% HA + 0.3M NaCl | 67.67 | 0.1 | 94.3 | 73.26 | 0.086 | 78.2 | 13.12 |
| Group 2 | 0.05% PVA + 0.2% HA + 0.3M NaCl | 67.21 | 0.123 | 92.9 | 71.82 | 0.131 | 94.4 | 11.68 |
| Group 3 | 0.05% PVA + 0.05% HA | 65.36 | 0.102 | 94.1 | 72.4 | 0.163 | 93.3 | 12.26 |
| Group 4 | 0.05% PVA + 0.05% HA + 0.3M NaCl | 68.37 | 0.121 | 95.9 | 75.75 | 0.153 | 87.6 | 15.61 |
| Group 5 | 0.03% PVA + 0.1M NaCl | 68.47 | 0.104 | 97.6 | 73.71 | 0.169 | 94.8 | 13.57 |
| Group 6 | 0.02% PVA + 0.1M NaCl | 67.74 | 0.105 | 97.7 | 75.49 | 0.174 | 95.5 | 15.35 |
| Group 7 | 0.01% PVA + 0.1M NaCl | 68.71 | 0.098 | 97.6 | 74.89 | 0.167 | 95.2 | 14.75 |
| Group 8 | 0.05% PVA + 0.05M NaCl | 70.58 | 0.239 | 97.6 | 74.51 | 0.142 | 95.7 | 14.37 |
| Group 9 | 0.1% PVA + 1% HA + 0.2M NaCl + 0.2M KS | 62.78 | 0.136 | 94.9 | 89.06 | 0.193 | 95.5 | 28.92 |
| Group 10 | 0.1% PVA + 0.5% HA + 0.2M NaCl + 0.2M KS | 61.86 | 0.149 | 95.5 | 97.08 | 0.145 | 70.3 | 36.94 |
| Group 11 | 0.05% PVA + 0.1M NaCl + 0.2M KS | 60.72 | 0.14 | 97.5 | 62.2 | 0.141 | 76.2 | 2.06 |
| Group 12 | 0.05% PVA + 0.05M NaCl + 0.2M KS | 60.31 | 0.149 | 97.0 | 61.77 | 0.16 | 96.9 | 1.63 |
| Group 13 | 0.05% PVA + 0.05M NaCl + 0.1M KS | 59.8 | 0.147 | 97.2 | 61.66 | 0.127 | 95.2 | 1.52 |
| Group 14 | 1% HA + 0.1M KS | 61.4 | 0.146 | 93.9 | 69.19 | 0.196 | 94.1 | 9.05 |
| Group 15 | 0.5% HA + 0.2M KS | 61.26 | 0.116 | 95.8 | 67.85 | 0.153 | 95.2 | 7.71 |
| Group 16 | 0.5% HA + 0.1M KS | 62.44 | 0.158 | 94.8 | 68.65 | 0.171 | 95.6 | 8.51 |

TABLE 10-continued

Conditions and Results of Potassium Sorbate Formulations

| Group No. | Conditions | Size (nm) Pre | PDI Pre | % Encap Pre | Size (nm) Post | PDI Post | % Encap Post | δ |
|---|---|---|---|---|---|---|---|---|
| Group 17 | 0.1% PVA + 1% HA + 0.2M KS | 63.11 | 0.137 | 94.8 | 70.82 | 0.181 | 95.7 | 10.68 |
| Group 18 | 0.1% PVA + 0.5% HA + 0.2M KS | 62.99 | 0.164 | 95.8 | 67.63 | 0.144 | 95.4 | 7.49 |
| Group 19 | 0.05% PVA + 0.1M KS | 61.22 | 0.146 | 97.4 | 63.08 | 0.147 | 76.4 | 2.94 |

The Groups in which human albumin and PVA were combined did not show acceptable results. Groups 12 and 13 showed good delta values and good encapsulation efficiency. The conditions of these groups were selected for further studies.

Example 10: Further Studies on Potassium Sorbate and Sodium Benzoate

In this study the conditions of the experiments of Example 9 were further studied for concentrations of RNA at 1.0 mg/mL. Studies including PVA11 and polysorbate20 (PS20) were also performed. The lipid nanoparticle formulations were prepared as described in Example 1 and the lyophilization of Example 5 was applied. The conditions and results are provided in Table 11 below (Note: F/T indicates freeze-thaw formulations, which were frozen at −70° C. and then thawed before characterization).

TABLE 11

Further Studies on Potassium Sorbate

| # | Notes | Size (nm) F/T | PDI F/T | % Encap F/T | Size (nm) Post | PDI Post | % Encap Post | δ |
|---|---|---|---|---|---|---|---|---|
| Group 1 | 1% HA + 0.1M KS + 0.05M NaCl | 65.81 | 0.12 | 82.90 | 80.16 | 0.14 | 86.01 | 21.52 |
| Group 2 | 0.5% HA + 0.2M KS | 77.99 | 0.11 | 91.19 | 79.73 | 0.10 | 92.15 | 21.09 |
| Group 3 | 0.5% HA + 0.1M KS | 65.66 | 0.12 | 88.49 | 73.36 | 0.12 | 91.47 | 14.72 |
| Group 4 | 1% HA + 0.05M KS | 65.24 | 0.11 | 85.63 | 75.52 | 0.17 | 88.58 | 16.88 |
| Group 5 | 0.5% HA + 0.05M KS | 64.37 | 0.08 | 87.14 | 72.55 | 0.15 | 89.05 | 13.91 |
| Group 6 | 0.5% HA + 0.2M KS (0.5 mg/ml) | 77.20 | 0.12 | 92.36 | 82.35 | 0.09 | 92.18 | 23.71 |
| Group 7 | 0.5% HA + 0.2M KS (1.0 mg/ml) | 85.28 | 0.11 | 94.25 | 83.82 | 0.15 | 93.99 | 25.18 |
| Group 8 | 1% HA + 0.1M NaB + 0.05M NaCl | 65.80 | 0.13 | 82.45 | 72.89 | 0.12 | 89.59 | 14.25 |
| Group 9 | 0.5% HA + 0.2M NaB | 81.50 | 0.13 | 90.12 | 84.57 | 0.13 | 91.80 | 25.93 |
| Group 10 | 0.5% HA + 0.1M NaB | 67.58 | 0.12 | 82.86 | 79.07 | 0.15 | 90.53 | 20.43 |
| Group 11 | 1% HA + 0.05M NaB | 62.69 | 0.07 | 79.61 | 76.57 | 0.20 | 88.59 | 17.93 |
| Group 12 | 0.5% HA + 0.05M NaB | 63.49 | 0.10 | 79.39 | 81.41 | 0.17 | 88.88 | 22.77 |
| Group 13 | 0.5% HA + 0.2M NaB (0.5 mg/ml) | 90.22 | 0.10 | 90.47 | 93.95 | 0.14 | 91.93 | 35.31 |
| Group 14 | 1% HA + 0.1M NaA + 0.05M NaCl | 86.25 | 0.23 | 64.20 | 114.40 | 0.43 | 77.15 | 55.76 |
| Group 15 | 0.5% HA + 0.2M NaA | 118.20 | 0.18 | 66.21 | 130.40 | 0.41 | 69.36 | 71.76 |
| Group 16 | 0.5% HA + 0.1M NaA | 90.72 | 0.18 | 67.05 | 121.20 | 0.40 | 65.81 | 62.56 |
| Group 17 | 1% HA + 0.05M NaA | 74.19 | 0.17 | 64.58 | 85.60 | 0.40 | 64.32 | 26.96 |
| Group 18 | 0.5% HA + 0.05M NaA | 77.49 | 0.14 | 65.45 | 83.55 | 0.30 | 65.26 | 24.91 |
| Group 19 | 0.5% HA + 0.2M NaA (0.5 mg/ml) | 120.30 | 0.20 | 68.52 | 127.20 | 0.35 | 68.14 | 68.56 |
| Group 20 | 1% HA + 0.1M NaS + 0.05M NaCl | 80.38 | 0.06 | 91.91 | 138.90 | 0.14 | 91.25 | 80.26 |
| Group 21 | 0.5% HA + 0.2M NaS | 78.61 | 0.07 | 93.89 | 85.00 | 0.10 | 93.11 | 26.36 |
| Group 22 | 0.5% HA + 0.1M NaS | 78.03 | 0.08 | 94.04 | 110.30 | 0.11 | 92.38 | 51.66 |
| Group 23 | 1% HA + 0.05M NaS | 80.53 | 0.06 | 92.75 | 138.50 | 0.12 | 90.05 | 79.86 |
| Group 24 | 0.5% HA + 0.05M NaS | 80.44 | 0.05 | 93.11 | 115.60 | 0.13 | 92.64 | 56.96 |
| Group 25 | 0.5% HA + 0.2M NaS (0.5 mg/ml) | 78.25 | 0.06 | 96.04 | 96.42 | 0.09 | 94.38 | 37.78 |
| Group 26 | 1% HA + 1% M PS20 + 0.05M NaCl | 56.66 | 0.09 | 68.41 | 75.23 | 0.22 | 57.53 | 16.59 |
| Group 27 | 0.5% HA + 0.2% PS20 | 61.05 | 0.10 | 98.19 | 80.46 | 0.16 | 65.65 | 21.82 |
| Group 28 | 0.5% HA + 0.1% PS20 | 60.21 | 0.09 | 98.11 | 75.23 | 0.20 | 74.30 | 16.59 |
| Group 29 | 1% HA + 0.05% PS20 | 65.59 | 0.18 | 97.70 | 78.63 | 0.28 | 84.61 | 19.99 |
| Group 30 | 0.5% HA + 0.05% PS20 | 61.31 | 0.09 | 98.22 | 75.42 | 0.22 | 78.17 | 16.78 |
| Group 31 | 0.5% HA + 0.2% PS20(0.5 mg/ml) | 59.49 | 0.08 | 98.63 | 87.79 | 0.18 | 72.02 | 29.15 |
| Group 32 | 3% PS20 | 54.71 | 0.10 | 57.10 | 55.33 | 0.37 | 64.71 | −3.31 |
| Group 33 | 1% PS20 | 58.34 | 0.09 | 68.08 | 63.10 | 0.14 | 61.31 | 4.46 |
| Group 34 | 0.5% PS20 | 60.61 | 0.05 | 92.22 | 67.35 | 0.12 | 64.92 | 8.71 |
| Group 35 | 0.1% PS20 | 59.79 | 0.07 | 96.53 | 72.36 | 0.15 | 69.89 | 13.72 |
| Group 36 | 0.05% PS20 | 59.58 | 0.08 | 96.56 | 69.96 | 0.14 | 72.48 | 11.32 |
| Group 37 | 0.05% PVA10 + 0.2% HA + 0.3M NaCl | 66.90 | 0.08 | 75.63 | 72.00 | 0.10 | 78.80 | 13.36 |
| Group 38 | 0.05% PVA10 + 0.05% HA | 68.46 | 0.04 | 76.54 | 73.57 | 0.13 | 78.26 | 14.93 |
| Group 39 | 0.05% PVA10 + 0.05M NaCl | 70.74 | 0.05 | 96.37 | 76.74 | 0.12 | 92.41 | 18.10 |
| Group 40 | 0.05% PVA10 + 0.05M NaCl + 0.2M KS | 67.26 | 0.07 | 96.28 | 68.51 | 0.08 | 95.85 | 9.87 |
| Group 41 | 0.05% PVA10 + 0.05M NaCl + 0.1M KS | 62.97 | 0.11 | 96.53 | 62.90 | 0.10 | 95.86 | 4.26 |
| Group 42 | 0.05% PVA10 + 0.05M NaCl + 0.1M KS (0.5 mg/ml) | 59.13 | 0.10 | 96.75 | 62.12 | 0.09 | 96.07 | 3.48 |

TABLE 11-continued

Further Studies on Potassium Sorbate

| # | Notes | Size (nm) F/T | PDI F/T | % Encap F/T | Size (nm) Post | PDI Post | % Encap Post | δ |
|---|---|---|---|---|---|---|---|---|
| Group 43 | 0.05% PVA10 + 0.05M NaCl + 0.1M KS (1.0 mg/ml) | 59.64 | 0.06 | 97.60 | 64.96 | 0.10 | 97.13 | 6.32 |
| Group 44 | 0.05% PVA10 + 0.05M NaCl + 0.1M NaB | 63.41 | 0.07 | 96.93 | 63.33 | 0.13 | 96.75 | 4.69 |
| Group 45 | 0.05% PVA10 + 0.05M NaCl + 0.1M NaA | 87.35 | 0.05 | 96.38 | 99.42 | 0.19 | 88.92 | 40.78 |
| Group 46 | 0.05% PVA10 + 0.05M NaCl + 0.1M NaS | 91.00 | 0.04 | 96.24 | 122.50 | 0.11 | 95.77 | 63.86 |
| Group 47 | 0.05% PVA10 + 0.05M NaCl + 0.1% PS20 | 60.74 | 0.09 | 96.21 | 71.72 | 0.12 | 70.23 | 13.08 |
| Group 48 | 0.05% PVA11 + 0.2% HA + 0.3M NaCl | 67.82 | 0.10 | 75.66 | 75.80 | 0.15 | 81.98 | 17.16 |
| Group 49 | 0.05% PVA11 + 0.05% HA | 65.74 | 0.06 | 71.90 | 76.06 | 0.16 | 74.99 | 17.42 |
| Group 50 | 0.05% PVA11 + 0.05M NaCl | 69.84 | 0.02 | 95.93 | 80.98 | 0.15 | 91.29 | 22.34 |
| Group 51 | 0.05% PVA11 + 0.05M NaCl + 0.2M KS | 64.39 | 0.08 | 96.20 | 69.34 | 0.06 | 96.04 | 10.70 |
| Group 52 | 0.05% PVA11 + 0.05M NaCl + 0.1M KS | 60.48 | 0.09 | 96.39 | 65.26 | 0.11 | 95.93 | 6.62 |
| Group 53 | 0.05% PVA11 + 0.05M NaCl + 0.1M KS (0.5 mg/ml) | 59.83 | 0.07 | 96.87 | 64.65 | 0.11 | 96.24 | 6.01 |
| Group 54 | 0.05% PVA11 + 0.05M NaCl + 0.1M KS (1.0 mg/ml) | 58.58 | 0.10 | 96.89 | 63.06 | 0.08 | 97.20 | 4.42 |
| Group 55 | 0.05% PVA11 + 0.05M NaCl + 0.1M NaB | 60.15 | 0.08 | 96.84 | 62.11 | 0.11 | 96.60 | 3.47 |
| Group 56 | 0.05% PVA11 + 0.05M NaCl + 0.1M NaA | 85.67 | 0.05 | 95.88 | 104.10 | 0.22 | 87.25 | 45.46 |
| Group 57 | 0.05% PVA11 + 0.05M NaCl + 0.1M NaS | 84.85 | 0.02 | 96.52 | 113.70 | 0.10 | 96.31 | 55.06 |
| Group 58 | 0.05% PVA11 + 0.05M NaCl + 0.1% PS20 | 60.25 | 0.08 | 96.20 | 72.99 | 0.12 | 72.84 | 14.35 |

The results show that the selected formulation from Example 9 (0.050% PVA+0.05M NaCl+0.1M KS) is reproducible and provides good results with respect to particle size preservation (delta), PDI, and percent encapsulation even at higher concentrations of RNA (see Groups 41, 42, and 43). Under some conditions, sodium benzoate (NaB) also showed good results (Groups 44 and 55). Polysorbate20 was also shown to be a good cryoprotectant, maintaining the integrity of the lipid particles even at 0.050% w/v (Group 36) but not as a lyoprotectant. Other salts and excipients tested did not show an effectiveness equivalent to potassium sorbate.

Example 11: Studies on Formulation Free of PVA

In this experiment, the previous learnings were applied to see if the lipid nanoparticles could be lyophilized without using PVA and instead using hydrophobic salts in combination with human albumin. The lipid nanoparticle formulation was prepared as described in Example 1 and the lyophilization cycle of Example 5 was applied. The specific conditions and results are provided in Table 12 below.

TABLE 12

Studies on Removing PVA

| Group No. | Conditions | Size (nm) F/T | (nm) F/T | PDI F/T | Size % Encap Post | PDI POST | % Encap Post |
|---|---|---|---|---|---|---|---|
| Group 1 | 1% HA + 0.05M KS | 64.76 | 0.09 | 81.09 | 73.90 | 0.17 | 89.02 |
| Group 2 | 1% HA + 0.01M KS | 66.44 | 0.09 | 83.50 | 79.87 | 0.22 | 80.71 |
| Group 3 | 0.5% HA + 0.2M KS | 80.71 | 0.10 | 89.71 | 79.58 | 0.13 | 92.78 |
| Group 4 | 0.5% HA + 0.1M KS | 71.77 | 0.11 | 89.38 | 76.72 | 0.13 | 91.92 |
| Group 5 | 0.5% HA + 0.05M KS | 66.64 | 0.10 | 87.09 | 73.93 | 0.16 | 90.10 |
| Group 6 | 0.5% HA + 0.05M KS (0.5 mg/ml) | 67.52 | 0.11 | 88.96 | 78.01 | 0.17 | 91.64 |
| Group 7 | 0.5% HA + 0.05M KS (1.0 mg/ml) | 68.23 | 0.11 | 91.62 | 81.47 | 0.16 | 93.70 |
| Group 8 | 0.5% HA + 0.01M KS | 66.83 | 0.09 | 84.48 | 76.37 | 0.15 | 81.98 |
| Group 9 | 0.3% HA + 0.2M KS | 82.08 | 0.09 | 91.92 | 81.71 | 0.09 | 93.38 |
| Group 10 | 0.3% HA + 0.1M KS | 77.32 | 0.09 | 85.99 | 77.89 | 0.13 | 93.06 |
| Group 11 | 0.3% HA + 0.05M KS | 68.41 | 0.11 | 83.03 | 76.36 | 0.14 | 91.71 |
| Group 12 | 1% HA + 0.05M KS + 0.05M NaCl | 68.98 | 0.10 | 82.42 | 74.96 | 0.17 | 87.59 |
| Group 13 | 1% HA + 0.01M KS + 0.05M NaCl | 69.34 | 0.16 | 81.66 | 78.31 | 0.21 | 80.50 |

TABLE 12-continued

Studies on Removing PVA

| Group No. | Conditions | Size (nm) F/T | PDI F/T | (nm) F/T | Size % Encap Post | PDI POST | % Encap Post |
|---|---|---|---|---|---|---|---|
| Group 14 | 0.5% HA + 0.2M KS + 0.05M NaCl | 89.65 | 0.07 | 92.97 | 82.39 | 0.14 | 92.77 |
| Group 15 | 0.5% HA + 0.1M KS + 0.05M NaCl | 75.13 | 0.08 | 89.37 | 78.77 | 0.14 | 91.66 |
| Group 16 | 0.5% HA + 0.05M KS + 0.05M NaCl | 68.05 | 0.12 | 89.26 | 81.92 | 0.15 | 89.82 |
| Group 17 | 0.5% HA + 0.01M KS + 0.05M NaCl | 66.80 | 0.10 | 84.60 | 75.22 | 0.17 | 82.99 |
| Group 18 | 0.3% HA + 0.2M KS + 0.05M NaCl | 87.44 | 0.07 | 93.68 | 80.17 | 0.15 | 93.15 |
| Group 19 | 0.3% HA + 0.1M KS + 0.05M NaCl | 69.60 | 0.07 | 90.99 | 79.42 | 0.12 | 92.79 |
| Group 20 | 0.3% HA + 0.05M KS + 0.05M NaCl | 68.37 | 0.09 | 90.39 | 79.70 | 0.13 | 90.12 |
| Group 21 | 0.5% HA + 0.1M KS + 0.01M NaCl | 68.75 | 0.09 | 89.80 | 79.68 | 0.14 | 92.07 |
| Group 22 | 0.5% HA + 0.1M KS + 0.1M NaCl | 66.99 | 0.09 | 89.64 | 83.99 | 0.13 | 90.36 |
| Group 23 | 0.5% HA + 0.1M KS + 0.2M NaCl | 65.66 | 0.10 | 90.02 | 97.41 | 0.14 | 73.66 |
| Group 24 | 0.5% HA + 0.1M KS + 0.01M MgCl$_2$ | 68.85 | 0.09 | 90.26 | 84.35 | 0.12 | 89.05 |
| Group 25 | 0.5% HA + 0.1M KS + 0.05M MgCl$_2$ | 86.50 | 0.07 | 91.10 | 125.90 | 0.07 | 87.45 |
| Group 26 | 0.5% HA + 0.1M KS + 0.1M MgCl$_2$ | 97.81 | 0.07 | 93.60 | 190.70 | 0.12 | 84.93 |
| Group 27 | 0.5% HA + 0.1M KS + 0.2M MgCl$_2$ | 118.70 | 0.10 | 95.50 | 206.10 | 0.12 | 84.31 |
| Group 28 | 0.3% HA + 0.05M KS + 0.05M MgCl$_2$ | 68.19 | 0.08 | 89.40 | 79.99 | 0.11 | 89.32 |
| Group 29 | 0.5% HA + 0.1M KS + 0.01M NH4SO4 | 74.39 | 0.09 | 96.50 | 84.23 | 0.11 | 96.19 |
| Group 30 | 0.5% HA + 0.1M KS + 0.05M NH4SO4 | 74.43 | 0.05 | 96.10 | 89.11 | 0.09 | 96.31 |
| Group 31 | 0.5% HA + 0.1M KS + 0.1M NH4SO4 | 81.07 | 0.12 | 96.30 | 139.50 | 0.14 | 93.28 |
| Group 32 | 0.5% HA + 0.1M KS + 0.2M NH4SO4 | 120.60 | 0.18 | 96.30 | 159.90 | 0.28 | 89.34 |
| Group 33 | 0.3% HA + 0.05M KS + 0.05M NH4SO4 | 76.41 | 0.09 | 96.50 | 96.72 | 0.24 | 97.26 |
| Group 34 | 1% HA + 0.1M NaB + 0.01M NaCl | 93.80 | 0.24 | 86.80 | 78.66 | 0.16 | 90.87 |
| Group 35 | 1% HA + 0.1M NaB + 0.01M MgCl2 | 73.44 | 0.08 | 84.90 | 81.62 | 0.16 | 87.86 |
| Group 36 | 1% HA + 0.1M NaB + 0.05M MgCl2 | 76.38 | 0.08 | 88.70 | 87.12 | 0.11 | 86.14 |
| Group 37 | 1% HA + 0.1M NaB + 0.1M MgCl2 | 76.73 | 0.10 | 93.30 | 153.30 | 0.20 | 77.51 |
| Group 38 | 1% HA + 0.1M NaB + 0.01M NH4SO4 | 77.47 | 0.09 | 96.20 | 84.65 | 0.17 | 96.02 |
| Group 39 | 1% HA + 0.1M NaB + 0.05M NH4SO4 | 86.77 | 0.07 | 96.00 | 91.95 | 0.12 | 95.77 |
| Group 40 | 1% HA + 0.1M NaB + 0.1M NH4SO4 | 93.92 | 0.13 | 95.70 | 105.50 | 0.14 | 94.91 |
| Group 41 | 0.5% HA + 0.1M NaB + 0.01M MgCl2 | | | 86.50 | 81.37 | 0.14 | 90.85 |
| Group 42 | 0.5% HA + 0.1M NaB + 0.05M MgCl2 | | | 91.00 | 96.45 | 0.12 | 86.67 |
| Group 43 | 0.5% HA + 0.1M NaB + 0.1M MgCl2 | | | 95.30 | 213.90 | 0.34 | 72.77 |
| Group 44 | 0.5% HA + 0.1M NaB + 0.01M NH4SO4 | | | 96.40 | 86.53 | 0.14 | 95.65 |
| Group 45 | 0.5% HA + 0.1M NaB + 0.05M NH4SO4 | | | 96.10 | 95.01 | 0.14 | 95.61 |
| Group 46 | 0.5% HA + 0.1M NaB + 0.1M NH4SO4 | | | 95.80 | 107.60 | 0.13 | 93.56 |
| Group 47 | 0.05% PVA14 + 0.05M NaCl | | | 94.60 | 95.62 | 0.34 | 82.22 |
| Group 48 | 0.05% PVA14 + 0.05M MgCl2 | | | 95.40 | 87.05 | 0.41 | 81.95 |
| Group 49 | 0.05% PVA14 + 0.05M NH4SO4 | | | 96.50 | 365.30 | 0.33 | 85.34 |
| Group 50 | 0.05% PVA15 + 0.05M NaCl | | | 96.50 | 79.92 | 0.14 | 90.88 |

TABLE 12-continued

Studies on Removing PVA

| Group No. | Conditions | Size (nm) F/T | PDI F/T | Size (nm) % Encap Post | PDI POST | % Encap Post |
|---|---|---|---|---|---|---|
| Group 51 | 0.05% PVA15 + 0.05M MgCl2 | | | 97.40 73.71 | 0.10 | 91.56 |
| Group 52 | 0.05% PVA15 + 0.05M NH4SO4 | | | 97.00 204.20 | 0.23 | 95.08 |
| Group 53 | 0.05% PVA10 + 0.05M NaCl + 0.1M KS (1.0 mg/ml) | | | 96.50 67.32 | 0.12 | 97.73 |
| Group 54 | 0.05% PVA10 + 0.05M NaCl + 0.1M NB (1.0 mg/ml) | | | 96.80 75.14 | 0.10 | 98.03 |

The results show that the replacement of PVA with hydrophobic salts in combination with human albumin (HA) does not produce an adequate lyophilized lipid nanoparticle formulation.

Example 12: Studies on Alternative Excipients

This study was designed to test whether potassium sorbate could be replaced by other excipients. The study also evaluated how these excipients work at a reduced concentration of RNA, and were performed at a concentration of 0.25 mg RNA/mL. The excipients tested included iodixanol and L-proline (Pro). The lipid nanoparticle formulations were prepared as described in Example 1 and the lyophilization cycle of Example 5 was applied. The specific conditions for the pretreated suspensions as compared to freeze-thaw formulations and the corresponding results are provided in Table 13.

TABLE 13

Studies on Alternative Excipients and Lower RNA Concentration

| Group No. | Conditions | Size (nm) F/T | PDI F/T | % Encap F/T | Size (nm) Post | PDI Post | % Encap Post | δ |
|---|---|---|---|---|---|---|---|---|
| Group 1 | 0.05% PVA10 + 0.05M NaCl + 0.1M KS (1.0 mg/ml) | 61.08 | 0.073 | 95.07 | 67.87 | 0.09 | 96.70 | 9.15 |
| Group 2 | 0.025% PVA10 + 0.025M NaCl + 0.05M KS (0.5 mg/ml) | 61.63 | 0.09 | 93.75 | 66.73 | 0.12 | 95.40 | 8.01 |
| Group 3 | 0.0125% PVA10 + 0.0125M NaCl + 0.025M KS (0.25 mg/ml) | 61.54 | 0.099 | 94.02 | 67.35 | 0.13 | 91.90 | 8.63 |
| Group 4 | 0.05% PVA10 + 0.05M NaCl | 69.45 | 0.067 | 94.05 | 76.66 | 0.11 | 85.60 | 17.94 |
| Group 5 | 0.05% PVA10 + 0.1M MgCl2 | 61.07 | 0.088 | 97.97 | 68.14 | 0.13 | 89.40 | 9.42 |
| Group 6 | 0.05% PVA10 + 0.05M MgCl2 | 61.35 | 0.196 | 97.56 | 69.90 | 0.14 | 89.00 | 11.18 |
| Group 7 | 0.05% PVA10 + 0.01M MgCl2 | 67.93 | 0.062 | 94.93 | 77.38 | 0.14 | 88.50 | 18.66 |
| Group 8 | 0.05% PVA10 + 0.05M NaCl + 0.1M NaB | 62.77 | 0.064 | 94.47 | 63.98 | 0.09 | 96.60 | 5.26 |
| Group 9 | 0.05% PVA10 + 0.05M NaCl + 0.1M NaB (0.5 mg/ml) | 62.76 | 0.088 | 95.51 | 67.05 | 0.09 | 96.90 | 8.33 |
| Group 10 | 0.05% PVA10 + 0.05M NaCl + 0.1M NaB (1.0 mg/ml) | 62.99 | 0.092 | 96.29 | 73.79 | 0.12 | 97.30 | 15.07 |
| Group 11 | 0.05% PVA10 + 0.1M Pro | 78.94 | 0.05 | 92.21 | 92.38 | 0.09 | 87.20 | 33.66 |
| Group 12 | 0.05% PVA10 + 0.05M Pro | 73.63 | 0.036 | 93.34 | 86.38 | 0.07 | 87.50 | 27.66 |
| Group 13 | 0.05% PVA10 + 0.01M Pro | 70.21 | 0.087 | 93.87 | 79.65 | 0.10 | 81.87 | 20.93 |
| Group 14 | 0.05% PVA10 + 0.05M NaCl + 0.1M Pro | 76.51 | 0.056 | 94.10 | 88.69 | 0.10 | 77.01 | 29.97 |
| Group 15 | 0.05% PVA10 + 0.05M NaCl + 0.01M Pro | 68.78 | 0.069 | 94.07 | 79.16 | 0.07 | 85.92 | 20.44 |
| Group 16 | 0.05% PVA10 + 0.1M MgCl2 + 9% Iodixanol | 60 | 0.088 | 98.14 | 67.22 | 0.13 | 94.56 | 8.50 |
| Group 17 | 0.05% PVA10 + 0.05M MgCl2 + 9% Iodixanol | 60.13 | 0.098 | 97.97 | 65.44 | 0.17 | 94.62 | 6.72 |
| Group 18 | 0.05% PVA10 + 0.01M MgCl2 + 9% Iodixanol | 61.01 | 0.102 | 96.08 | 67.49 | 0.15 | 93.81 | 8.77 |
| Group 19 | 0.05% PVA10 + 0.05M NaCl + 0.1M NaB + 9% Iodixanol | 68.09 | 0.223 | low volume | 63.53 | 0.09 | 96.11 | 4.81 |
| Group 20 | 0.05% PVA10 + 0.05M NaCl + 0.1M NaB (0.5 mg/ml) + 9% Iodixanol | 62.73 | 0.081 | 95.77 | 74.30 | 0.19 | 93.87 | 15.58 |
| Group 21 | 0.05% PVA10 + 0.05M NaCl + 0.1M NaB (1.0 mg/ml) + 9% Iodixanol | 62.4 | 0.075 | 95.72 | 79.14 | 0.22 | 95.03 | 20.42 |
| Group 22 | 0.05% PVA10 + 0.1M Pro + 9% Iodixanol | 60.18 | 0.101 | 94.22 | 65.30 | 0.16 | 93.50 | 6.58 |
| Group 23 | 0.05% PVA10 + 0.05M Pro + 9% Iodixanol | 61.16 | 0.077 | 93.70 | 66.60 | 0.17 | 93.79 | 7.88 |
| Group 24 | 0.05% PVA10 + 0.01M Pro + 9% Iodixanol | 60.61 | 0.095 | 94.03 | 66.84 | 0.15 | 93.52 | 8.12 |
| Group 25 | 0.05% PVA10 + 0.05M NaCl + 0.1M Pro + 9% Iodixanol | 60.17 | 0.093 | 95.56 | 66.55 | 0.14 | 93.95 | 7.83 |

TABLE 13-continued

Studies on Alternative Excipients and Lower RNA Concentration

| Group No. | Conditions | Size (nm) F/T | PDI F/T | % Encap F/T | Size (nm) Post | PDI Post | % Encap Post | δ |
|---|---|---|---|---|---|---|---|---|
| Group 26 | 0.05% PVA10 + 0.05M NaCl + 0.01M Pro + 9% Iodixanol | 60.68 | 0.133 | 96.19 | 66.88 | 0.12 | 94.11 | 8.16 |
| Group 27 | 0.5% HA + 0.2M Pro | 73.93 | 0.089 | 72.70 | 84.84 | 0.18 | 63.11 | 26.12 |
| Group 28 | 0.5% HA + 0.1M Pro | 69.56 | 0.093 | 69.93 | 76.94 | 0.17 | 66.29 | 18.22 |
| Group 29 | 0.5% HA + 0.05M Pro | 66.49 | 0.108 | 71.95 | 72.78 | 0.20 | 65.97 | 14.06 |
| Group 30 | 0.5% HA + 0.1M KS + 0.05M Pro | 79.02 | 0.112 | 84.09 | 79.14 | 0.11 | 90.43 | 20.42 |
| Group 31 | 0.5% HA + 0.1M KS + 0.01M Pro | 78.15 | 0.102 | 84.75 | 82.78 | 0.15 | 90.68 | 24.06 |
| Group 32 | 0.5% HA + 0.2M Pro + 9% Iodixanol | 61.73 | 0.114 | 73.13 | 71.97 | 0.24 | 69.13 | 13.25 |
| Group 33 | 0.5% HA + 0.1M Pro + 9% Iodixanol | 61.84 | 0.094 | 76.72 | 67.91 | 0.22 | 72.75 | 9.19 |
| Group 34 | 0.5% HA + 0.05M Pro + 9% Iodixanol | 61.88 | 0.084 | 75.05 | 68.54 | 0.22 | 74.31 | 9.82 |
| Group 35 | 0.5% HA + 0.1M KS + 0.05M Pro + 9% Iodixanol | 81.68 | 0.133 | 83.11 | 71.86 | 0.14 | 91.72 | 13.14 |
| Group 36 | 0.5% HA + 0.1M KS + 0.01M Pro + 9% Iodixanol | 81.65 | 0.126 | 90.06 | 71.07 | 0.15 | 91.47 | 12.35 |
| Group 37 | 0.05% PVA10 + 0.05% PS80 | 61.41 | 0.087 | 95.34 | 76.83 | 0.17 | 76.85 | 18.11 |
| Group 38 | 0.05% PVA10 + 0.05M NaCl + 0.1% PS80 | 61.79 | 0.099 | 94.35 | 77.02 | 0.14 | 70.98 | 18.30 |
| Group 39 | 0.05% PVA10 + 0.01% PS80 | 60.12 | 0.132 | 94.23 | 73.18 | 0.12 | 82.58 | 14.46 |
| Group 40 | 0.05% PVA10 + 0.05M NaCl + 0.1% PS80 | 62.12 | 0.127 | 95.12 | 77.10 | 0.11 | 68.00 | 18.38 |
| Group 41 | 1% HA + 0.05% PS80 | 65.61 | 0.151 | 96.88 | 79.63 | 0.22 | 76.83 | 20.91 |
| Group 42 | 0.5% HA + 0.05% PS80 | 63.15 | 0.092 | 96.97 | 75.90 | 0.19 | 73.41 | 17.18 |
| Group 43 | 0.05% PVA10 + 0.05% PS80 + 9% Iodixanol | 62.15 | 0.083 | 93.15 | 68.33 | 0.16 | 90.87 | 9.61 |
| Group 44 | 0.05% PVA10 + 0.05M NaCl + 0.1% PS80 + 9% Iodixanol | 62.55 | 0.11 | 92.97 | 66.91 | 0.16 | 90.01 | 8.19 |
| Group 45 | 0.05% PVA10 + 0.01% PS80 + 9% Iodixanol | 61.11 | 0.193 | 94.16 | 67.98 | 0.16 | 91.63 | 9.26 |
| Group 46 | 0.05% PVA10 + 0.05M NaCl + 0.1% PS80 + 9% Iodixanol | 62.9 | 0.098 | 93.07 | 67.49 | 0.15 | 90.13 | 8.77 |
| Group 47 | 1% HA + 0.05% PS80 + 9% Iodixanol | 59.6 | 0.111 | 97.53 | 66.95 | 0.18 | 96.28 | 8.23 |
| Group 48 | 0.5% HA + 0.05% PS80 + 9% Iodixanol | 60.62 | 0.084 | 97.73 | 67.18 | 0.16 | 95.56 | 8.46 |

The results of this study indicate that the concentration of the excipients used in the pretreated formulation can be reduced so long as the same ratio of excipient to RNA is used (See Groups 1-3). Sodium benzoate (NaB) showed results on the same level as potassium sorbate (KS) at the 0.25 mg RNA/mL. The experiments with L-proline showed that it was not an effective substitute for potassium sorbate. In contrast, iodixanol was shown to be a potent lyoprotectant, and even improved formulations that had PVA and proline (Groups 22-26), but can also be used in formulations that do not include PVA (Groups 47 and 48).

Example 12: In Vivo Testing of Reconstituted Formulations

Selected formulations from the studies of previous examples were tested for in vivo efficacy. Lipid nanoparticles comprising 0.25 mg/mL of a mRNA encoding the human EPO protein (hEPO), a common test for the ability to successfully transfect a specimen and measure the efficiency of translation of the mRNA in vivo. The formulations were lyophilized using the lyophilization cycle of Example 5 in an amount calculated to achieve final volumes of 3.0 mL. The experiments also included measurement of a control freeze-thaw formulation in 5% glycerol and a negative PBS control. The conditions of the formulations are provided in Table 14, which also shows the characterization of these formulations prior to the in vivo studies.

TABLE 14

Conditions and Characterization of Formulations Used in In Vivo Studies

| Composition No. | Conditions | Size (nm) Post | PDI Post | % Encap |
|---|---|---|---|---|
| 1 | 0.025% PVA10 + 0.025M NaCl + 0.05M KS | 75.93 | 0.12 | 94.40 |
| 2 | 0.05% PVA10 + 0.05M NaCl + 0.1M NaB | 82.21 | 0.11 | 96.16 |
| 3 | 0.05% PVA10 + 0.1M Pro + 9% Iodixanol | 70.45 | 0.18 | 93.31 |
| 4 | 1% HA + 0.05% PS80 + 9% Iodixanol | 70.95 | 0.16 | 92.43 |
| 9 | 5% Glycerol (frozen control) | NA | NA | NA |
| 10 | 5% Glycerol (frozen control) | NA | NA | NA |
| 11 | PBS | NA | NA | NA |

Figure 4:
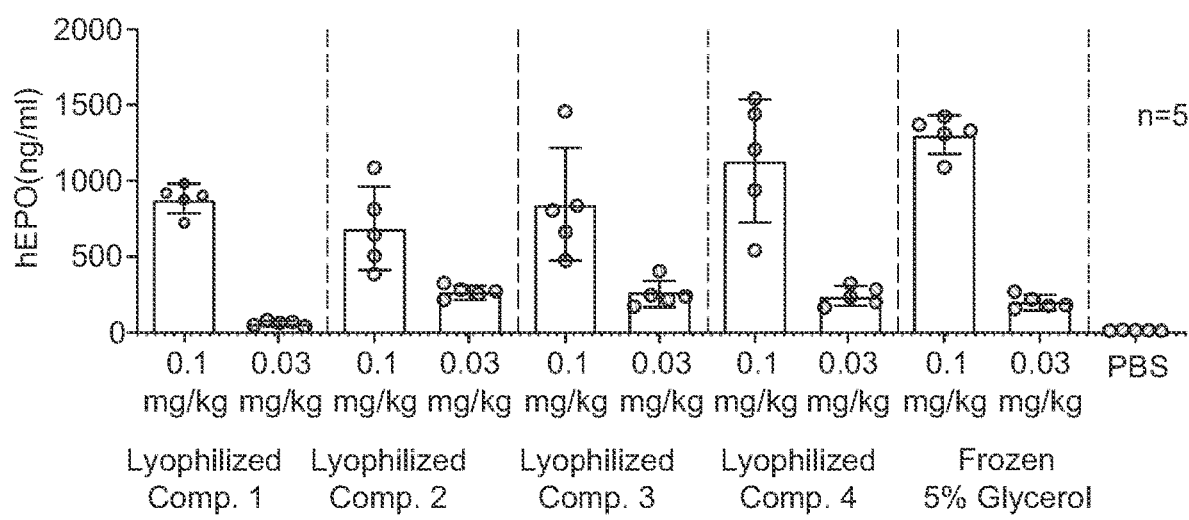
FIG. 4 shows human erythropoietin (hEPO) expression levels for selected reconstituted formulations in comparison to the freeze-thaw control and PBS negative control as described in Example 12.

The results of the study are shown in FIG. 4. All reconstituted formulations showed good hEPO expression, with compositions 3 and 4 showing expression close to the freeze-thaw control.

Example 13: Testing of Different Formulations with a Large mRNA

The lyophilization compositions developed in previous examples were tested to see if they could be applied to mRNA-lipid nanoparticle formulations in which the mRNA has a large size. Two mRNAs were tested, mRNA1, which had a size of about 1332 nucleotides, and mRNA2, which had a size of about 4868 nucleotides. The formulations were prepared as described in Example 1, and the lyophilization cycle of Example 5 was applied. The conditions for the lyophilization studies and the results are provided in Table 15.

The results indicate the lyophilization formulations work for mRNA constructs that are large in size. In particular, the formulations of Groups 25, 26, and 27 showed excellent results upon reconstitution.

Example 14: Additional Formulations

This experiment tested the effect of P188 and other combinations on lyophilized lipid nanoparticle formulations using mRNA2. The lipid nanoparticle formulations were prepared as described in Example 1 and the lyophilization cycle of Example 5 was applied. The specific conditions of the formulations and the results for the pos-lyophilization and reconstituted formulations are provided in Table 16.

TABLE 15

Lyophilization Experiments with Large mRNAs

| Group No. | Conditions | Size (nm) Pre | PDI Pre | % Encap Pre | Size (nm) Post | PDI Post | % Encap | δ |
|---|---|---|---|---|---|---|---|---|
| 1 | 0.025% PVA10 + 0.025M NaCl + 0.05M KS (MRNA1 400 mg/ml) | 72.86 | 0.126 | 99.30 | 88.98 | 0.16 | 99.21 | 20.07 |
| 2 | 0.025% PVA10 + 0.025M NaCl + 0.05M KS (MRNA1 250 mg/ml) | 73.74 | 0.132 | | 91.16 | 0.14 | 99.17 | 22.25 |
| 3 | 0.025% PVA10 + 0.025M NaCl + 0.05M KS (MRNA1 100 mg/ml) | 75.59 | 0.152 | 99.40 | 94.65 | 0.20 | 98.94 | 25.74 |
| 4 | 0.05% PVA10 + 0.05M NaCl + 0.1M KS (MRNA1 400 mg/ml) | 71.62 | 0.171 | 99.30 | 108.80 | 0.20 | 99.04 | 39.89 |
| 5 | 0.05% PVA10 + 0.05M NaCl + 0.1M KS (MRNA1 250 mg/ml) | 83.59 | 0.147 | 99.30 | 157.10 | 0.20 | 97.87 | 88.19 |
| 6 | 0.05% PVA10 + 0.05M NaCl + 0.1M KS (MRNA1 100 mg/ml) | 117.2 | 0.173 | 94.96 | 156.70 | 0.15 | 89.75 | 87.79 |
| 8 | 0.05% PVA10 + 0.05M NaCl + 0.1M NaB (MRNA1 250 mg/ml) | 70.95 | 0.113 | | 93.60 | 0.20 | 99.14 | 24.69 |
| 9 | 0.05% PVA10 + 0.05M NaCl + 0.1M NaB (MRNA1 100 mg/ml) | 71.72 | 0.122 | 99.40 | 93.10 | 0.18 | 98.95 | 24.19 |
| 11 | 0.05% PVA10 + 0.1M Pro + 9% Iodixanol (MRNA1 250 mg/ml) | 69.75 | 0.101 | 99.43 | 74.24 | 0.16 | 99.38 | 5.33 |
| 12 | 0.05% PVA10 + 0.1M Pro + 9% Iodixanol (MRNA1 100 mg/ml) | 69.37 | 0.125 | 99.52 | 75.44 | 0.18 | 99.44 | 6.53 |
| 14 | 1% HA + 0.05% PS80 + 9% Iodixanol (MRNA1 250 mg/ml) | 89.83 | 0.214 | 99.26 | 112.80 | 0.25 | 99.07 | 43.89 |
| 16 | 0.025% PVA10 + 0.025M NaCl + 0.05M KS (MRNA2 400 mg/ml) | 77.53 | 0.138 | 99.3 | 92.17 | 0.192 | 99.1269 | 19.04 |
| 17 | 0.025% PVA10 + 0.025M NaCl + 0.05M KS (MRNA2 250 mg/ml) | 78.24 | 0.131 | 99.4 | 89.31 | 0.186 | 99.17 | 16.18 |
| 18 | 0.025% PVA10 + 0.025M NaCl + 0.05M KS (MRNA2 100 mg/ml) | 76.85 | 0.14 | 99.3 | 89.35 | 0.198 | 99.08 | 16.22 |
| 20 | 0.05% PVA10 + 0.05M NaCl + 0.1M KS (MRNA2 250 mg/ml) | 87.75 | 0.16 | 99.20 | 159.50 | 0.24 | 98.16 | 86.37 |
| 21 | 0.05% PVA10 + 0.05M NaCl + 0.1M KS (MRNA2 100 mg/ml) | 95.14 | 0.193 | 99.00 | 171.60 | 0.21 | 97.49 | 98.47 |
| 23 | 0.05% PVA10 + 0.05M NaCl + 0.1M NaB (MRNA2 250 mg/ml) | 74.64 | 0.104 | 99.4 | 92.54 | 0.198 | 99.12 | 19.41 |
| 24 | 0.05% PVA10 + 0.05M NaCl + 0.1M NaB (MRNA2 100 mg/ml) | 75.04 | 0.132 | 99.3 | 89.64 | 0.162 | 99.11 | 16.51 |
| 25 | 0.05% PVA10 + 0.1M Pro + 9% Iodixanol (MRNA2 400 mg/ml) | 74.75 | 0.084 | 99.3 | 78.39 | 0.136 | 99.2 | 5.26 |
| 26 | 0.05% PVA10 + 0.1M Pro + 9% Iodixanol (MRNA2 250 mg/ml) | 74.04 | 0.107 | 99.3 | 76.53 | 0.129 | 99.3 | 3.4 |
| 27 | 0.05% PVA10 + 0.1M Pro + 9% Iodixanol (MRNA2 100 mg/ml) | 73.29 | 0.104 | 99.3 | 76.78 | 0.164 | 99.28 | 3.65 |
| 28 | 1% HA + 0.05% PS80 + 9% Iodixanol (MRNA2 400 mg/ml) | 91.06 | 0.206 | 99.3 | 105.1 | 0.209 | 99.21 | 31.97 |
| 29 | 1% HA + 0.05% PS80 + 9% Iodixanol (MRNA2 250 mg/ml) | 88.87 | 0.228 | 99.2 | 108.3 | 0.228 | 99.16 | 35.17 |
| 30 | 1% HA + 0.05% PS80 + 9% Iodixanol (MRNA2 100 mg/ml) | 79.09 | 0.179 | 98.7 | 107 | 0.33 | 98.63 | 33.87 |

TABLE 16

Lyophilization Studies of Further Combinations

| Group No. | Conditions | Size (nm) Post | PDI Post | % Encap Post | δ |
|---|---|---|---|---|---|
| Group 1 | 0.035% PVA10 + 0.1M Pro + 0.2% Kol P188 + 9% Suc | 90.54 | 0.12 | 99.31 | 13.76 |
| Group 2 | 0.035% PVA10 + 0.05M Pro + 0.2% Kol P188 + 9% Suc | 85.68 | 0.13 | 99.27 | 8.90 |
| Group 3 | 0.035% PVA10 + 0.025M Pro + 0.2% Kol P188 + 9% Suc | 126.80 | 0.20 | 98.68 | 50.02 |
| Group 4 | 0.035% PVA10 + 0.1M Pro + 0.1% Kol P188 + 9% Suc | 88.11 | 0.12 | 99.41 | 11.33 |
| Group 5 | 0.035% PVA10 + 0.05M Pro + 0.1% Kol P188 + 9% Suc | 104.60 | 0.14 | 99.07 | 27.82 |
| Group 6 | 0.035% PVA10 + 0.025M Pro + 0.1% Kol P188 + 9% Suc | 89.57 | 0.12 | 99.22 | 12.79 |
| Group 7 | 0.035% PVA10 + 0.1M Pro + 0.05% Kol P188 + 9% Suc | 86.52 | 0.15 | 99.23 | 9.74 |
| Group 8 | 0.035% PVA10 + 0.05M Pro + 0.05% Kol P188 + 9% Suc | 87.99 | 0.13 | 99.22 | 11.21 |
| Group 9 | 0.035% PVA10 + 0.025M Pro + 0.05% Kol P188 + 9% Suc | 92.55 | 0.13 | 99.06 | 15.77 |
| Group 10 | 0.035% PVA10 + 0.1M Pro + 0.2% Kol P188 + 9% Suc | 87.66 | 0.129 | 99.31 | 10.88 |
| Group 11 | 0.035% PVA10 + 0.1M Pro + 0.2% Kol P188 | 95.97 | 0.114 | 99.23 | 19.19 |
| Group 13 | 0.035% PVA10 + 0.05M Pro + 9% Suc | 88.27 | 0.141 | 99.26 | 11.49 |
| Group 14 | 0.035% PVA10 + 0.025M Pro + 9% Suc | 93.69 | 0.144 | 99.23 | 16.91 |
| Group 17 | 0.05% PVA10 + 0.1M Pro + 9% Iodixanol | 83.55 | 0.135 | 99.36 | 6.77 |

The results show that formulations other than those including iodixanol can be used, as all the tested groups showed encapsulation efficiency above 99%. In addition, Groups and 7 showed δ values close to those for Group 17, which used iodixanol.

Example 15: Lyophilization of a Self-Replicating RNA

Self-Replicating RNAs (aka Replicon RNA) are typically larger than the average mRNA, and tests were designed to determine whether self-replicating RNA lipid nanoparticle formulations could be successfully lyophilized.

The formulations were prepared as described in Example 1, with self-replicating RNA concentrations in the range of 0.10 to 2.0 mg/mL. The following lyophilization cycle was used:

Initial Freeze (shelf temperature): −52° C., 30 minutes
Freeze for additional 5 minutes, vacuum set point 300 mTorr
Primary Drying:
1. −48° C., maintain 30 minutes, vacuum set point 50 mTorr
2. −40° C. for 15 to 60 minutes, vacuum set point 50 mTorr
3. Maintain −40° C., vacuum set point 50 mTorr, until pressure difference of 4 mTorr is reached. (the pressure difference indicates a change in the relative humidity in the lyophilization chamber).
Secondary Drying at 5° C., vacuum set point 100 mTorr for 1200 minutes.

Each of the following formulation conditions shown in Table 17 were tested:

TABLE 17

Formulations used for Self-replicating RNA Lyophilization

9% Sucrose
0.05M potassium sorbate
0.025M NaCl + 0.05M potassium sorbate
0.025M potassium sorbate
0.025M NaCl + 0.025M potassium sorbate
0.025% PVA PVA(4-88) + 0.025M NaCl + 0.2M potassium sorbate
0.025M NaCl + 0.05M potassium sorbate + 0.1% sodium thiosulfate TABLE 17-continued Formulations used for Self-replicating RNA Lyophilization (5-15)% sucrose + (.01-0.5)M potassium sorbate
(5-15)% sucrose + (0.025-1.0)% sodium thiosulfate
(0.01-0.75)% PVA(4-88) + (.005-0.5)M NaCl + (0.01-0.5)M potassium sorbate + (5-15)% sucrose + (0.025-1.0)% sodium thiosulfate The results for the above conditions were found to produce lyophilized lipid nanoparticle formulations with adequate size, polydispersity, and delta values upon reconstitution.

Example 15: Lyophilization of Self-Replicating RNA-Lipid Nanoparticle Formulation The processes conducted in this example were conducted using lipid nanoparticle compositions that were manufactured according to well-known processes, for example, those described in U.S. application Ser. No. 16/823,212, the contents of which are incorporated by reference for the specific purpose of teaching lipid nanoparticle manufacturing processes. The lipid nanoparticle compositions and the lyophilized products were characterized for several properties. The materials and methods for these characterization processes as well as a general method of manufacturing the lipid nanoparticle compositions that were used for lyophilization experiments are provided in this example.

Lipid Nanoparticle Manufacture

Lipid nanoparticle formulations used in this example were manufactured by mixing lipids (ionizable cationic lipid (ATX-126):helper lipid:cholesterol:PEG-lipid) in ethanol with RNA dissolved in citrate buffer. The mixed material was instantaneously diluted with Phosphate Buffer. Ethanol was removed by dialysis against phosphate buffer using regenerated cellulose membrane (100 kD MWCO) or by tangential flow filtration (TFF) using modified polyethersulfone (mPES) hollow fiber membranes (100 kD MWCO). Once the ethanol was completely removed, the buffer was exchanged with HEPES (4-(2-hydroxyethyl)-1-piperazineethanesulfonic acid) buffer containing 10-300 (for example, 40-60) mM NaCl and 5-15% sucrose, pH 7.3. The formulation was concentrated followed by 0.2 μm filtration using PES filters. The RNA concentration in the formulation was then measured by RIBOGREEN™ fluorimetric assay, and the concentration was adjusted to a final desired concentration by diluting with HEPES buffer containing 10-100 (for example 40-60) mM NaCl, 0-15% sucrose, pH 7.2-8.5 containing glycerol. If not used immediately for further studies, the final formulation was then filtered through a 0.2 µm filter and filled into glass vials, stoppered, capped and placed at −70±5° C. The lipid nanoparticles formulations were characterized for their pH and osmolality. Lipid Content and RNA content were measured by high performance liquid chromatography (HPLC), and mRNA integrity by was measured by fragment analyzer.

Lyophilization Process

Self-Replicating RNAs (aka Replicon RNA) are typically larger than the average mRNA, and tests were designed to determine whether self-replicating RNA lipid nanoparticle formulations could be successfully lyophilized. The quality of lyophilized lipid nanoparticle formulations was assessed by analyzing the formulations post-lyophilization and comparing this to the lipid nanoparticle formulation prior to lyophilization as well as after a conventional freeze/thaw cycle (i.e., frozen at ∼−70° C. then allowed to thaw at room temperature).

The analysis of the lipid nanoparticle formulations included the analysis of particle size and polydispersity (PDI) and encapsulation efficiency (% Encap). The particle size post-lyophilization was compared to the particle size pre-lyophilization and the difference can be reported as a delta ($\delta$). The various compositions tested were screened as to whether a threshold of properties was met including minimal particle size increase ($\delta<10$ nm), the maintenance of PDI ($<0.2$), and maintenance of high encapsulation efficiency ($>85\%$).

The lipid nanoparticle formulations were prepared as described above, with self-replicating RNA of over 11,000 nucleotides in length. The resulting lipid nanoparticle formulation was then processed with a buffer exchange to form a prelyophilization suspension having a concentration of 0.05 to 2.0 mg/mL self-replicating RNA, 0.01 to 0.05 M potassium sorbate, 0.01 to 0.10% w/v Poloxamer 188 (Kolliphor®), 14 to 18% w/v sucrose, 25 to 75 mM NaCl, and 15 to 25 mM pH 8.0 Tris buffer. The prelyophilization formulation was then lyophilized in a Millrock Revo Freeze Dryer (Model No. RV85S4), using aliquots of 2.0 mL of suspension and the lyophilization cycle provided in Table 18 below.

TABLE 18

Lyophilization Cycle for Self-Replicating RNA-Lipid Nanoparticle Formulation
Freeze drying cycle

| Step | shelf temperature (° C., ±2° C.) | step duration (h:min) | chamber vacuum (mbar) |
|---|---|---|---|
| Initial Freezing | −50 | 4:00 | atmosphere |
| Evacuation | −50 | 00:30-01:45 | from atmosph. pressure to 0.05 |
| Primary drying (ramp down) | −50 → 0 | 63:00 | 0.05 |
| Secondary drying (ramp up) | 0 → +25 | 39:30 | 0.05 |
| Backfill with N$_2$ and stoppering | 25 | 00:10-00:20 | 700 ± 50 |
| Aeration with air | 5 | 00:10-00:20 | atmosphere |

The lyophilized particles prepared following the methods described above were reconstituted in 2 mL of water and characterized using DLS and RIBOGREEN™. The results provided in Table 19 below show that the lyophilized compositions were found to produce lyophilized lipid nanoparticle formulations with adequate size, polydispersity, and delta values (∼5.3 nm) upon reconstitution.

TABLE 19

Self-Replicating RNA-Lipid Nanoparticle
Characteristics Pre- and Post-LYO

| | Average Particle Size (nm) | PDI | Encap (%) |
|---|---|---|---|
| Pre-LYO | 76.3 | 0.129 | 97 |
| Post-LYO | 81.6 | 0.152 | 93 |

Further Considerations

The foregoing description is provided to enable a person skilled in the art to practice the various configurations described herein. While the subject technology has been particularly described with reference to the various figures and configurations, it should be understood that these are for illustration purposes only and should not be taken as limiting the scope of the subject technology.

There may be many other ways to implement the subject technology. Various functions and elements described herein may be partitioned differently from those shown without departing from the scope of the subject technology. Various modifications to these configurations will be readily apparent to those skilled in the art, and generic principles defined herein may be applied to other configurations. Thus, many changes and modifications may be made to the subject technology, by one having ordinary skill in the art, without departing from the scope of the subject technology.

It is understood that the specific order or hierarchy of steps in the processes disclosed is an illustration of exemplary approaches. Based upon design preferences, it is understood that the specific order or hierarchy of steps in the processes may be rearranged. Some of the steps may be performed simultaneously. The accompanying method claims present elements of the various steps in a sample order, and are not meant to be limited to the specific order or hierarchy presented.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

Furthermore, to the extent that the term "include," "have," or the like is used in the description or the claims, such term is intended to be inclusive in a manner similar to the term "comprise" as "comprise" is interpreted when employed as a transitional word in a claim.

In one or more aspects, the terms "about," "substantially," and "approximately" may provide an industry-accepted tolerance for their corresponding terms and/or relativity between items, such as from less than one percent to five percent.

A reference to an element in the singular is not intended to mean "one and only one" unless specifically stated, but rather "one or more." Pronouns in the masculine (e.g., his) include the feminine and neuter gender (e.g., her and its) and vice versa. The term "some" refers to one or more. Underlined and/or italicized headings and subheadings are used for convenience only, do not limit the subject technology, and are not referred to in connection with the interpretation of the description of the subject technology. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable (or possess every advantage that is achievable) by different embodiments of the disclosure in order to be encompassed within the scope of the disclosure. The use herein of "can" and derivatives thereof shall be understood in the sense of "possibly" or "optionally" as opposed to an affirmative capability.

What is claimed is:

1. A pharmaceutical composition comprising a solid lyophilized composition, wherein the solid lyophilized composition comprises:
   i. lipid nanoparticles encapsulating from about 0.001 to about 1.0% w/w of a ribonucleic acid (RNA) by the weight of the lyophilized composition,
   ii. a lyoprotectant composition comprising from about 0.01% w/w to about 1.0% w/w of a poloxamer by the weight of the lyophilized composition and from about 0.5% w/w to about 5.0% w/w of potassium sorbate by the weight of the lyophilized composition, and
   iii. from about 85% w/w to about 96% w/w of a sugar by the weight of the lyophilized composition.

2. The pharmaceutical composition of claim 1, wherein the poloxamer is poloxamer 188.

3. The pharmaceutical composition of claim 1, wherein the solid lyophilized composition comprises from about 0.5 to about 5.0% w/w of lipids by the weight of the solid lyophilized composition.

4. The pharmaceutical composition of claim 1, wherein the solid lyophilized composition further comprises from about 0.5 to about 2.5% w/w of tris(hydroxymethyl)aminomethane by the weight of the solid lyophilized composition.

5. The pharmaceutical composition of claim 1, wherein the solid lyophilized composition further comprises from about 0.75 to about 2.75% w/w of NaCl by the weight of the solid lyophilized composition.

6. The pharmaceutical composition of claim 1, wherein the sugar is sucrose.

7. A method of preserving the solid lyophilized composition of claim 1 comprising storing the lyophilized product at a temperature of about 2° C. to about 8° C.

8. A method of preserving the solid lyophilized composition of claim 1 comprising storing the lyophilized product at a temperature of about −20° C.

9. A method of reconstituting the solid lyophilized composition of claim 1 comprising adding a liquid medium to the lyophilized composition.

10. The method of claim 9, wherein the liquid medium is an aqueous medium.

11. The method of claim 9, wherein the liquid medium further comprises a buffer having a pH of about 7.0 to about 8.5.

12. A method of treating a disease or disorder in a subject comprising administering to the subject the solid lyophilized composition of claim 1 reconstituted in a liquid medium.

13. The method of claim 12, wherein the reconstituted lyophilized composition is administered intravenously, mucosally, or subcutaneously.

14. The method of claim 12, wherein the reconstituted lyophilized composition is administered intramuscularly.

15. The method of claim 12, wherein the reconstituted lyophilized composition is administered via inhalation.

16. A pharmaceutical composition comprising a solid lyophilized composition, wherein the solid lyophilized composition comprises:
   i. lipid nanoparticles encapsulating from about 0.001 to about 1.0% w/w of an RNA by the weight of the lyophilized composition,
   ii. from about 0.01% w/w to about 1.0% w/w of a poloxamer by the weight of the lyophilized composition and from about 0.5% w/w to about 5.0% w/w of potassium sorbate by the weight of the lyophilized composition,
   iii. from about 0.75% w/w to about 2.75% w/w of a salt by the weight of the lyophilized composition, and
   iv. from about 85% w/w to about 96% w/w of a sugar by the weight of the lyophilized composition,
wherein upon reconstitution of the solid lyophilized composition with a liquid medium the lipid nanoparticles have a change in mean diameter less than about 15 nm as compared to a mean diameter prior to lyophilization.

* * * * *

UNITED STATES PATENT AND TRADEMARK OFFICE
CERTIFICATE OF CORRECTION

| | | |
|---|---|---|
| PATENT NO. | : 12,178,921 B2 | Page 1 of 1 |
| APPLICATION NO. | : 17/402077 | |
| DATED | : December 31, 2024 | |
| INVENTOR(S) | : Sagi et al. | |

It is certified that error appears in the above-identified patent and that said Letters Patent is hereby corrected as shown below:

In the Specification

In Column 14, Line 61, delete "Rare" and insert -- $R^8$ are --, therefor.

In Column 21, Line 47, delete "can be comprise" and insert -- can comprise --, therefor.

In Column 32, Line 55, delete "refers" and insert -- refers to --, therefor.

In Column 36, Line 15, delete "can be then be" and insert -- can then be --, therefor.

In Column 40, Line 23, delete "that for" and insert -- for --, therefor.

In Column 42, Line 19, delete "6" and insert -- δ --, therefor.

In Column 42, Line 20, delete "6." and insert -- δ. --, therefor.

In Column 43, Line 23, delete "PVA0," and insert -- PVA1, --, therefor.

In Column 49, Line 34, delete "9000," and insert -- 90%, --, therefor.

In Column 65, Line 11, delete "by was" and insert -- was --, therefor.

In the Claims

In Column 68, Line 46, in Claim 16, delete "iiii." and insert -- iii. --, therefor.

Signed and Sealed this
Twenty-second Day of April, 2025

Coke Morgan Stewart
*Acting Director of the United States Patent and Trademark Office*